US009474793B2

(12) United States Patent
Catanzaro et al.

(10) Patent No.: US 9,474,793 B2
(45) Date of Patent: Oct. 25, 2016

(54) VACCINES AND METHODS FOR PREVENTION AND TREATMENT OF DRUG-RESISTANT HIV-1 AND HEPATITIS B VIRUS

(75) Inventors: Andrew Catanzaro, Washington, DC (US); Robert Yarchoan, Bethesda, MD (US); Jay A. Berzofsky, Bethesda, MD (US); Takahiro Okazaki, Yokohama (JP); James T. Snyder, II, Phoenix, AZ (US); Samuel Broder, Bethesda, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 1969 days.

(21) Appl. No.: 11/816,704

(22) PCT Filed: Feb. 22, 2006

(86) PCT No.: PCT/US2006/006563
§ 371 (c)(1),
(2), (4) Date: Jun. 15, 2009

(87) PCT Pub. No.: WO2006/091798
PCT Pub. Date: Aug. 31, 2006

(65) Prior Publication Data
US 2009/0317418 A1 Dec. 24, 2009

Related U.S. Application Data

(60) Provisional application No. 60/655,984, filed on Feb. 22, 2005.

(51) Int. Cl.
| | |
|---|---|
| *A61K 38/08* | (2006.01) |
| *A61K 39/21* | (2006.01) |
| *C07K 7/06* | (2006.01) |
| *C07D 239/04* | (2006.01) |
| *A61K 39/00* | (2006.01) |

(52) U.S. Cl.
CPC .................................. *A61K 39/00* (2013.01)

(58) Field of Classification Search
CPC .... C07K 14/16; C12N 9/1276; A61K 39/21; C07D 239/04
See application file for complete search history.

(56) References Cited

FOREIGN PATENT DOCUMENTS

| DE | 198 14 925 A1 | 10/1999 |
| WO | WO 03/025166 A1 | 3/2003 |
| WO | WO 03/035097 A1 | 5/2003 |
| WO | WO 2004/092201 A2 | 10/2004 |
| WO | WO 2004/092201 A3 | 10/2004 |

OTHER PUBLICATIONS

Schmitt et al. Specific recognition of lamivudine-resistant HIV-1 by cytotoxic T lymphocytes. AIDS 2000, vol. 14, pp. 653-658.*
Okazaki et al. Epitope-enhanced Conserved HIV-1 Peptide Protects HLA-A2-Transgenic Mice Against Virus Expressing HIV-1 Antigen. Journal of Immunology 2003, vol. 171, No. 5, pp. 2548-2555.*
Pakula et al. Genetic Analysis of Protein Stability and Function. Annual Reviews of Genetics 1989, vol. 23, pp. 289-310.*
Mateu et al. Non-additive Effects of Multiple Amino Acid Subtitutions on Antigen-Antibody Recognition. European Journal of Immunology 1992, vol. 22, pp. 1385-1389.*
Greenspan et al. Defining epitopes: It's not as easy as it seems. Nature Biotechnology 1999, vol. 17, pp. 936-937.*
Gao et al. Effect of a single amino acid change in MHC class I molecules on the rate of progression to AIDS. The New England Journal of Medicine 2001, vol. 344, No. 22, pp. 1668-1675.*
Mason, Rosemarie D., et al.; "Antiretroviral Drug Resistance Mutations Sustain or Enhance CTL Recognition of Common HIV-1 Pol Epitopes;" *The Journal of Immunology*; Jun. 1, 2004; pp. 7212-7219; 172:11.
Okazaki, Takahiro, et al.; "Possible Therapeutic Vaccine Strategy against Human Immunodeficiency Virus Escape from Reverse Transcriptase Inhibitors Studied in HLA-AD Transgenic Mice;" *Journal of Virology*; Nov. 2006; pp. 10645-10651; 80:21.
Samri, Assia, et al.; "Immunogenicity of Mutations Induced by Nucleoside Reverse Transcriptase Inhibitors for Human Immunodeficiency Virus Type 1—Specific Cytotoxic T Cells;" *Journal of Virology*; Oct. 2000; pp. 9306-9312; 74:19.
Stratov, Ivan; "Induction of T-Cell Immunity to Antiretroviral Drug-Resistant Human Immunodeficiency Virus Type 1;" *Journal of Virology*; Jun. 2005; pp. 7728-7737; 79:12.

* cited by examiner

*Primary Examiner* — Louise Humphrey

(74) *Attorney, Agent, or Firm* — Kilpatrick Townsend & Stockton LLP

(57) ABSTRACT

The present invention provides methods for lowering a viral load of a virus resistant to an antiviral drug by inducing cytotoxic T lymphocytes (CTL) to recognize a predetermined mutated epitope within a viral protein of the drug-resistant virus. CTLs are induced by immunizing a host with a peptide comprising the predetermined mutation. The immunostimulating peptide may be further improved by epitope-enhancement for inducing specific CTLs. The antiviral protection against drug-resistant virus shown by compositions of the present invention and mediated by human HLA-restricted CTL has not been previously achieved.

4 Claims, 7 Drawing Sheets

VACCINES AND METHODS FOR PREVENTION AND TREATMENT OF DRUG-RESISTANT HIV-1 AND HEPATITIS B VIRUS

CROSS-REFERENCES TO RELATED APPLICATIONS

This application is a U.S. National Phase of PCT/US2006/006563, filed Feb. 22, 2006, which claims benefit of provisional application Ser. No. 60/655,984, filed Feb. 22, 2005, the disclosure of both of which are incorporated in their entirety by reference.

STATEMENT AS TO RIGHTS TO INVENTIONS MADE UNDER FEDERALLY SPONSORED RESEARCH OR DEVELOPMENT

This application was supported by the Intramural Research Program of the Center for Cancer Research, National Cancer Institute, National Institute of Health.

FIELD OF THE INVENTION

The present invention relates to the fields of immunology and genetics, particularly with regard to diagnostic, prognostic and therapeutic compositions and methods useful in the treatment of viral infections. The present invention has particular utility in the lowering of a viral load, specifically HIV-1 and hepatitis B viruses that are resistant to antiviral drugs, such as lamivudine.

BACKGROUND OF THE INVENTION

In the United States, more than 12 million new cases of sexually transmitted diseases (STDs) occur each year. Of the top 10 reportable diseases in the United States, five are STDs including chlamydia, gonorrhea, syphilis, the Acquired Immune Deficiency Syndrome (AIDS) and hepatitis B virus (HBV) infection. Human immunodeficiency virus (HIV) infection is a chronic disease that erodes the immune system, ultimately resulting in AIDS and death. There is currently no cure for AIDS and many cases of HBV resist treatment.

In the case of AIDS, the World Health Organization recently estimated there are 85 million people worldwide infected with the human immunodeficiency virus (HIV), the virus that causes AIDS. Hepatitis B virus infections affect 5 times more people than HIV. It is estimated that 350 million individuals are chronically infected with HBV and that 1 to 2% will die each year from complications associated with infection, with the majority of these deaths occurring from cirrhosis of the liver and hepatocellular carcinoma.

Replication of HIV is measured by plasma RNA viral load, and in untreated patients, it is estimated that 10 billion virions are produced daily (Levin et al., Science 1997, 275(5298):334-43). If untreated, the infection damages the immune system, resulting in a decline in the CD4 count and subsequent development of opportunistic infections or AIDS related malignancies. Prophylactic regimens can be used to minimize the morbidity and mortality associated with opportunistic infections, such as *pneumocystis carinii* or *mycobacterium avium*.

HIV-infected individuals can be shown to have a variety of immunologic responses to HIV, including cytotoxic T cell responses (to a variety of viral products, including reverse transcriptase), antibody responses, and antibody-dependent cellular cytotoxicity. However, even with these responses, disease progression usually occurs, and patients progress to full-blown AIDS and death.

Vaccines are among the most effective strategies for preventing and controlling viral infections. Vaccines have been proven effective primarily against viruses causing acute, self-limited infections. For these it has been sufficient for the vaccine to mimic the natural virus, such as a live, attenuated virus. However, generally, in chronic viral infections, such as HIV, HBV, Hepatitis C virus (HCV) or human herpesvirus infection, the virus does not elicit an immune response sufficient to eradicate the infection (Berzofsky et al., Nat Rev Immunol 2001, 1(3):209-19; Berzofsky et al., J Clin Invest 2004, 114(4):450-62). Therefore, a vaccine that just mimics the natural infection is not likely to be adequate to induce protection. Also, there is much concern about the use of live attenuated viruses for vaccination against these diseases. Although advances in molecular biology have raised great hope for the development of new vaccine strategies and much effort has been invested in this endeavor, recombinant viral protein vaccines, such as a hepatitis B surface antigen vaccine, have been a rarity (Hilleman, Vaccine 2001, 19:1837-1848).

In the last 5-10 years, however, many new vaccine strategies based on improved ways of inducing antibodies or inducing cytotoxic T lymphocytes (CTLs) have been designed. CTLs detect and destroy cells infected with virus and thereby control and ultimately clear infection. CTLs can detect any viral protein made within an infected host—even when this viral protein is not present on the cell surface. CTLs are also able to respond to peptide fragments of these viral proteins produced by proteasomal cleavage and transported to the endoplasmic reticulum. Here, these peptides bind to newly synthesized class I MHC proteins, such as HLA-A, -B, and -C in humans, which carry the peptides to the cell surface and present them to T-cells (Berzofsky et al., J Clin Invest 2004, 114(4):450-62).

Typically, viral antigens are presented by MHC class I molecules in the form of 8-9 amino acid epitopes that act to stimulate a CTL response. The major CTL immune response to HIV is spread over the gene products Env, Gag, Nef, Vif, Tat, and Pol (Hadida et al., J Immunol 1995, 154(8):4174-86); Walker et al., Science 1988, 240(4848):64-6; Plata et al., Nature 1987, 328(6128):348-51; Koenig et al., Proc Natl Acad Sci USA 1988, 85(22):8638-42; Lamhamedi-Cherradi et al., Aids 1992, 6(11):1249-58).

In protection against HIV, $CD8^+$ CTL play a major role. Many HIV-infected long-term non-progressors have expressed a high level of HIV-specific CTLs. The most direct evidence that $CD8^+$ T lymphocytes, especially CTLs, are involved in controlling HIV infection comes from studies of HIV-infected chimpanzees. Here, depletion of $CD8^+$ T cells in vivo led to an increase in viral load that was later reversed when T cells reappeared (Castro et al., Clin Immunol Immunopathol 1992, 65:227-233). Similar observations were made for SIV in macaques (Schmitz et al., Science 1999, 283:857-860; Jin et al., J Exp Med 1999, 189:991-998).

Although virus-specific CTLs can be elicited by peptides, one approach is to induce endogenous expression of a viral antigen in an antigen-presenting cell, such as a dendritic cell. This seems to be an efficient way to load class I MHC molecules with peptides for presentation to $CD8^+$ T cells (Berzofsky et al., J Clin Invest 2004, 113:1515-1525; Berzofsky et al., J Clin Invest 2004, 114(4):450-62).

However, mutations of HIV allowing the virus to escape from immune control mediated by CTLs are a major concern. This has led to the consideration of new vaccine strategies (reviewed in Berzofsky et al., Nat Rev Immunol 2001, 1(3):209-19). Viral sequences evolving under immune selective pressure would not likely have optimal HLA molecule-binding epitopes. Thus, viral proteins are not naturally selected for high affinity to MHC binding sequences. Indeed, if there is any selection, it is likely to be negative in nature, allowing the virus to escape. Thus, one effective strategy toward development of new generation vaccines is to modify viral epitope sequences to improve the CTL response.

One such strategy involved the creation by sequence modification of enhanced epitopes that bind with higher affinity to MHC molecules. As a possible solution for eliciting an immune response against HIV, Okazaki et al. (J Immunol 2003, 171(5):2548-55) used an epitope-enhancement strategy involving a conserved CTL epitope in HIV reverse transcriptase (RT), VIYQYMDDL (RT-WT, amino acid residues 179-187; SEQ ID NO:1) for the induction of antiviral protection in HLA-A2 transgenic mice mediated by human HLA-A2-restricted CTLs. This strategy involved modifying the conserved epitope sequence to improve binding to human leukocyte antigen (HLA) molecules, such as HLA-A2, which is the most common human class I MHC molecule (Okazaki et al., J Immunol 2003, 171(5):2548-55). Specifically, Okazaki et al., designed two epitope-enhanced peptides based on affinity for HLA-A2, one substituted in anchor residues (RT-2L9V) and the other also with tyrosine at position 1 (RT-1Y2L9V) and examined the balance between HLA binding and T cell recognition. This study demonstrated that the enhanced CTL epitope, in which the anchor residues were modified for enhanced binding to the HLA-A2 molecule, can induce CTL more efficiently while maintaining full crossreactivity to the original viral epitope.

We have previously succeeded in improving the affinity of a hepatitis C core epitope for HLA-A2.1 (Sarobe et al., J. Clin Invest 1998, 102:1239-1248) and of a helper epitope for murine class II MHC (Ahlers et al., Proc Natl Acad Sci USA 1997, 94:10856-10861; Ahlers et al., J Clin Invest 2001, 108:1677-1685). Further, an epitope-enhanced melanoma peptide has shown efficacy in human clinical trials (Rosenberg et al., Nat Med 1998, 4:321-327).

In the case of HIV antiviral therapy has been utilized successfully to control viral replication. Although mortality rates from AIDS are dropping due to new drug therapies, AIDS remains the second leading cause of death in adults between the ages of 29 and 40. Combination anti-HIV therapy is now the standard of care for people infected with HIV and has dramatically decreased the number of AIDS-related deaths. There are 12 anti-HIV drugs available by prescription. These anti-HIV drugs fall into three categories: (i) nucleosides analogs, which include zidovudine, didanosine, zalcitabine, stavudine and lamivudine (or 3TC); (ii) protease inhibitors, which include indinavir, nelfinavir, saquinavir, ritonavir and amprenavir (Akhteruzzaman et al., Antiviral Res 1998, 39:1-23) and (iii) non-nucleoside reverse transcriptase inhibitors, which include nevirapine, delavirdine and efavirenz.

Compared to HIV, there are presently only two licensed therapies for chronic hepatitis B virus infection, interferon and lamivudine. Lamivudine is part of many antiretroviral regimens due to its favorable pharmokinetics, low toxicity, and high potency against HIV. Other drugs are currently under clinical trials including famciclovir, lobucavir and adefovir. However, many studies have shown that most patients relapse after completion of therapy and develop resistance to the drugs.

However, a major barrier to the anti-viral drug treatment of HIV infections is that the high degree of genetic variation and high levels of viral replication often lead to the emergence of drug-resistant variants during treatment. Drug resistance is a major concern in the treatment of HIV and Hepatitis B virus infections. Once a mutation conferring drug resistance occurs, the virus grows unchecked to become the dominant strain of the virus in the affected individual, and the drug becomes progressively less effective against the new strain. In clinical studies, resistance to 3TC was observed in nearly all patients who received 3TC monotherapy for more than 12 weeks (Schuurman et al., J Infect Dis 1995, 171:1411-1419).

A common target for HIV therapy is the reverse transcriptase (RT) of HIV. However, mutations of HIV leading to escape from RT inhibitors and other anti-HIV drugs have been observed. An important component of triple drug anti-AIDS therapy is the (−) enantiomer of 2',3'-dideoxy-3'-thiacytidine (3TC, lamivudine). High-grade resistance to this nucleoside RT inhibitor is initially associated with the appearance of a resistant virus variant containing an M184I alteration in the RT sequence, i.e., a substitution of methionine to isoleucine at position 184 of the HIV RT. This transiently appearing variant is then rapidly replaced by an HIV variant carrying an M184V substitution, i.e., an amino acid substitution of methionine to valine at position 184 of the RT (Boucher et al., Antimicrob Agents Chemother 1993, 37(10):2231-2234; Gao et al., Antimicrob Agents Chemother 1993, 37(6):1390-1392; Sarafianos et al., Proc Natl Acad Sci USA 1999, 96(18):10027-10032; Schuurman et al., J Infect Dis 1995, 171(6):1411-1419; Wainberg et al., AIDS 1995, 9(4):351-357; Johnson et al., Top HIV Med 2003, 11(6):215-221). These mutations result in a >1,000 fold decrease in lamivudine sensitivity (Kanagawa et al., Science 1993, 262:240-2).

Amino residue 184 is contained within the catalytic site of RT, a highly conserved motif of YMDD (SEQ ID NO:2). These lamivudine escape mutations are located within an HLA-A2-restricted CTL epitope, VIYQYMDDL (RT-WT; SEQ ID NO:1) defined in a long-term non-progressing HIV-1 infected individual (Harrer et al., J Infect Dis 1996, 173:476-479). The selection of high level resistance to lamivudine can occur within weeks in patients with incomplete HIV suppression. In addition, the M184I and M184V mutations are also associated with reduced sensitivity to didanosine, zalcitabine and abacavir.

HIV viruses with mutations at residue 184 of RT generally arise only under drug pressure. Because these mutations adversely affect the function of RT and the replicative capacity of HIV-1, these mutations are infrequently found in wild-type virus (Back et al., EMBO J 1996, 15:4040-4049; Wainberg et al., Science 1996, 271:1282-1285).

Sarafianos et al. (Proc Natl Acad Sci USA 1999, 96(18): 10027-32) determined the crystal structure of a 3TC-resistant mutant HIV-1 RT (M184I) and concluded that a steric conflict between the oxathiolane ring of the nucleotide analog 3TCTP and the side chain of beta-branched amino acids (Val, Ile, Thr) at position 184 perturbs inhibitor binding, leading to a reduction in incorporation of the analog. Their model can also explain the 3TC resistance of analogous polymerase mutants. For example, this model suggests that, like HIV-1 RT, a mutation of the methionine of the YMDD (SEQ ID NO:2) motif of hepatitis B polymerase (M552 in HBV) to a beta-branched amino acid would cause a steric conflict with the oxathiolane ring of 3TC. However, additional mutations outside the YMDD (SEQ ID NO:2) motif of the HBV polymerase have been reported to confer 3TC resistance. This suggests that other interactions may also affect HBV polymerase sensitivity to 3TCTP (Chang et al., J Biol Chem 1992, 267(2):13938-13942; Fu and Cheng, Biochem Pharmacol 1998, 55(10):1567-1572). For example, Lindstrom et al. (J Clin Microbiol 2004, 42(10): 4788-4795) reported lamivudine-resistant HBV mutants that display specific mutations in the YMDD (SEQ ID NO:2) motif of the viral polymerase, such as methionine 204 to isoleucine or valine. They found that the latter mutation is often accompanied by a compensatory leucine-to-methionine change at codon 180.

Similar to the HIV-1 and HBV enzymes, simian immunodeficiency virus RT develops resistance to 3TC through a methionine to isoleucine or methionine to valine mutation in the YMDD (SEQ ID NO:2) motif (Cherry et al., Antimicrob Agents Chemother 1997, 41(12):2763-2765). None of the 3TC-resistant clones displayed resistance to 3'-azido-3'-deoxythynidine (AZT) or to the protease inhibitors indinavir and saquinavir, suggesting that resistance to these drugs involves other amino acid residues within RT or protease respectively.

Further, a methionine to threonine mutation in the YMDD (SEQ ID NO:2) motif of feline immunodeficiency virus (FIV) RT confers resistance to oxathiolane nucleosides (Smith et al., J Virol 1997, 71(3):2357-2362). Another mutation, a proline to serine mutation at position 156 of FIV RT was resistant to 3TC, AZT, and the combination of 3TC and AZT (Smith et al., J Virol 1998, 72(3):2335-40).

Schmitt et al. (AIDS 2000, 14(6):653-658) tested whether the M184V mutation of HIV RT represented a new CTL epitope and studied recognition of this epitope in 28 HLA-A2-positive HIV-1-infected patients. In one 43-year-old HIV-infected patient they could isolate a CTL line recognizing the peptide VIYQYVDDL (RT-M184V; SEQ ID NO:3) in conjunction with HLA-A2. The CTL clone also recognized the RT-M184I mutation, but failed to recognize the wild-type epitope, VIYQYMDDL (RT-WT; SEQ ID NO:1). Schmitt et al. concluded that CTL can specifically recognize lamivudine-resistant HIV-1 variants and that the cellular response could have an important influence on the control of drug-resistant virus. They also noted that the immune system can generate new CTL specificities even in patients with advanced disease, as the M184V HIV variant emerges only after drug treatment. However, Schmitt et al. could not determine whether these CTL in this 43-year-old patient were already present in the peripheral T cell repertoire or whether they were generated from lymphoid stem cells de novo. In the same study, Schmitt et al. reported that, although drug therapy was not able to suppress HIV-viraemia in this patient, plasma viral load remained stable at low levels and even declined over time gradually without change in antiviral therapy, suggesting that the HIV-1 specific immune response contributed to the control of HIV-1 in this patient. Schmitt et al. concluded that further studies are necessary to examine whether the induction of CTL against drug-escape variants can help to delay or even prevent the emergence of drug-resistant HIV-1 strains.

Although several approaches have been tried to overcome the problem of drug-resistant strains, most appear to simply delay the onset of resistance. A method addressing infection with drug-resistant strains is therefore a primary concern to health care providers.

In the present invention we demonstrate the use of a therapeutic HIV vaccine along with HIV antiviral therapy to develop CTLs specific for mutations that confer resistance to an antiviral drug in order to prevent such resistant mutants from occurring. These vaccines can also be optimized utilizing epitope enhancement.

BRIEF SUMMARY OF THE INVENTION

While the present invention may be embodied in many different forms, several specific embodiments are discussed herein with the understanding that the present disclosure is to be considered only as an exemplification of the principles of the invention, and is not intended to limit the invention to the embodiments illustrated.

The present invention provides compositions comprising an antiviral drug and a synthetic peptide which comprises a predetermined antiviral drug-resistant mutation in a viral protein of an antiviral drug-resistant virus.

It is also an objective of the present invention to provide methods using the compositions of the invention to lower the viral load of a virus wherein the virus causes a chronic viral infection and is resistant to an antiviral drug. The method comprises the step of administering to a host a medicament, wherein the medicament comprises an antiviral drug in an amount effective to restrict the intracellular multiplication of the virus and capable of selecting for a predetermined antiviral drug-resistant mutation in a viral protein, thereby creating an antiviral drug-resistant virus. The medicament further comprises a synthetic peptide having a length of between 9 and 15 amino acid residues. This synthetic peptide comprises the predetermined antiviral drug-resistant mutation in the viral protein and at least six amino acid residues flanking the predetermined antiviral drug-resistant mutation that are identical to the amino acid sequence of the viral protein of the antiviral drug-resistant virus. The synthetic peptide induces a cytotoxic T lymphocyte response specific for cells infected with the antiviral drug-resistant virus.

An antiviral drug useful for compositions and methods of the present invention is selected from the group consisting of zidovudine, didanosine, zalcitabine, stavudine, lamivudine, nevirapine, delavirdine, efavirenz, adefovir, adefovir dipivoxil, FTC, D4FC, BCH-189, F-ddA, tetrahydroimidazo[4,5,1-jk[ ]1,4]benzodiazepine-2(1H)-one, tetrahydroimidazo[4,5,1-jk[ ]1,4]benzodiazepine-2(1H)-thione, (S)-4-isopropoxycarbonyl-6-methoxy-3-(methylthiomethyl)-3,4,-dihydroquinoxaline-2(1H)-thione, saquinavir, ritonavir, indinavir, nelfinavir amprenavir, entecavir, famciclovir, a benzo-1,2,4-thiadiazine antiviral agent, ribavirin, interferon and derivatives thereof. Preferred antiviral drugs are lamivudine and FTC.

The compositions and methods of the invention are useful to target many viruses that can develop antiviral drug resistance, referred to herein as antiviral drug-resistant viruses. These viruses include HIV-1, HIV-2, hepatitis B virus (HBV), hepatitis C virus (HCV) and human herpesviruses. In a preferred embodiment of the present invention, the virus is HIV-1.

Viral proteins that can be targeted using the compositions and methods of the present invention include HIV-1 reverse transcriptase and HIV-1 protease.

In one embodiment of the present invention, a synthetic peptide comprises a predetermined antiviral drug-resistant mutation in HIV-1 reverse transcriptase. A predetermined antiviral drug-resistant mutation in HIV-1 reverse transcriptase is selected from the group consisting of Met41Leu, Glu44Asp, Glu44Ala, Ile50Val, Ala62Val, Lys65Arg, Asp67Asn, Ser68Gly, Thr69Asp, Thr69Ser-Ser-Gly, Thr69Ser-Thr-Gly, Thr69Ser-Val-Gly, Lys70Arg, Lys70Glu, Leu74Ile, Leu74Val, Val75Ile, Val75Leu, Val75Thr, Phe77Leu, Leu100Ile, Lys103Asn, Val106Ala, Val108Ala, Val108Ile, Phe116Tyr, Val118Ile, Pro119Ser, Ile135Met, Ile135Val, Gln151Met, Thr165Ile, Val179Asp, Tyr181Cys, Tyr181Ile, Met184Ala, Met184Ile, Met184Val, Tyr188His, Tyr188Leu, Gly190Ala, Gly190Cys, Gly190Glu, Gly190Gln, Gly190Ser, Gly190Thr, Leu210Trp, Leu214Phe, Thr215Tyr, Thr215Phe, Thr215Ser, Lys219Gln, Pro294Ser, and Gly333Glu.

In another preferred embodiment of the present invention, a synthetic peptide comprises a predetermined antiviral drug-resistant mutation in HIV-1 protease. A predetermined antiviral drug-resistant mutation in HIV-1 protease is selected from the group consisting of Leu10Ile, Leu10Val, Leu10Phe, Gly16Glu, Asp30Asn, Val32Ile, Glu35Asp, Met36Ile, Met46Ile, Met45Leu, Ile47Val, Gly48Val, Ile50Val, Ile54Met, Ile54Ser, Ile54Val, Asp60Val, Leu63Pro, Ala71Thr, Ala71Val, Val77Ile, Val82Ala, Val82Ile, Val82Phe, Val82Thr, Ile84Ala, Ile84Val, Asn88Asp, Asn88Ser, Leu89Met, Leu89Pro and Leu90Met.

In another embodiment, the predetermined antiviral drug-resistant mutation in HIV-1 reverse transcriptase comprises an amino acid substitution of methionine to isoleucine or valine at position 184 of the HIV-1 reverse transcriptase. Thus, a synthetic peptide of the present invention comprises the amino acid sequence VIYQYIDDL (SEQ ID NO:4) or VIYQYVDDL (SEQ ED NO:3).

In a preferred embodiment of the present invention, at least one amino acid residue of the synthetic peptide serves as an epitope enhancement. Thus, a synthetic peptide may also comprise the amino acid sequence VLYQYIDDV (SEQ ID NO:5) or VLYQYVDDV (SEQ ID NO:6).

In another embodiment, the predetermined antiviral drug-resistant mutation in the HIV-1 reverse transcriptase comprises an amino acid substitution of aspartic acid to asparagine at position 67, an amino acid substitution of lysine to arginine at position 70, or a combination of both. In a preferred embodiment the synthetic peptide comprises an amino acid sequence selected from the group consisting of VFAIKKKNSTKWRKL (SEQ ID NO:7), PVFAIKKKNSTKWRK (SEQ ID NO:8), FAIKKKNSTKWRKLV (SEQ ID NO:9), AIKKKDSTRWRKLVD (SEQ ID NO:10), IKKKDSTRWRKLVDF (SEQ ID NO:11), KKKDSTRWRKLVDFR (SEQ ID NO:12), VFAIKKKNSTRWRKL (SEQ ID NO:13), FAIKKKNSTRWRKLV (SEQ ID NO:14), AIKKKNSTRWRKLVD (SEQ ID NO:15) and IKKKNSTRWRKLVDF (SEQ ID NO:16).

In another embodiment of the present invention, the virus is HBV and the viral protein is HBV polymerase. In one embodiment of the present invention, the predetermined antiviral drug-resistant mutation in HBV polymerase is selected from the group consisting of Ser78Thr, Leu80Ile, Leu80Val, Ile169Thr, Val173Leu, Leu180Met, Thr184Gly, Thr184Ser, Ser202Ile, Met204Arg, Met204Ile, Met204Ser, Met204Val, Asp206Asn, Val207Ile, Asn236Thr and Met250Val.

The invention also provides for a medicament for lowering viral load in a host. The medicament comprises a synthetic peptide and an antiviral drug in an amount effective to restrict the intracellular multiplication of a wild-type virus, but substantially less effective in restricting intracellular multiplication of an antiviral drug-resistant virus, wherein the antiviral drug-resistant virus differs from the wild-type virus by at least one substitution, insertion or deletion of one amino acid residue in a reverse transcriptase or protease of the wild-type HIV-1 virus. The synthetic peptide comprises an amino acid sequence of between 9 and 15 amino acid residues and a predetermined antiviral drug-resistant mutation in HIV-1 reverse transcriptase or HIV-1 protease.

In one aspect, at least one amino acid residue of the synthetic peptide serves as an epitope enhancement. Thus, a preferred amino acid sequence of the synthetic peptide comprises VLYQYVDDV (SEQ ID NO:6) or VLYQYIDDV (SEQ ID NO:5).

The invention further provides for a method for destroying cells infected with an antiviral drug-resistant virus. This method comprises the steps of (a) inducing cytotoxic T lymphocytes to recognize a mutated epitope of the antiviral drug-resistant virus and (b) contacting the cells with the cytotoxic T lymphocytes thereby destroying the cells. In a preferred embodiment of the present invention, the antiviral drug-resistant virus is a mutated HIV-1 and the mutated epitope is within the mutated HIV-1 reverse transcriptase or within the mutated HIV-1 protease. Cytotoxic T lymphocytes are induced by immunization of a host with a synthetic peptide comprising a predetermined antiviral drug-resistant mutation in HIV-1 reverse transcriptase or HIV-1 protease.

In a preferred embodiment of the invention, at least one amino acid residue of the synthetic peptide serves as an epitope enhancement. In one embodiment, the synthetic peptide comprises the amino acid sequence selected from the group of VLYQYVDDV (SEQ ID NO:6), YLYQYVDDV (SEQ ID NO:17), VLYQYIDDV (SEQ ID NO:5), YLYQYIDDV (SEQ ID NO:18), VIYQYIDDL (SEQ ID NO:4) and VIYQYVDDL (SEQ ID NO:3). In another embodiment, the synthetic peptide comprises the amino acid sequence selected from the group of VLYQYVDDV (SEQ ID NO:6), VLYQYIDDV (SEQ ID NO:5), VIYQYIDDL (SEQ ID NO:4) and VIYQYVDDL (SEQ ID NO:3).

The present invention also provides a method for providing an immune counter-selective pressure to prevent or suppress a viral escape mutation during antiviral therapy. This method comprises the steps of (a) enhancing an epitope of a viral amino acid sequence comprising a predetermined antiviral drug-resistant mutation, wherein the enhancing is performed by altering the amino acid sequence of the epitope and (b) inducing cytotoxic T lymphocytes to specifically recognize the predetermined antiviral drug-resistant mutation in a viral protein using the enhanced epitope of step (a). In a preferred embodiment of the present invention, the virus is HIV-1 and the viral escape mutation comprises a predetermined antiviral drug-resistant mutation in HIV-1 reverse transcriptase or HIV-1 protease. In a preferred embodiment, at least one amino acid residue of the epitope is altered and serves as an epitope enhancement. The cytotoxic T lymphocytes are induced by immunization of a host with a synthetic peptide comprising an amino acid sequence selected from the group of VLYQYVDDV (SEQ ID NO:6), YLYQYVDDV (SEQ ID NO:17), VLYQYIDDV (SEQ ID NO:5), YLYQYIDDV (SEQ ID NO:18), VIYQYIDDL (SEQ ID NO:4) and VIYQYVDDL (SEQ ID NO:3). In another embodiment, the synthetic peptide comprises the amino acid sequence selected from the group of VLYQYVDDV (SEQ ID NO:6), VLYQYIDDV (SEQ ID NO:5), VIYQYIDDL (SEQ ID NO:4) and VIYQYVDDL (SEQ ID NO:3).

The present invention also provides for a method for eradicating a viral escape mutant virus. This method comprises (a) enhancing an epitope of a viral amino acid sequence comprising a predetermined antiviral drug-resistant mutation, wherein the enhancing is performed by altering the amino acid sequence of the epitope and (b) inducing cytotoxic T lymphocytes to specifically recognize the predetermined antiviral drug-resistant mutation in a viral protein using the enhanced epitope of step (a).

Further, the invention provides for an immunostimulating peptide or protein comprising an amino acid sequence of the formula $X_1Y_1P_MY_2X_2$, wherein $P_M$ is a predetermined antiviral drug-resistant mutation in HIV-1 reverse transcriptase or HIV-1 protease. $Y_1$ is an amino acid sequence comprising from 2 to 12 amino acid residues identical to an amino acid sequence in HIV-1 reverse transcriptase or HIV-1 protease and is amino-terminal to the predetermined antiviral drug-resistant mutation. $Y_2$ is an amino acid sequence comprising from 2 to 12 amino acid residues identical to an amino acid sequence in HIV-1 reverse transcriptase or HIV-1 protease and is carboxy-terminal to the predetermined antiviral drug-resistant mutation. $X_1$ is an amino acid sequence of between 0 and 100 amino acid residues in length and is amino-terminal to and $Y_1$. $X_2$ is an amino acid sequence of between 0 and 100 amino acid residues in length and is carboxy-terminal to and $Y_2$.

The immunostimulating peptide may further comprise an amino acid substitution within $Y_1$ or $Y_2$ or both, wherein the amino acid substitution serves as an epitope enhancement. In a preferred embodiment of the present invention, an immunostimulating peptide of the present invention comprises the amino acid sequence LYQYVDDV (SEQ ID NO:19) or LYQYIDDV (SEQ ID NO:20). Immunostimulating peptides of the present invention may further comprise an acetylated N-terminus or a modification to the C-terminus selected from the group consisting of amidation, esterification, and reduction of a C-terminal amino acid carboxyl group.

The invention further provides for a medicament comprising a dendritic cell displaying on its cell surface an immunostimulating peptide.

In another preferred embodiment of the present invention, a medicament comprises an immunostimulating peptide and a pharmaceutically acceptable carrier. The medicament may further comprise an immunostimulating agent, for example a protein to which a host is immune and which stimulates a cytotoxic T lymphocyte response. The invention further provides a method for lowering viral load comprising the step of administering to a host the medicament in an amount effective to induce an immune response capable of lowering the viral load in the host.

DEFINITIONS

Figure 1A:
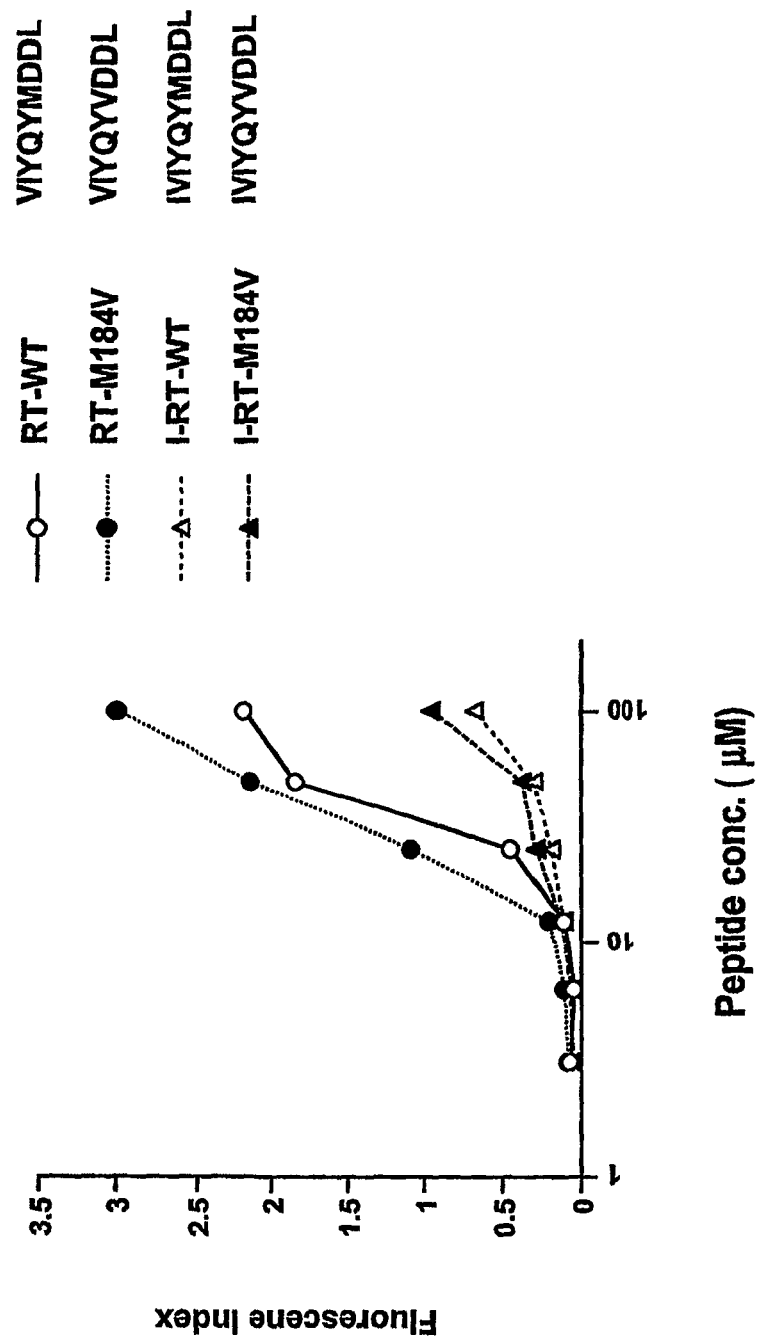
Figure 1a shows a comparison of the HLA-A2 binding curves among the wild type RT -WT (VIYQYMDDL; SEQ ID NO:1), RT-M184V (VIYQYVDDL; SEQ ID NO:3), I-RT-WT (IVIYQYMDDL; SEQ ID NO:21), I-RT-M184V (IVIYQYVDDL; SEQ ID NO:22) in the T2 -binding assay.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

"Amino acid" and "amino acid residue" refer to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and o-phosphoserine. Amino acids may be referred to herein by either their commonly known three letter symbols or by the one-letter symbols recommended by the IUPAC-IUB Biochemical Nomenclature Commission.

"Amino acid sequence" refers to the positional relationship of amino acid residues as they exist in a given peptide or protein.

"Amino acid substitution" means replacement of one amino acid residue within an amino acid sequence by another amino acid residue.

"Amount effective" means an amount which produces the desired effect.

"Antiviral drug" is any compound or composition that prevents or suppresses infection of a cell, or multiplication of a virus within a cell, or release of a virus from a cell, or causes clearance of viral particles from a host. Typically, antiviral drugs interfere with transcription of viral genes translation of viral proteins and/or other key viral enzymes or functions. For purposes of this invention where an antiviral drug includes compounds with chirality, "antiviral drugs" includes racemic mixtures and well as homogenous preparations of enantiomers and all combinations there between. Antiviral drug also includes prodrugs that are converted to the active drug or moiety in the body of a host. A preferred host is a human.

"Antiviral drug-resistant virus" or "virus resistant to an antiviral drug" means that the capability of a virus to infect a cell, to replicate or to be released from a cell or the clearance of viral load from a host is not as affected by administration of an antiviral drug as is the capability of a wild-type virus to infect a cell, to replicate or to be released from a cell or the clearance of wild-type viral load from a host. Usually, transcription of viral genes, translation of viral protein synthesis, replication of viral RNA or DNA, assembly of viral proteins and/or modification of viral proteins of the antiviral drug-resistant virus is not as significantly prevented or suppressed by an antiviral drug when compared to the wild type virus. Upon administration of an antiviral drug the viral load of an antiviral drug-resistant virus is not as significantly lowered as is the viral load of a wild-type virus.

"Carrier" in the context of "pharmaceutically acceptable carrier" refers to refers to an inert substance used as a diluent, adjuvant, excipient or vehicle with which a drug, medicament or vaccine is administered.

"Chronic viral infection" refers to a permanent or long-lasting presence of a virus in a host, preferably a patient, when left untreated. Chronic viral infections often have one or more of the following characteristics: they are permanent; cause chronic disease; require special training for treatment of the host, preferably a patient, require rehabilitation, or may require a long period of care. For example, chronic infections with HIV-1 include asymptomatic seropositivity, AIDS-related complex (arc), and acquired immunodeficiency syndrome (AIDS).

"Cytotoxic T lymphocyte" or "CTL" refers to a type of lymphocyte that matures in the thymus and has the ability to recognize specific peptide antigens, or specific peptide antigens complexed with a major histocompatability complex protein (MHC), through the receptors on its cell surface. CTL can kill cells that are infected by a specific virus or other intracellular microbe.

"Cytotoxic T lymphocyte response" is any physiological change resulting in activation and/or expansion of a "CTL" cell population.

"Having a length of between 9 and 15 amino acid residues" in the context of a peptide of the present invention or grammatical equivalents thereof means a peptide having 9, 10, 11, 12, 13, 14 or 15 amino acid residues.

"Host" includes mammals, for example, humans, dogs, cows, horses, pigs, sheep, goats, cats, mice, rabbits, rats, and transgenic nonhuman mammals. Preferably, the host is a human, most preferably a human patient.

"Immunostimulating" and grammatical variants thereof, refer to any substance capable of stimulating an immune response. Immunostimulating agents include, but are not limited to, adjuvants such as alum, cytokines polysaccharides and the like.

"Lowering viral load" refers to lowering the number of viral particles in a sample, such as plasma by a statistically significant amount. Viral load is increasingly employed as a surrogate marker for disease progression. It can be measured, for example, by PCR, bDNA tests and ELISA and is expressed in number of viral copies or equivalents per milliliter.

"Peptide" and "protein" are used herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer. Peptides and proteins of the present invention include amino acid polymers having D- and L-isoforms of individual amino acid residues, as well as other amino acid variants, as described herein. Peptides are distinguished by the number of amino acid residues making up the primary structure of the molecule. For purposes of this invention, peptides are those molecules comprising up to 50 amino acid residues, and proteins comprise 50 or more amino acid residues. However, methods of synthesis and/or delivery of peptides and proteins of the invention are similar, if not identical, as will be appreciated by one of skill in the art. Therefore, where appropriate, these terms are synonymous when discussing methods of synthesis, modification or use as therapeutic or diagnostic reagents.

"Pharmaceutically acceptable" means approved by a regulatory agency of the Federal or a state government or listed in the U.S. Pharmacopeia or other generally recognized pharmacopeia for use in animals, and more particularly in humans.

"Predetermined antiviral drug-resistant mutation" refers to an amino acid difference in an amino acid sequence of a viral protein identified in an antiviral drug-resistant virus compared to the amino acid sequence in the corresponding viral protein of a wild-type virus. Such a mutation can either be one or more amino acid substitutions, one or more amino acid insertions or one or more amino acid deletions.

"Prevent or suppress a viral escape mutation" means that upon administration of an antiviral drug, a viral escape mutation in a viral protein is prevented and that the viral load of a virus carrying this viral escape mutation is significantly lowered.

"Substantially less effective" in the context of an antiviral drug means that while an antiviral drug significantly lowers the viral load of a wild-type virus, the antiviral drug lowers the viral load of an antiviral drug-resistant virus to a lesser extent.

"Viral escape mutation" refers to a mutation in a viral protein allowing the virus carrying such mutation to escape or partially escape the effect of an antiviral drug.

"Viral infection" refers to the presence of a virus in a subject, particularly in a human subject.

"Wild-type virus" refers to a viral isolate obtained in the absence of an antiviral drug. The DNA, RNA or viral protein sequence of a wild-type virus is referred to as wild-type DNA sequence, wild-type RNA sequence or wild-type protein sequence.

Incorporation by Reference

To ensure a full description of the invention, all publications, patents and patent applications cited in this specification are herein incorporated in their entireties by reference as if each individual publication, patent or patent application were specifically and individually indicated to be incorporated by reference.

DETAILED DESCRIPTION OF THE INVENTION

Here, we describe novel combination approaches—using both an antiviral drug and a modified peptide to induce immunity to a sequence conferring resistance, thus "boxing in" a virus causing a chronic viral infection between the antiviral drug and the immune response to that peptide. The combination approach presented use the potential Achille's heel of peptide vaccines—that the response is focused on a small sequence—to an advantage in that it is focused on a sequence that confers antiviral drug resistance.

One important aspect of the present invention is the use of a short peptide epitope encompassing a predetermined antiviral drug-resistant mutation as a vaccine to induce a cytotoxic T lymphocyte response to put a negative selective pressure on the antiviral drug-resistant viral mutants to counteract the selective pressure of the antiviral drug itself that favors the resistant mutants, thus boxing the virus between two opposing selective pressures. A vaccine of the present invention selects against a mutant sequence, for example, VIYQYVDDL (SEQ ID NO:3;within the RT of HIV-1), in favor of the drug-sensitive wild-type sequence, for example V1YQYMDDL (SEQ ID NO:1; within the RT of HIV-1). To accomplish this, we have developed novel epitope-enhanced peptides in which at least one amino acid residue within peptides encompassing a predetermined antiviral drug-resistant mutation is altered to increase the affinity of these peptide epitopes for an HLA molecule. In a preferred embodiment of the present invention, one epitope-enhanced peptide comprises the amino acid sequence VLYQYVDDV (SEQ ID NO:6). Here, 2L and 9V are the amino acid substitutions leading to the epitope enhancement, 6V is the predetermined antiviral drug-resistant mutation and 1V, 3Y, 4Q, 5Y, 7D, and 8D are amino acid residues derived from the RT of HIV-1.

1. Compositions Comprising an Antiviral Drug and a Synthetic Peptide with a Predetermined Antiviral Drug-Resistant Mutation Identified in a Viral Protein The present invention relates to compositions comprising an antiviral drug and a synthetic peptide comprising a predetermined antiviral drug-resistant mutation identified in a viral protein of an antiviral drug-resistant virus.

1.1. Antiviral Drugs

The present invention provides for compositions comprising an antiviral drug and a synthetic peptide comprising a predetermined antiviral drug-resistant mutation in a viral protein as described further herein. In a preferred embodiment, a composition of the present invention comprises an antiviral drug in an amount effective to restrict intracellular multiplication of a virus and capable of selecting for a predetermined antiviral drug-resistant mutation in a viral protein, thereby creating an antiviral drug-resistant virus.

Upon prolonged administration of, for example, an antiviral drug monotherapy (using only one antiviral drug instead of a drug cocktail for treatment of a chronic viral infection) many antiviral drugs lead to the escape of antiviral drug-resistant viruses (See Tables 1 to 5). Escape of antiviral drug-resistant viruses is also a substantial problem with combination therapy utilizing two or more antiviral drugs. Antiviral drugs useful for the compositions and methods of the present invention include, but are not limited to, for example, zidovudine, didanosine, zalcitabine, stavudine, lamivudine, nevirapine, delavirdine, efavirenz, adefovir, adefovir dipivoxil, FTC, D4FC, BCH-189, F-ddA, tetrahydroimidazo[4,5,1-jk][1,4]benzodiazepine-2(1H)-one, tetrahydroimidazo[4,5,1-jk[ ]1,4]benzodiazepine-2(1H)-thione, (S)-4-isopropoxycarbonyl-6-methoxy-3-(methylthiomethyl)-3,4,-dihydroquinoxaline-2(1H)-thione, saquinavir, ritonavir, indinavir, nelfinavir amprenavir, entecavir, famciclovir, a benzo-1,2,4-thiadiazine antiviral agent, ribavirin, interferon and derivatives thereof. A preferred antiviral drug is lamivudine.

Another preferred antiviral drug is emtracitabine (FTC). Emtracitabine (FTC), which was approved recently, is similarly resistant to HIV with M184V mutation and can rapidly select for this mutation in monotherapy. Thus, another preferred antiviral drug is emtracitabine (beta-L-2',3'-dideoxy-5-fluoro-3'-thiacytidine (FTC); Faraj et al., 1994, Antimicrob Agents Chemother 38(10):2300-5; Ray et al., 2002, Antiviral Res 56(3):189-205).

In a preferred embodiment of the present invention, the antiviral drug is a drug inhibiting HIV reverse transcriptase. Antiviral drugs inhibiting HIV-1 reverse transcriptase include, but are not limited to, for example, zalcitabine(2',3'-dideoxycytidine; ddC), zidovudine(3'-azido-2',3'-dideoxythymidine; AZT), didanosine(2',3'-dideoxyinosine; ddI), lamivudine((−)2',3'-dideoxy-3'-thiacytidine; 3TC), stavudine(2',3'-didehydro-2',3'-dideoxythymidine; D4T), (−) enantiomer of 2',3'-dideoxy-5-fluoro-3'-thiacytidine [(−) FTC], (−) enantiomer of 2',3'-dideoxy-3'-thiacytidine [(−)-BCH-189], adefovir dipivoxil [bis(pivaloyloxymethyl)-ester prodrug], adefovir[9-(2-phosphonylmethoxyethyl)adenine], 2'-beta-Fluoro-2',3'-dideoxyadenosine (F-ddA); tetrahydroimidazo[4,5,1-jk][1,4]benzodiazepine-2(1H)-one and -thione (TIBO) derivatives (e.g., R82150), nevirapine; (S)-4-isopropoxycarbonyl-6-methoxy-3-(methylthiomethyl)-3,4dihydroquinoxaline-2(1H)-thione (HBY097); and combinations thereof.

In another embodiment of the invention, the antiviral drug is an HIV-1 protease inhibitor. HIV-1 protease inhibitors useful for the present invention include, but are not limited to, for example, saquinavir (Ro 31-8959, Roche), ritonavir (ABT-538, Abbott), indinavir (MK-639, Merck), nelfinavir (AG 1343, Agouron), amprenavir (141W94 or VX-478, Glaxo Wellcome), ABT-378 (Abbott), PNU-140690 (Pharmacia-Upjohn), DMP-450 (Triangle), and DMP-851 (DuPont Merck).

In another embodiment of the present invention, the antiviral drug is an HBV polymerase inhibitor. HBV polymerase inhibitors useful for the present invention include, but are not limited to, for example, entecavir (ETV), lamivudine (3TC), adefovir dipivoxil (ADV), famciclovir, gangciclovir, foscarnet, penciclovir[9-(4)-hydroxy-3-hydroxymethyl-but-1-yl)guanine], CDG (carbocyclic 2'deoxyguanosine), abacavir([1S,4R]-4-[2-amino-6-(cyclopro-plamino)-9H-purin-9-yl]-2-cyclopentene-1-methanol).

Antiviral drugs useful to reduce HCV load include nonnucleoside inhibitors of the HCV RNA-dependent RNA polymerase (NS5B), such as benzothiadiazine, disubstituted phenylalanine, and benzimidazole derivatives (Sasky, J Antimicrob Chemother 2004, 51(1):14-6).

Antiviral drugs useful to reduce HCV load also include inhibitors of the HCV NS5A protein, such interferon, particularly interferon-α, with or without ribavirin.

1.2. Synthetic Peptides with Predetermined Antiviral Drug-Resistant Mutations Identified in a Viral Protein The present invention provides for compositions comprising an antiviral drug as described above and a synthetic peptide having a length of between 9 and 15 amino acid residues and comprising a predetermined antiviral drug-resistant mutation in a viral protein. Useful predetermined antiviral drug-resistant mutations include, but are not limited to those described in Tables 1-5 herein. Alternatively, a predetermined antiviral drug-resistant mutation in a viral protein may be identified by sequencing the nucleotide sequence of the antiviral drug-resistant virus isolated from a host.

The synthetic peptide comprises at least six (6) amino acid residues flanking the predetermined antiviral drug-resistant mutation that are identical to the amino acid sequence of the viral protein of the antiviral drug-resistant virus. Synthetic peptides of the present invention may be described by comprising an amino acid sequence of one of the following formulas: $P_M A_1 A_2 A_3 A_4 A_5 A_6$, $A_1 P_M A_2 A_3 A_4 A_5 A_6$, $A_1 A_2 P_M A_3 A_4 A_5 A_6$, $A_1 A_2 A_3 P_M A_4 A_5 A_6$, $A_1 A_2 A_3 A_4 P_M A_5 A_6$, $A_1 A_2 A_3 A_4 A_5 P_M A_6$, or $A_1 A_2 A_3 A_4 A_5 A_6 P_M$, wherein, $A_1$, $A_2$, $A_3$, $A_4$, $A_5$, and $A_6$ are the six amino acid residues flanking the predetermined antiviral drug resistant mutation ($P_M$).

A synthetic peptide having a length of 9 amino acid residues comprises in addition amino acid residues $A_7$ and $A_8$, which may also be identical to the amino acid sequence of the viral protein of the antiviral drug-resistant virus. However, $A_7$ and $A_8$ may also be unrelated to the viral protein sequence.

In a preferred embodiment of the present invention the predetermined antiviral drug-resistant mutation in HIV-1 reverse transcriptase comprises an amino acid substitution of methionine to isoleucine or valine at position 184 of HIV-1 reverse transcriptase. Thus, a preferred synthetic peptide comprises the amino acid sequence VIYQYIDDL (SEQ ID NO:4) or VIYQYVDDL (SEQ ID NO:3). By way of example, in the peptide sequence VIYQYVDDL (SEQ ID NO:3), comprising one predetermined mutation ($P_M$, here, 6V) and eight amino acid residues identical to the amino acid sequence of HIV-1 RT (1V, 2I, 3Y, 4Q, 5Y, 7D, 8D, and 9L) the synthetic peptide can be described as comprising an amino acid sequence corresponding to one of the following formulas: $A_7 A_8 A_1 A_2 A_3 P_M A_4 A_5 A_6$ (wherein 1V is $A_7$, 2I is $A_8$, 3Y is $A_1$, 4Q is $A_2$, 5Y is $A_3$, 6V is $P_M$, 7D is $A_4$, 8D is $A_5$, and 9L is $A_6$; SEQ ID NO:3), $A_7 A_1 A_2 A_3 A_4 P_M A_5 A_6 A_8$ (wherein 1V is $A_7$, 2I is $A_1$, 3Y is $A_2$, 4Q is $A_3$, 5Y is $A_4$, 6V is $P_M$, 7D is $A_5$, 8D is $A_6$, and 9L is $A_8$; SEQ ID NO:3), or $A_1 A_2 A_3 A_4 A_5 P_M A_6 A_7 A_8$ (wherein 1V is $A_1$, 2I is $A_2$, 3Y is $A_3$, 4Q is $A_4$, 5Y is $A_5$, 6V is $P_M$, 7D is $A_6$, 8D is $A_7$, and 9L is $A_8$; SEQ ID NO:3).

However, also permutations of the above sequences, where $A_7$ and $A_8$ are interspersed between $A_1$ to $A_6$ are possible, such that the sequence VIYQYVDDL (SEQ ID NO:5) could be described by the formulas: $A_1 A_2 A_3 A_7 A_8 P_M A_4 A_5 A_6$, $A_1 A_2 A_3 A_4 A_8 P_M A_4 A_5 A_6$ or $A_1 A_2 A_7 A_8 A_3 P_M A_4 A_5 A_6$. Several other permutations are possible and considered distinct embodiments of the present invention. Thus, what is important for the peptides of the present invention is that the synthetic peptide of 9 to 15 amino acid residues comprises a predetermined antiviral drug-resistant mutation ($P_M$) and at least six amino acid residues ($A_1$ through $A_6$) flanking the predetermined antiviral drug-resistant mutation that are identical to the amino acid sequence of the viral protein of the antiviral drug-resistant virus (and occur at the identical position with respect to $P_M$). The other two amino acid residues, $A_7$ and $A_8$, when unrelated to the viral protein sequence may occur anywhere within the 9mer synthetic peptide, as long as $A_1$ through $A_6$ occur at the identical position with respect to $P_M$.

Typically, amino acid residues $A_7$ and $A_8$ (or $A_9$ up to $A_{14}$ in peptides up to 15 amino acid residues in length) are identical to the amino acid sequence of the viral protein of the antiviral drug-resistant virus. In another preferred embodiment, described in detail below, at least one of the amino acid sequence residues of the synthetic peptide serves as an epitope enhancement. Thus, another preferred peptide of the present invention comprises the amino acid sequence VLYQYIDDV (SEQ ID NO:5) or VLYQYVDDV (SEQ ID NO:6). According to the above formula, the amino acid sequence of the peptide VLYQYVDDV (SEQ ID NO:6) can be described by the formula $A_1 A_7 A_2 A_3 A_4 P_M A_5 A_6 A_8$, wherein 1V is $A_1$, 2L is $A_7$, 3Y is $A_2$, 4Q is $A_3$, 5Y is $A_4$, 6V is $P_M$, 7D is $A_5$, 8D is $A_6$, and 9V is $A_8$ (SEQ ID NO:6). In this example of a synthetic peptide, $A_1$ through $A_6$ are identical to the amino acid sequence of the viral protein of the antiviral drug-resistant virus (and occur at the identical position with respect to $P_M$) and $A_7$ and $A_8$ are amino acid sequences that serve as an epitope enhancement and are not identical to the amino acid sequence of the viral protein of the antiviral drug-resistant virus. When the peptide VIYQYVDDL (SEQ ID NO:3; comprising the predetermined mutation 6V in the context of the viral RT sequence) is compared to the peptide VLYQYVDDV (SEQ ID NO:6; comprising the predetermined mutation 6V in the context of the viral sequence and comprising two anchor-enhanced amino acids, 2L and 9V), 2L and 9V within the peptide VLYQYVDDV (SEQ ID NO:6) can also be considered amino acid substitutions of 2I and 9L within the peptide VIYQYVDDL (SEQ ID NO:3).

While the above examples show only one predetermined antiviral drug-resistant mutation in the synthetic peptide, it has been shown that some antiviral drugs can induce more than one amino acid substitution in a viral protein. In cases where an antiviral drug induces more than one amino acid substitution (or addition or deletion) in a viral protein, a synthetic peptide may comprise more than one predetermined antiviral drug-resistant mutation. This is particularly preferred when two or more antiviral drug-resistant mutations appear in close proximity of each other. Close proximity in this context means that it is possible to make a synthetic peptide having a length of between 9 and 15 amino acid residues and comprising more than one predetermined antiviral drug-resistant mutation in a viral protein.

Synthetic peptides of the present invention are capable of inducing a cytotoxic T lymphocyte response specific for cells infected with the antiviral drug-resistant virus as described further below and in the Examples.

1.2.1. Predetermined Antiviral Drug-Resistant Mutations in HIV-1 Reverse Transcriptase The present invention provides for synthetic peptide having a length of between 9 and 15 amino acid residues and comprising a predetermined antiviral drug-resistant mutation in a viral protein.

The viral protein can be any viral protein identified in a virus causing a chronic viral infection and which is antiviral drug-resistant virus. Preferably, the viral protein is a viral protein identified in an antiviral drug-resistant virus selected from the group consisting of HIV-1, HIV-2, hepatitis B virus, hepatitis C virus and human herpesviruses. Human herpesviruses include herpes simplex-1, herpes simplex-2, varicella zoster virus, Epstein Barr virus, cytomegalovirus, human herpesvirus-6, and human herpesvirus-8 (also called Kaposi's sarcoma associated herpesvirus). In a preferred embodiment of the present invention, the virus is HIV-1.

There are there at least 175 HIV-1 drug resistance mutations, of which at least 88 occur in reverse transcriptase (RT), at least 52 in HIV-1 protease, at least 34 in HIV-1 envelope gene, and at least 1 in HIV-1 integrase (O'Meara et al. J Clin Microbiol 2001, 39(2):464-473).

In a preferred embodiment of the present invention, the viral protein is HIV-1 reverse transcriptase. A number of antiviral drug-resistant mutation in HIV-1 reverse transcriptase are identified in Table 1.

TABLE 1

A Number of Antiviral Drug-resistant Mutations in the Reverse Transcriptase of HIV-1

| Antiviral drug | Mutation | Reference |
| --- | --- | --- |
| zalcitabine (2',3'-dideoxycytidine [ddC] | Lys65Arg; Thr69Asp; Thr165Ile; Met184Val; Pro294Ser; | (1), (2), (14), (15), (31); (32), (35) |
| zidovudine (3'-azido-2',3'-dideoxythymidine; AZT) | Met41Leu; Ile50Val; Asp67Asn; Lys70Arg; Val108Ala; Ile135Thr; Ile135Val; Gln151Met; Leu210Trp; Thr215Tyr; Thr215Phe; Thr215Ser; Lys219Gln | (3), (6), (7), (8), (9), (12), (13), (24), (27), (28) |
| didanosine (2',3'-dideoxyinosine (ddI) | Ser68Gly; Leu74Val; Met184Val; Thr215Tyvr; Pro294Ser | (1), (3), (5), (14), (31), (32) |
| lamivudine [(−)2',3'-dideoxy-3'-thiacytidine; 3TC) | Glu44Asp; Glu44Ala; Lys65Arg; Val118Ile; Gln151Met; Met184Val; Met184Ile; Met184Ala | (4), (17), (18), (19), (27), (28), (31), (33); (35) |
| emtracitabine (beta-L-2',3'-dideoxy-5-fluoro-3'-thiacytidine (FTC) | Met184Val; Met184Ile | (36); (37) |
| (−) enantiomer of 2',3'-dideoxy-5-fluoro-3'-thiacytidine [(−)FTC] | Met184Val; Met184Ile | (4); (16), (36) |
| (−) enantiomer of 2',3'-dideoxy-3'-thiacytidine [(−)-BCH-189] | Met184Val; Met184Ile | (4) |
| stavudine (2',3'-didehydro-2',3'-dideoxythymidine; D4T) | Val75Thr | (10) |
| adefovir dipivoxil [bis(pivaloyloxymethyl)-ester prodrug], adefovir [9-(2-phosphonylmethoxyethyl)adenine] | Lys65Arg; Lys70Glu | (11) |
| Combination of nucleoside inhibitors | Ala62Val; Thr69Ser-Ser-Gly*; Thr69Ser-Thr-Gly*; Thr69Ser-Val-Gly*; Val75Ile; Phe77Leu; Lys103Asn; Phe116Tyr; Gln151Met; Met184Val; Gly333Glu | (19), (20), (21), (22), (28), (29), (30) |
| 2'-beta-Fluoro-2',3'-dideoxyadenosine (F-ddA) | Pro119Ser; Val179Asp; Leu214Phe | (23) |
| tetrahydroimidazo[4,5,1-jk][1,4]benzodiazepine-2(1H)-one and -thione (TIBO) derivatives (e.g., R82150) | Leu100Ile | (26) |
| nevirapine | Lys103Asn, Val106Ala; Val108Ile; Val118Ile; Gln151Met; Tyr181Cys; Tyr181Ile; Tyr188Cys; Tyr188His; Tyr188Leu; Gly190Ala; Gly190Cys; Gly190Glu; Gly190Gln; Gly190Ser; Gly190Thr | (27) |
| (S)-4-isopropoxycarbonyl-6-methoxy-3-(methylthiomethyl)-3,4-dihydroquinoxaline-2(1H)-thione (HBY097) | Leu74Val; Leu74Ile; Val75Leu; Val75Ile; Val179Asp; Gly190Glu; Gly190Gln | (34) |

In this table, antiviral drug refers either to the antiviral drug used for selection of drug-resistant virus or the virus has been shown to be resistant to this antiviral drug; *, represents a substitution of threonine at position 69 to serine, followed by the insertion of two amino acids as indicated; the drug-resistant mutation Met184Val is underlined. (1) Zhang et al., Animicrob Agents Chemother 1994, 38(2):282-287; (2) Fitzgibbon et al., Antimicrob Agents Chemother 1992, 36(1):153-157; (3) Eron et al., Antimicrob Agents Chemother 1993, 37(7):1480-1487; (4) Schinazi et al., Antimicrob Agents Chemother 1993, 37(4):875-881; (5) Martin et al., Proc Natl Acad Sci USA 1993, 90(13):6135-6139; (6) Gao et al., J Virol 1993, 66(1):12-19; (7) Kellam et al., Proc Natl Acad Sci USA 1992, 89(5):1934-1938; (8) Wahlberg et al., FASEB J 1992, 6:2843-2847; (9) Larder and Kemp, Science 1989, 246(4934):1155-1158; (10) Lacey and Larder, Antimicrob Agents Chemother 1994, 38(6):1428-32; (11) Mulato et al., Antimicrob Agents Chemother 1998, 42(7): 1620-1628; (12) Hooker et al., J Virol 1996, 70(11):8010-8018; (13) Kellam et al., J Gen Virol 1994, 75(Pt2):341-351; (14) Gao et al., Animicrob Agents Chemother 1993, 37(6): 1390-1392; (15) Gu et al., Animicrob Agents Chemother 1994, 38(2):275-281; (16) Harrer at al., J Infect Dis 1996, 173(2):476-479; (17) Schuurman et al., J Infect Dis 1995, 171(6):1411-1419; (18) Wainberg et al., AIDS 1995, 9(4): 351-357; (19) Wainberg et al., Science 1995, 271:1282-1284; (19) Schmit et al., J Infect Dis 1996, 174(5):962-968; (20) Iversen et al., J Virol 1996, 70(2):1086-1090; (21) Shafer et al., J Infect Dis 1995, 172(1):70-78; (22) Shirasaka et al., Proc Natl Acad Sci USA 1995, 92(6):2398-2402; (23) Tanaka et al., Antimicrob Agents Chemother 1997, 41(6): 1313-1318; (24) Kozal et al., J Acqui Immune Defic Syndr 1994, 7(8):832-838; (25) Brindeiro et al., Antimicrob Agents Chemother 1999, 43(7):1674-1680; (26) Mellors et al., Mol Pharmacol 1993, 43(1):11-16; (27) Re et al., Int J Antimicrob Agents 2003, 22(4):388-94; (28) Rey et al., J Acquir Immune Defic Syndr Hum Retrovirol 1998, 17(3):203-208; (29) Bulgheroni et al., J Clin Virol 2004 29(1):27-32; (30) Kemp et al., J Virol 1998, 72(6):5093-5098; (31) Rusconi et al., J Clin Virol 2000, 19(3):135-142; (32) Gu et al., J Virol 1992, 66(12):7128-35; (33) Boyer et al., J Virol 2001, 75(14):6321-6328; (34) Kleim et al., Proc Natl Acad Sci USA 1996, 93(1):34-38; (35) Gu et al., J Biol Chem 1994, 269(45):28118-28122; (36) Ray et al. Antiviral Res 2002, 56:189-205; (37) Faraj et al., 1994, Antimicrob Agents Chemother 38(10):2300-5;

In a preferred embodiment of the present invention, a synthetic peptide comprises a predetermined antiviral drug-resistant mutation in HIV-1 reverse transcriptase selected from the group consisting of Met41Leu, Glu44Asp, Glu44Ala, Ile50Val, Ala62Val, Lys65Arg, Asp67Asn, Ser68Gly, Thr69Asp, Thr69Ser-Ser-Gly, Thr69Ser-Thr-Gly, Thr69Ser-Val-Gly, Lys70Arg, Lys70Glu, Leu74Ile, Leu74Val, Val75Ile, Val75Leu, Val75Thr, Phe77Leu, Leu100Ile, Lys103Asn, Val106Ala, Val108Ala, Val108Ile, Phe116Tyr, Val118Ile, Pro119Ser, Ile135Thr, Ile135Val, Gln151Met, Thr165Ile, Val179Asp, Tyr181Cys, Tyr181Ile, Met184Ala, Met184Ile, Met184Val, Tyr188His, Tyr188Leu, Gly190Ala, Gly190Cys, Gly190Glu, Gly190Gln, Gly190Ser, Gly190Thr, Leu210Trp, Leu214Phe, Thr215Tyr, Thr215Phe, Thr215Ser, Lys219Gln, Pro294Ser, and Gly333Glu. Here and in other similar notations, the first amino acid residue denotes the amino acid residue present in the sequence of wild-type virus at the position indicated by the number and the following amino acid residue denotes the amino acid residue occurring in the viral protein of the drug-resistant virus. For example, Met184Val, indicates that in the wild-type reverse transcriptase of HIV-1, methionine occurs at position 184 and that this methionine is mutated to valine in the reverse transcriptase of the antiviral drug-resistant virus.

Preferred compositions of the present invention comprise an antiviral drug and a synthetic peptide comprising a predetermined antiviral drug-resistant mutation in a viral protein. Table 1 provides a number of predetermined antiviral drug-resistant mutations in HIV-1 reverse transcriptase that are observed upon administration of an antiviral drug. Thus, for example, when a composition of the present invention comprises the antiviral drug lamivudine (3TC), a preferred synthetic peptide may comprise one or more of the following predetermined antiviral drug-resistant mutations: Glu44Asp, Glu44Ala, Lys65Arg, Val118Ile, Gln151Met, Met184Val, Met184Ile, or Met184Ala. In another example, when a composition of the present invention comprises the antiviral drug zidovudine (AZT), a preferred synthetic peptide may comprise one or more of the following predetermined antiviral drug-resistant mutations: Met41Leu, Ile50Val, Asp67Asn, Lys70Arg, Val118Ala, Ile135Thr, Ile135Val, Gln151Met, Leu210Trp, Thr215Tyr, Thr215Phe, Thr215Ser, or Lys219Gln.

In a preferred embodiment of the present invention, the predetermined antiviral drug-resistant mutation comprises an amino acid substitution of methionine at position 184 of the HIV-1 reverse transcriptase. Preferably, the amino acid substitution is a substitution of methionine to valine. Also preferred is an amino acid substitution of methionine to isoleucine. Thus, in a preferred embodiment of the present invention, a synthetic peptide comprises the amino acid sequence VIYQYIDDL (SEQ ID NO:4) or VIYQYVDDL (SEQ ID NO:3).

In another preferred embodiment of the present invention, the predetermined antiviral drug-resistant mutation comprises an amino acid substitution of lysine at position 67 of the HIV-1 reverse transcriptase. Preferably, the amino acid substitution is a substitution of asparagine (D) to aspartate (N). This substitution has been shown to lead to AZT resistance. Thus, in a preferred embodiment of the present invention, a synthetic peptide comprises the D67N substitution in HIV-1 reverse transcriptase. Accordingly, this invention provides synthetic peptides having a length of between 9 and 15 amino acid residues, comprising the predetermined antiviral drug-resistant mutation D67N and at least six amino acid residues flanking this predetermined mutation that are identical to the amino acid sequence of the HIV-1 reverse transcriptase. Exemplary synthetic peptides include, but are not limited to peptides comprising the amino acid sequence VFAJKKKNSTKWRKL (SEQ ID NO:7), PVFAJKKKNSTKWRK (SEQ ID NO:8), or FAIKKK NSTKWRKLV (SEQ ID NO:9), wherein Ncorresponds to the D67N substitution.

In yet another preferred embodiment of the present invention, the predetermined antiviral drug-resistant mutation comprises an amino acid substitution of lysine at position 70 of the HIV-1 reverse transcriptase. Preferably, the amino acid substitution is a substitution of lysine (K) to arginine (R). This substitution has been shown to lead to AZT resistance. Thus, in a preferred embodiment of the present invention, a synthetic peptide comprises the K70R substitution in HIV-1 reverse transcriptase. Accordingly, this invention provides synthetic peptides having a length of between 9 and 15 amino acid residues, comprising the predetermined antiviral drug-resistant mutation K7OR and at least six amino acid residues flanking this predetermined mutation that are identical to the amino acid sequence of the HIV-1 reverse transcriptase. Exemplary synthetic peptides include, but are not limited to peptides comprising the amino acid sequence AIKKKDSTRWRKLVD (SEQ ID NO:10), IKKKDSTRWRKLVDF (SEQ ID NO:11) or KKKDST RWRKLVDFR (SEQ ID NO:12), wherein Rcorresponds to the K7OR substitution.

In a preferred embodiment of the present invention, a synthetic peptide comprises more than one predetermined antiviral drug-resistant mutation. This is particularly preferred when an antiviral drug induces more than one antiviral drug resistant mutation in a viral protein. Preferably, these antiviral drug-resistant mutations are in close proximity of each other. For example, the antiviral drug AZT leads to the antiviral drug-resistant mutations D67N and K70R (see above). Thus, in a preferred embodiment of the present invention, a synthetic peptide comprises the D67N and K70R substitutions in HIV-1 reverse transcriptase. Accordingly, this invention provides synthetic peptides having a length of between 9 and 15 amino acid residues, comprising the predetermined antiviral drug-resistant mutation K70R and at least six amino acid residues flanking this predetermined mutation that are identical to the amino acid sequence of the HIV-1 reverse transcriptase. Exemplary synthetic peptides include, but are not limited to peptides comprising the amino acid sequence VFAIKKKNSTRWRKL, FAIKKK NSTRWRKLV, AIKKKNSTRWRKLVD, or IKKKNST RWRKLVDF, wherein R corresponds to the K70R substitution and N corresponds to the D67N substitution.

Another example is the combination of the AZT-resistant mutations at positions 215 and 219 of the HIV-1 reverse transcriptase (see Table 1). AZT resistant mutations of HIV-1 RT often show a substitution of threonine (T) to tyrosine (Y) or phenylalanine (F) at position 215 and a substitution of lysine (K) to glutamine (Q) at position 219. Thus, a preferred synthetic peptide of the present invention comprises the predetermined antiviral drug-resistant mutations T215Y (or T215F) and K219Q. Other combinations will be obvious to one skilled in the art, particularly in consideration of the data provided in Tables 1 through 5.

1.2.2. Predetermined Antiviral Drug-Resistant Mutations in HIV-1 Protease

As HIV-1 virions replicate and are assembled within the cell, viral polyproteins are cleaved by a viral enzyme, HIV protease to generate gag matrix (p17), capsid (p24), and nucleopcapsid (p15) proteins, the pol RT and integrase enzymes and other viral proteins. This process is essential for normal viral maturation and the generation of infective viral particles. (Akhteruzzaman et al., Antiviral Research 1998, 39:1-23). Inhibition of this cleavage process leads to the accumulation of noninfectious, immature virus particles and impairs the spread of virus infection in cell culture (Kohl et al., Proc Natl Acad Sci USA 1988, 85:4686-4690).

In a preferred embodiment of the present invention, the viral protein is HIV-1 protease. A number of antiviral drug-resistant mutation in HIV-1 protease are identified in Table 2.

TABLE 2

A Number of Antiviral Drug-resistant Mutations in the HIV-1 Protease

| Antiviral drug | Mutation | Reference |
|---|---|---|
| Saquinavir | Gly48Val; Ile54Val; Leu90Met | (1), (2); (3), (4) |
| Ritonavir | Met46Ile; Leu63Pro; Ala71Val; Val82Phe; Ile84Val; | (1) |
| Indinavir | Leu10Ile; Leu10Val; Met46Ile; Met46Leu; Gly48Val; Ile54Val; Leu63Pro; Val82Ala; Ala71Val; Ala71Thr; Val82Ala; Val82Phe; Val82Thr; Ile84Val; Leu89Met; Leu89Pro; Leu90Met | (1), (7) |
| Nelfinavir | Asp30Asn; Glu35Asp; Met36Ile; Met46Ile; Leu63Pro; Ala71Thr; Ala71Val; Val77Ile; Ile84Val; Ile84Ala; Asn88Asp; Asn88Ser; Leu90Met | (1), (5) |
| Amprenavir | Leu10Phe; Met46Ile; Ile47Val; Ile50Val; Asp60Val; Ile84Val; | (1), (6) |
| Combination of two or more protease inhibitors | Leu10Phe; Gly16Glu; Val32Ile; Met46Ile; Gly48Val; Ile54Met; Ile54Ser; Ala71Val; Val77Ile; Val82Ile; Ile84Val; Leu90Met | (1) |

In this table, antiviral drug refers either to the antiviral drug used for selection of drug-resistant virus or the virus has been shown to be resistant to this antiviral drug. (1) Akhteruzzam et al., Antiviral Res 1998, 39:1-23; (2) Eberle et al., AIDS Res Hum Retroviruses 1995, 11:671-676); (3) Jacobsen et al., Antiviral Res 1996, 29(1):95-97; (4) Jacobsen et al., Virology 1995, 206(1):527-534; (5) Patick et al., Agents Chemother 1996, 40:292-297; (6) Partaledis et al., Agents Chemother 1995, 69:5228-5235; (7) Vasudevachari et al., Antimicrob Agents Chemother 1996, 40(11):2535-2541.

In a preferred embodiment of the present invention, a synthetic peptide comprises a predetermined antiviral drug-resistant mutation in HIV-1 protease selected from the group consisting of Leu10Ile, Leu10Val, Leu10Phe, Gly16Glu, Asp30Asn, Val32Ile, Glu35Asp, Met36Ile, Met46Ile, Met45Leu, Ile47Val, Gly48Val, Ile50Val, Ile54Met, Ile54Ser, Ile54Val, Asp60Val, Leu63Pro, Ala71Thr, Ala71Val, Val77Ile, Val82Ala, Val82Ile, Val82Phe, Val82Thr, Ile84Ala, Ile84Val, Asn88Asp, Asn88Ser, Leu89Met, Leu89Pro and Leu90Met.

Preferred compositions of the present invention comprise an antiviral drug and a synthetic peptide comprising a predetermined antiviral drug-resistant mutation HIV-1 protease. Table 2 provides a number of predetermined antiviral drug-resistant mutations in HIV-1 protease that are observed upon administration of an antiviral drug. Thus, for example, when a composition of the present invention comprises the antiviral drug indinavir, a preferred synthetic peptide may comprise one or more of the following predetermined antiviral drug-resistant mutations: Leu10Ile, Leu10Val, Met46Ile, Met46Leu, Gly48Val, Ile54Val, Leu63Pro, Val82Ala, Ala71Val, Ala71Thr, Val82Ala, Val82Phe, Val82Thr, Ile84Val, Leu89Met, Leu89Pro, or Leu90Met. In another example, when a composition of the present invention comprises the antiviral drug saquinavir a preferred synthetic peptide may comprise one or more of the following predetermined antiviral drug-resistant 1.2.3. Predetermined Antiviral Drug-Resistant Mutations in HBV Polymerase Hepatitis B virus (HBV) causes infectious disease and is closely associated with chronic hepatitis, liver failure and primary hepatocellular carcinoma. Therapy of chronic HBV infection with antiviral drugs frequently is associated with the emergence of viral resistance. HBV often develops resistance to lamivudine (3TC) through a very similar mechanism as HIV-1. Mutations leading to drug resistance are found, for example, in the HBV polymerase that is similar to the HIV-1 reverse transcriptase.

In a preferred embodiment of the present invention, the viral protein is HBV polymerase. A number of antiviral drug-resistant mutations in HBV polymerase are identified in Table 3.

TABLE 3

A Number of Antiviral Drug-resistant Mutations in the HBV Polymerase

| Antiviral drug | Mutation | Reference |
|---|---|---|
| lamivudine [(−)2',3'-dideoxy-3'-thiacytidine; 3TC) | Leu80Ile [Leu426Ile]; Leu80Val [Leu426Val]; Val173Leu; Leu180Met; Met204Ile [Met552Ile]; Met204Ser; Met204Val [Met552Val]; Val207Ile [Val555Ile]; | (1), (2), (3), (4), (5), (6) |
| entecavir (ETV) | Ile169Thr; Thr184Gly; Ser202Ile; Met250Val | (2) |
| famciclovir | Val173Leu; Met204Ile [Met552Ile]; Val207Ile [Val555Ile]; | (4), (6) |
| adefovir dipivoxil (ADV) | Asn236Thr | (8) |
| Combination of antiviral drugs | Ser78Thr; Ile169Thr; Val173Leu; Leu180Met; Thr184Ser; Thr184Gly; Ser202Ile; Met204Val; Met250Val; | (2) |
| Untreated | Met204Arg; Asp206Asn | (7) |

In this table, antiviral drug refers either to the antiviral drug used for selection of drug-resistant virus or the virus has been shown to be resistant to this antiviral drug. The drug-resistant mutation Met204Val is underlined. Sequences for reverse transcriptase of HBV, including mutated variants thereof, are accessible through GenBank accession numbers, for example, AAV68947, AAV68942, AAV68937, AAV68932, AAV65295, AAV65294, AAV65293, AAV33429, AAV3340, AAK19542, BAD73947, BAD74112. The RT domain of HBV polymerase is comprised of 344 amino acid residues (Delany et al., J Virol 2003, 77(21):11833-11841). While some of the GenBank sequences vary in length, they generally can be aligned by designating the methionine within the conserved YMDD motif of the nucleotide-binding site of the viral polymerase as M204. In some references, M204 corresponds to M552. (1) Lindstrom et al., J Clin Microbiol 2004, 42(10):4788-4795; (2) Tenney et al., Antimicrob Agents Chemother 2004, 48(9):3498-3507; (3) Walters et al., Animicrob Agents Chemother 2003, 47(6):1936-42; (4) Leon et al., Enferm Infecc Microbiol Clin 2004, 22(3):133-137; (5) Bozdayi et al., J Viral Hepat 2003, 10(4):256-265; (6) Delaney et al., J Virol 2003, 77(21):11833-11841; (7) Ohishi et al., J med Virol 2004, 72(4):558-565; (8) Villeneuve et al., J Hepatol 2003, 39(6):1085-1089; (9) Ogata et al., J Med Virol 1999, 59(3):270-276;

In a preferred embodiment of the present invention, a synthetic peptide comprises a predetermined antiviral drug-resistant mutation in HBV polymerase selected from the group consisting of consisting of Ser78Thr, Leu80Ile, Leu80Val, Ile169Thr, Val173Leu, Leu180Met, Thr184Gly, Thr184Ser, Ser202Ile, Met204Arg, Met204Ile, Met204Ser, Met204Val, Asp206Asn, Val207Ile, Asn236Thr and Met250Val.

Preferred compositions of the present invention comprise an antiviral drug and a synthetic peptide comprising a predetermined antiviral drug-resistant mutation in HBV polymerase. Table 3 provides a number of predetermined antiviral drug-resistant mutations in HBV polymerase that are observed upon administration of an antiviral drug. Thus, for example, when a composition of the present invention comprises the antiviral drug lamivudine (3TC), a preferred synthetic peptide may comprise one or more of the following predetermined antiviral drug-resistant mutations: Leu80Ile [Leu426Ile], Leu80Val [Leu426Val], Val173Leu, Leu180Met, Met204Ile [Met552Ile], Met204Ser, Met204Val [Met552Val], or Val207Ile [Val555Ile]. In another example, when a composition of the present invention comprises the antiviral drug famciclovir, a preferred synthetic peptide may comprise one or more of the following predetermined antiviral drug-resistant mutations: Val173Leu, Met 204Ile [Met552Ile], or Val207Ile [Val555Ile].

1.2.4. Predetermined Antiviral Drug-Resistant Mutations in HCV RNA-Dependent RNA Polymerase Hepatitis C Virus (HCV) infection is one of the major causes of chronic hepatitis, with frequent progression to liver cirrhosis and an elevated risk for the development of hepatocellular carcinoma. HCV represents the major etiological agent of posttransfusion and sporadic non-A, non-B hepatitis (Choo et al., Science 1989, 244:359-362).

In another embodiment of the present invention, the viral protein is HCV RNA-dependent RNA polymerase (NS5B). A number of antiviral drug-resistant mutations in HCV RNA-dependent RNA polymerase (NS5B) are identified in Table 4.

TABLE 4

A Number of Antiviral Drug-resistant Mutations in the HCV RNA-dependent RNA Polymerase (NS5B)

| Antiviral Drug | Mutation | Reference |
| --- | --- | --- |
| benzo-1,2,4-thiadiazine antiviral agent ($C_{21}H_{21}N_3O_4S$; compound 4) | Lys50Arg; Met71Val; Asn411Ser; Met414Thr; Val581Ala | (1), (2) |
| ribavirin | Phe415Tyr | (3) |

In this table, antiviral drug refers either to the antiviral drug used for selection of drug-resistant virus or the virus has been shown to be resistant to this antiviral drug. (1) Sarisky, J Antimicrob Chemother 2004, 54(1):14-16; (2) Nguyen et al., Antimicrob Agents Chemother 2003, 47(11):3525-3530; (3) Young et al., Hepatology 2003, 38(4):869-878.

In one embodiment of the present invention, a synthetic peptide comprises a predetermined antiviral drug-resistant mutation in HCV RNA-dependent RNA polymerase (NS5B) selected from the group consisting of Lys50Arg, Met71Val, Asn411Ser, Met414Thr, Phe415Tyr, or Val581Ala.

Preferred compositions of the present invention comprise an antiviral drug and a synthetic peptide comprising a predetermined antiviral drug-resistant mutation in HCV RNA-dependent RNA polymerase (NS5B). Table 4 provides a number of predetermined antiviral drug-resistant mutations in HCV RNA-dependent RNA polymerase (NS5B) that are observed upon administration of an antiviral drug. Thus, for example, when a composition of the present invention comprises the antiviral drug benzo-1,2,4-thiadiazine antiviral agent ($C_{21}H_{21}N_3O_4S$; compound 4), a preferred synthetic peptide may comprise one or more of the following predetermined antiviral drug-resistant mutations: Lys50Arg, Met71Val, Asn411Ser, Met414Thr, or Val581Ala. In another example, when a composition of the present invention comprises the antiviral drug ribavirin, a preferred synthetic peptide may comprise the following predetermined antiviral drug-resistant mutations: Phe415Tyr.

1.2.5. Predetermined Antiviral Drug-Resistant Mutations in HCV NS5A Protein

In another embodiment of the present invention, the viral protein is the HCV NS5A protein. Several antiviral drug-resistant mutations in the HCV NS5A protein have been identified (Table 5).

TABLE 5

Antiviral Drug-resistant Mutations in the HCV NS5A Protein

| Antiviral Drug | Mutation | Reference |
| --- | --- | --- |
| interferon-α with or without ribavirin | Leu2190Lys; Val2198Leu; Val2198Met; Val2198Glu; Thr2217Ala; Thr2217Val; Asn2218Asp; Asn2218Lys; Asn2218Ser; Asp2220Glu; Asp2223Glu; Glu2225Asp; Glu2228Gln; Glu2236Ala; Asn2248Asp; Ile2252Val; Ile2268Val; Arg2276Leu; Lys2277Arg; Ser2278Pro; Arg2280Lys; Arg2280Glu; Ala2282Thr; Pro2283Gln; Pro2283Arg; Val2287Ile; Leu2298Val; Leu2298Ile; Thr2300Pro; Thr2300Ala; Lys2302Asn; Lys2303Asn; Asp2305Gly; Pro2315Ala | (1) |
| interferon | Arg2218His; Ala2224Val; Thr2242Asn; Ile2252Val; Asp2257Val; Asp2257Glu; Leu2259ILe; Leu2259Val; Arg2260Gln; Arg2260Gly; Glu2262Val; Val2268Ile; Val2268Met; Pro2271Thr; Pro2271Ala; Lys2277Arg; Ser2278Pro; Ser2278Thr; | (2) |

TABLE 5-continued

Antiviral Drug-resistant Mutations in the HCV NS5A Protein

| Antiviral Drug | Mutation | Reference |
|---|---|---|
| | Lys2280Arg; Pro2283Arg; Pro2283Ser; Met2285Leu; Met2285Val; Pro2286Leu; Leu2298Met; Ser2300Thr; Asp2303Arg; Asp2305Glu; Val2307Ala; Val2307Ile; Pro2318Ser; Thr2319Ala; Lys2320Glu; ILe2324Val; Lys2330Arg; Arg2331Lys; Val2334Ile; Glu2356Gly; Thr2364Val; Thr2366Ser; Ala2367Gly; Pro2368Leu; Pro2368Ser; Pro2372Ala; Asp2374Asn; Asp2374Gly; Asp2375Asn; Asp2377Gly; Ala2378Lys; Ala2378Thr; Gly2379Glu; Val2382Ala; Val2382Gly; Glu2383Gly; Tyr2385Cys | |

In this table, antiviral drug refers either to the antiviral drug used for selection of drug-resistant virus or the virus has been shown to be resistant to this antiviral drug. (1) Sarrazin et al., J Infect 2000, 181(2):432-441, describing 16 strains of HCV isolated from patients without virologic response to antiviral treatment; (2) Duverlie et al., J Gen Virol 1998, 79(Pt6):1373-1381, describing sequences from 11 resistant strains from European HCV 1b isolates.

In one embodiment of the present invention, a synthetic peptide comprises a predetermined antiviral drug-resistant mutation in the HCV NS5A protein selected from the group consisting of consisting of Leu2190Lys, Val2198Leu, Val2198Met, Val2198Glu, Thr2217Ala, Thr2217Val, Asn2218Asp, Asn2218Lys, Asn2218Ser, Asp2220Glu, Asp2223Glu, Glu2225Asp, Glu2228Gln, Glu2236Ala, Asn2248Asp, Ile2252Val, Ile2268Val, Arg2276Leu, Lys2277Arg, Ser2278Pro, Arg2280Lys, Arg2280Glu, Ala2282Thr, Pro2283Gln, Pro2283Arg, Val2287Ile, Leu2298Val, Leu2298Ile, Thr2300Pro, Thr2300Ala, Lys2302Asn, Lys2303Asn, Asp2305Gly, and Pro2315Ala.

In one embodiment of the present invention, a synthetic peptide comprises a predetermined antiviral drug-resistant mutation in the HCV NS5A protein selected from the group consisting of consisting of Arg2218His, Ala2224Val, Thr2242Asn, Ile2252Val, Asp2257Val, Asp2257Glu, Leu2259ILe, Leu2259Val, Arg2260Gln, Arg2260Gly, Glu2262Val, Val2268Ile, Val2268Met, Pro2271Thr, Pro2271Ala, Lys2277Arg, Ser2278Pro, Ser2278Thr, Lys2280Arg, Pro2283Arg, Pro2283Ser, Met2285Leu, Met2285Val, Pro2286Leu, Leu2298Met, Ser2300Thr, Asp2303Arg, Asp2305Glu, Val2307Ala, Val2307Ile, Pro2318Ser, Thr2319Ala, Lys2320Glu, ILe2324Val, Lys2330Arg, Arg2331Lys, Val2334Ile, Glu2356Gly, Thr2364Val, Thr2366Ser, Ala2367Gly, Pro2368Leu, Pro2368Ser, Pro2372Ala, Asp2374Asn, Asp2374Gly, Asp2375Asn, Asp2377Gly, Ala2378Lys, Ala2378Thr, Gly2379Glu, Val2382Ala, Val2382Gly, Glu2383Gly, and Tyr2385Cys.

2. Peptides with Enhanced Immunostimulating Activity

The present invention provides peptides with enhanced immunostimulating activity. The immunostimulating peptides and nucleic acids encoding them, are useful as prognostic, therapeutic and diagnostic tools for the prevention and treatment of chronic viral infections, such as HIV-1 or HBV infections, particularly those infections resistant to antiviral drug therapies, such as lamivudine and other antiviral drugs.

2.1. Epitope Enhancement

While peptides can be used by themselves to stimulate an immune response, it has been noted that not all peptide epitopes lead to a strong immune response. However, in principle it should be possible to improve the immunogenicity of peptide epitopes by a process called "epitope enhancement," to develop a more highly effective vaccine, in particular an HIV-1 vaccine (Berzofsky et al., Immunol Rev 1999, 170:151; and Berzofsky et al., Nature Reviews Immunology 2001, 1:209).

One approach to enhance the immunogenicity of peptides is to improve the binding affinity of peptides for their Class I allele (Berzofsky et al., Nat Rev Immunol 2001, 1(3):209-19). Using epitope enhancement, we have developed synthetic peptides having utility as the active agents in the treatment and prevention of HIV-1 and hepatitis B virus infections (See Examples). Thus, in a preferred embodiment of the present invention, at least one amino acid residue of a synthetic peptide is substituted by an amino acid that serves as an epitope enhancement.

Thus, a synthetic peptide, which may comprise, for example one predetermined antiviral drug-resistant mutation, $P_M$, and 8 to 14 amino acid residues, flanking $P_M$ and identical to the amino acid sequence of a viral protein of the antiviral drug-resistant virus (thus having a length of between 9 and 15 amino acid residues) may be subject to various changes, such as substitutions, either conservative or non-conservative, within one or more of the 8 to 14 amino acid residues. Such changes provide for certain advantages in their use, such as improved HLA molecule binding. By conservative substitutions is meant replacing an amino acid residue with another that is biologically and/or chemically similar, e.g., one hydrophobic residue for another, or one polar residue for another. The substitutions include combinations such as (i) Gly, Ala; (ii) Val, Ile, Leu, Met; (iii) Asp, Glu; (iv) Asn, Gln; (v) Ser, Thr; (vi) Lys, Arg; and (vii) Phe, Tyr. By non-conservative amino acid substitution is meant replacing an amino acid residue with another that is biologically and/or chemically not similar, e.g., one hydrophobic residue for a polar residue. The effect of single amino acid substitutions may also be probed using D-amino acids. Such modifications may be made using well known peptide synthesis procedures, as described in, for example, Merrifield, Science 1986, 232:341-347; Barany and Merrifield, The Peptides, Gross and Meienhofer, eds. (New York, Academic Press), pp. 1-284 (1979); and Stewart and Young, Solid Phase Peptide Synthesis, (Rockford, Ill., Pierce), 2d Ed. (1984), incorporated by reference herein.

These substitutions may also comprise an amino acid analog or an amino acid mimetic. "Amino acid analog" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetic" refers to a chemical compound that has a structure that is different from the general chemical structure of an amino acid, but that function in a manner similar to a naturally occurring amino acid. In addition, amino acid analogs or amino acid mimetics can be incorporated at other positions of peptide conjugates or fusion proteins comprising a peptide or protein of the present invention.

Peptides with enhanced epitopes, compositions comprising them and methods employing them are particularly suitable for prognostic and therapeutic treatment of chronic viral infections, such as those caused by HIV-1 or HBV and in particular those caused by viral drug-resistant strains of HIV-1 or HBV. Epitope enhanced peptides of the invention may share the same amino acid sequence motif, such as a variant of a synthetic sequence motif derived from a sequence found in the reverse transcriptase of HIV-1 and a related sequence in the polymerase of HBV. This particular epitope enhanced peptide comprises the amino acid sequence VLYQYVDDV (SEQ ID NO:6), which is derived from the amino acid sequence VIYQYVDDL (SEQ ID NO:3) found in the reverse transcriptase of lamivudine-resistant HIV-1 (wherein the methionine at position 184 is substituted by valine, corresponding to V6 in VIYQYVDDL (SEQID NO:3)). By introducing two amino acid substitutions, 2I to 2L and 9L to 9V, the immune response stimulated by the peptide VLYQYVDDV (SEQ ID NO:6) is surprisingly increased over that stimulated by the native peptide (VIYQYVDDL; SEQ ID NO:3) in HLA-A2 transgenic mice (See Examples). Both peptides comprise the predetermined antiviral drug-resistant mutation, 6V, that is a substitution of methionine to valine. Thus, the amino acid substitutions at positions 2 and 9 to make the peptide VLYQYVDDV (SEQ ID NO:6), are the ones that increase the immunogenicity.

Accordingly, in a preferred embodiment of the present invention, an immunostimulating peptide comprises the amino acid sequence VLYQYVDDV (SEQ ID NO:6). This amino acid sequence motif to our knowledge is not found in nature.

The epitope enhancement with 2L9V also works in the context of another predetermined antiviral drug-resistant mutation identified in the RT of HIV-1, namely Met184Ile (see Examples). Thus, in another preferred embodiment of the present invention, an immunostimulating peptide comprises the amino acid sequence VLYQYIDDV (SEQ ID NO:5). This peptide comprises amino acid substitutions at positions 2 and 9 as described above and the predetermined antiviral drug-resistant mutation 6I, that is a substitution of methionine to isoleucine. Also, this amino acid sequence motif to our knowledge is not found in nature.

Further, we show that the epitope enhancement with 2L9V also works in the context of wild-type (6M) of the RT of HIV-1 epitope (VIYQYMDDL (SEQ ID NO:1); see Examples). Thus, in another embodiment of the present invention, the immunostimulating peptide comprises the amino acid sequence VLYQYMDDV (SEQ ID NO:23). This peptide comprises amino acid substitutions at positions 2 and 9 as described above and the wild-type methionine at position 6. Also, this amino acid sequence motif to our knowledge is not found in nature.

Other immunostimulating peptide sequences useful for composition and methods described herein can be derived without undue experimentation by (i) selecting a predetermined antiviral drug-resistant mutation, for example, one of those described in Tables 1 through 5 and (ii) performing epitope enhancement as described herein and by others (see Okazaki et al., J Immunol 2003, 171(5):2548-55; Sarobe et al., J Clin Invest 1998, 102:1239-1248; Ahlers et al., Proc Natl Acad Sci USA 1997, 94:10856-10861; Ahlers et al., J Clin Invest 2001, 108:1677-1685). Such immunostimulating peptides are considered to form distinct embodiments of the present invention.

Those skilled in the art of preparing pharmaceutical compositions will realize how to prepare the peptide and proteins described above for pharmaceutical use in compositions comprising pharmaceutically acceptable carriers.

2.2. Peptide Conjugates for Enhanced Immunostimulating Activity

Peptides of the present invention can be used by themselves to stimulate an immune response. They can also be used to prepare immunogenic conjugates in which a peptide of the present invention is conjugated to an agent that provokes an immune response using methods known in the art (See, for example, Good, Science 1987, 235:1059-1062; and Palker, J Imm 1989, 142:3612-3619).

Agents that can be conjugated to peptides to provoke an immune response include, but are not limited to, for example, toxoids such as diphtheria toxoid or tetanus toxoids, which are commonly recognized by the body (of immunized persons) and which elicit an immune response. Alternatively, a gene sequence encoding the peptide may be incorporated into a recombinant gene and expressed as part of a vector, for example, a recombinant virus such as vaccinia virus made by the method of Chakrabarti et al. (Nature 1986, 320:535-537).

A peptide of the present invention may also be incorporated into a larger peptide comprising additional epitopes, either other T cell epitopes or B cell epitopes. Alternatively, a peptide of the invention may be delivered to a host, preferably a patient, as part of a treatment regime including other immunostimulants. Thus, the peptide may be used as part of a multivalent vaccine that induces cytotoxic T cell responses to multiple epitopes of, for example, HIV-1, HBV, or either of these viruses and another virus. In addition, the multivalent vaccine peptide may include helper T cell epitopes and B cell epitopes of HIV-1, HBV or another virus, to effect induction of an antibody response as well as a cytotoxic T cell response. For example, one can attach a helper T cell epitope from HIV-1, such as those described in Cease et al. (Proc Natl Acad Sci USA 1987, 84:4249-4253), to provide T cell help for a CTL response. Also see Berzofsky et al. (J. Clin. Invest. 1991, 88:876-884) for construction of peptides encompassing multideterminant clusters of HIV envelope to induce in vitro T cell response in mice and humans of multiple MHC types; Hart et al. (Proc Natl Acad Sci USA 1991, 88:9448-9452) for priming of anti-HIV CD8+ cytotoxic T cells in vivo by carrier-free HIV synthetic peptides; and Hart et al. (J Immunol 1990, 145:2677-2685) for synthetic peptides containing T and B cell epitopes from HIV envelope gp120 inducing anti-HIV proliferative responses and high titers of neutralizing antibodies in rhesus monkeys.

Those skilled in the art of preparing pharmaceutical compositions will realize how to prepare the peptides conjugates described above for pharmaceutical use in composition comprising pharmaceutically acceptable carriers.

2.3. Fusion Proteins

In one preferred embodiment of the present invention, an immunostimulating peptide or protein comprises an amino acid sequence of the formula $X_1Y_1P_MY_2X_2$, wherein $P_M$ is a predetermined antiviral drug-resistant mutation, $Y_1$ is an amino acid sequence comprising from 2 to 12 amino acid residues identical to an amino acid sequence in a viral protein of an antiviral drug-resistant virus and is amino-terminal to $P_M$, wherein $Y_2$ is an amino acid sequence comprising from 2 to 12 amino acid residues identical to an amino acid sequence in a viral protein of an antiviral drug-resistant virus and is carboxy-terminal to $P_M$, wherein $X_1$ is an amino acid sequence of between 0 and 100 amino acid residues in length and is amino-terminal to $Y_1$; and wherein $X_2$ is an amino acid sequence of between 0 and 100 amino acid residues in length and is carboxy-terminal to $Y_2$. Further, $Y_1$ and $Y_2$ are amino acid sequences from the same viral protein. Thus, if $Y_1$ is an amino acid sequence identical to HIV-1 reverse transcriptase, then $Y_2$ is also an amino acid sequence identical to HIV-1 reverse transcriptase. In this embodiment, the combined length of the amino acid sequences of $Y_1$ and $Y_2$ is between 8 and 14 amino acid residues.

In a preferred embodiment, a peptide having an amino acid sequence of the formula $X_1Y_1P_MY_2X_2$ comprises the amino acid sequence VIYQYVDDL (SEQ ID NO:3) or VIYQYIDDL (SEQ ID NO:4). By way of example, in the peptide AAAVIYQYVDDLGGG (SEQ ID NO:25), AAA is $X_1$,VIYQY (SEQ ID NO:26) is $Y_1$, V is $P_M$, DDL is $Y_2$, and GGG is $X_2$.

In another embodiment at least one of the amino acid residues of $Y_1$ or $Y_2$ or both is substituted by another amino acid residue which serves as an epitope enhancement. Exemplary peptides of this embodiment comprise the amino acid sequence VLYQYVDDV (SEQ ID NO:6) or VLYQYIDDV (SEQ ID NO:5). By way of example, in the peptide AAAVLYQYVDDVGGG (SEQ ID NO:27), AAA is $X_1$, VLYQY (SEQ ID NO:28) is $Y_1$, wherein L is the substituted amino acid residue serving as an epitope enhancement, V is $P_M$, DDV is $Y_2$, wherein V is the substituted amino acid residue serving as an epitope enhancement, and GGG is $X_2$.

In another embodiment of the present invention, an immunostimulating peptide or protein comprises two predetermined antiviral drug-resistant mutations and an amino acid sequence of the formula $X_1Y_1P_{M1}Y_3P_{M2}Y_2X_2$, wherein $P_{M1}$ is a first predetermined antiviral drug-resistant mutation, wherein $P_{M2}$ is a second predetermined antiviral drug-resistant mutation, wherein $Y_1$ is an amino acid sequence comprising from 2 to 12 amino acid residues identical to an amino acid sequence in a viral protein of an antiviral drug-resistant virus and is amino-terminal to $P_{M1}$, wherein $Y_2$ is an amino acid sequence comprising from 2 to 12 amino acid residues identical to an amino acid sequence in a viral protein of an antiviral drug-resistant virus and is carboxy-terminal to $P_{M2}$, wherein $Y_3$ is an amino acid sequence comprising from 0 to 9 amino acid residues identical to an amino acid sequence in a viral protein of an antiviral drug-resistant virus and is between $P_{M1}$ and $P_{M2}$, wherein $X_1$ is an amino acid sequence of between 0 and 100 amino acid residues in length and is amino-terminal to $Y_1$; and wherein $X_2$ is an amino acid sequence of between 0 and 100 amino acid residues in length and is carboxy-terminal to $Y_2$. Further, in this embodiment, $Y_1$,$Y_2$ and $Y_3$ are amino acid sequences from the same viral protein. Thus, if $Y_1$ is an amino acid sequence identical to HIV-1 reverse transcriptase, then $Y_2$ and $Y_3$ are also amino acid sequences identical to HIV-1 reverse transcriptase. In this embodiment, the combined length of the amino acid sequences of $Y_1$,$Y_2$ and $Y_3$ is between 7 and 13 amino acid residues.

In a preferred embodiment, a peptide having an amino acid sequence of the formula $X_1Y_1P_{M1}Y_3P_{M2}Y_2X_2$ comprises the amino acid sequence VFAIKKKNSTRWRKL (SEQ ID NO:13), FAIKKKNSTRWRKLV (SEQ ID NO:14), AIKKKNSTRWRKLVD (SEQ ID NO:15), or IKKKNSTRWRKLVDF (SEQ ID NO:16), wherein R corresponds to the K70R substitution and N corresponds to the D67N substitution within HIV-1 RT (see above). By way of example, in the peptide AAAVFAIKKKNSTRWRKLGGG (SEQ ID NO:29), AAA is $X_1$, VFAIKKK (SEQ ID NO:30) is $Y_1$, N is $P_{M1}$, ST is $Y_3$, R is $P_{M2}$, WRKL (SEQ ID NO:31) is $Y_2$, and GGG is $X_2$.

In another embodiment at least one of the amino acid residues of $Y_1$, $Y_2$ or $Y_3$ is substituted by another amino acid residue which serves as an epitope enhancement.

Although the peptides of the invention will preferably be substantially free of contaminants, including naturally occurring host cell proteins and fragments thereof, in some embodiments the peptides can be synthetically conjugated to native fragments or particles, immunostimulating molecules and the like to form advantageous fusion molecules. "Fusion molecule" refers to any molecule formed through the structural linkage of a peptide of the present invention to one or more molecules, particularly macromolecules. In the context of the present invention other molecules that can be joined to peptides of the invention to form fusion molecules include sugars and polysaccharides, other peptides and proteins, lipids, and nucleotides and nucleic acids.

Both peptides and fusion molecules of the invention may be in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Other fusion molecules of the invention include glycoproteins, lipoproteins, nucleoproteins or other heterologous molecules comprising a peptide of the present invention, preferably a peptide having the sequence VLYQYVDDV (SEQ ID NO:6) or VLYQYIDDV (SEQ ID NO:5).

These fusion molecules may be produced by methods known to those of skill in the art and are typically designed to improve antigenicity or aid in the molecules delivery to a host, preferably a patient. Thus the peptides and fusion molecules of the present invention may be modified as necessary to provide certain desired attributes, e.g., improved pharmacological characteristics, while increasing or at least retaining substantially all of the biological activity of the unmodified peptide to bind the desired MHC molecule and induce a desirable CTL response.

Those skilled in the art of preparing pharmaceutical compositions will realize how to prepare the fusion proteins described above for pharmaceutical use in composition comprising pharmaceutically acceptable carriers.

2.4. General Procedure for Producing Peptides

The present invention provides synthetic peptides. These peptides may be synthesized by any of the techniques that are known to those skilled in the peptide art, including using recombinant DNA techniques and isolated natural sources, such as whole viruses or tumors, which express proteins that include a segment having the amino acid sequence of the present invention. Preferably the peptides of the present invention are prepared using a synthetic chemistry technique.

Synthetic chemistry techniques, such as a solid-phase Merrifield-type synthesis, are preferred for reasons of purity, antigenic specificity, freedom from undesired side products, ease of production and the like. Summaries of the many techniques available can be found in J. M. Steward & J. D. Young, SOLID PHASE PEPTIDE SYNTHESIS, W.H. Freeman Co., San Francisco, (1969); M. Bodanszky et al., PEPTIDE SYNTHESIS, John Wiley & Sons, Second Edition, (1976); and J. Meienhofer, HORMONAL PROTEINS AND PEPTIDES, Vol. 2, p. 46, Academic Press, New York (1983) for solid phase peptide synthesis, and E. Schroder & K. Kubke, 1 THE PEPTIDES, Academic Press, New York (1965) for classical solution synthesis, each being hereby incorporated herein by reference. Appropriate protective groups usable in such synthesis are described in the above texts and in J. F. W. McOmie, PROTECTIVE GROUPS IN ORGANIC CHEMISTRY, Plenum Press, New York (1973), the entire disclosure of which is also incorporated herein by reference. Simplified methods for solid phase synthesis of peptides on a small scale also are known. See for example, Houghten, Proc Natl Acad Sci U.S.A. 1985, 82:5131-5135; and Houghton et al., European Patent Application 88310922 (1988).

Alternatively, recombinant DNA technology may be employed wherein a nucleotide sequence that encodes an immunogenic peptide of interest is inserted into an expression vector, transformed or transfected into an appropriate host cell and cultivated under conditions suitable for expression. These procedures are generally known in the art, as described generally in Sambrook et al., Molecular Cloning, A Laboratory Manual, Cold Spring Harbor Press, Cold Spring Harbor, N.Y. (1982), which is incorporated herein by reference. "Vector" refers to any type of genetic construct containing a nucleic acid capable of being transcribed in a cell. Vectors used for the amplification of nucleotide sequences (both coding and non-coding) are also encompassed by the definition. In addition to the coding sequence, vectors will generally include restriction enzyme cleavage sites and the other initial, terminal and intermediate DNA sequences that are usually employed in vectors to facilitate their construction and use. The expression vector can be part of a plasmid, virus, or nucleic acid fragment. "Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-o-methyl ribonucleotides and peptide-nucleic acids (PNAs).

Coding sequences for the immunostimulating peptides and proteins of the present invention may be synthesized by chemical techniques, for example, the phosphotriester method of Matteucci et al. (J Am Chem Soc 1981, 103: 3185). The term "coding sequence", in relation to nucleic acid sequences, refers to a plurality of contiguous sets of three nucleotides, termed codons, each codon corresponding to an amino acid as translated by biochemical factors according to the universal genetic code, the entire sequence coding for an expressed protein, or an antisense strand that inhibits expression of a protein. A "genetic coding sequence" is a coding sequence where the contiguous codons are intermittently interrupted by non-coding intervening sequences, or "introns." During mRNA processing intron sequences are removed, restoring the contiguous codon sequence encoding the protein or anti-sense strand.

Any modification within a DNA or RNA sequence can be made simply by substituting the appropriate bases for those encoding the desired amino acid sequence. The coding sequence can then be provided with appropriate linkers and ligated into expression vectors commonly available in the art, and the vectors used to transform suitable hosts to produce the immunostimulating peptide or protein. A number of such vectors and suitable host systems are commercially available. For expression, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences as known to the skilled artisan.

2.5. Modification of Peptides

The peptides of the invention may also be modified by extending their amino acid sequence, e.g., by the addition of amino acids to their N or C terminus as described herein (see above).

The peptides or fusion molecules of the invention can also be modified by altering the order or composition of certain amino acid residues, it being readily appreciated that the core immunostimulating sequence (i.e., the amino acid sequence of the peptide comprising the predetermined antiviral drug-resistant mutation and the at least six amino acids flanking the predetermined antiviral drug-resistant mutation that are identical to the amino acid sequence of the viral protein of the antiviral drug-resistant virus; for example VIYQYVDDL (SEQ ID NO:3), or the epitope enhanced version thereof, VLYQYVDDV (SEQ ID NO:6)), may generally not be altered without an adverse effect on biological activity.

The noncritical amino acids need not be limited to those naturally occurring in proteins, such as L-α-amino acids, or their D-isomers, but may include non-natural amino acids as well, such as β-γ-δ-amino acids, as well as many derivatives of L-α-amino acids. Modifications of fusion molecules with various amino acid mimetics or unnatural amino acids are particularly useful in increasing the stability of the peptide in vivo. Stability can be assayed in a number of ways. For example, peptidases and various biological media, such as human plasma and serum, have been used to test stability (Verhoef et al., Eur J Drug Metab Pharmacokin 1986, 11:291-302). Half life of the peptides of the present invention is conveniently determined using a 25% human serum (v/v) assay. The protocol is generally as follows. Pooled human serum (Type AB, non-heat inactivated) is de-lipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

Peptides of the present invention may be modified to provide desired attributes other than improved serum half life. For example, the ability of the peptides to induce CTL activity can be enhanced by linkage to a sequence that contains at least one epitope capable of inducing a T helper cell response (see also above). Particularly preferred immunostimulating peptides/T helper conjugates can be linked together by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two amino acid residues, more usually three to six amino acid residues. Alternatively, the immunostimulating peptide may be linked to the T helper peptide without a spacer.

Linkage to a T helper peptide may be at the amino- or carboxy-terminus of the immunostimulating peptide. The amino-terminus (N-terminus) of either the immunostimulating peptide or the T helper peptide may be acylated. The carboxy-terminus (C-terminus) of either the immunostimulating peptide or the T helper peptide may also be modified, e.g., by amidation, esterification or reduction of the carboxyl group. Methods for performing these modifications are well known to those of skill in the art.

Thus, in a preferred embodiment of the present invention, an immunostimulating peptide comprises an acetylated N-terminus. In another embodiment, an immunostimulating peptide comprises a modification at the C-terminus. The modification can be amidation, esterification, or reduction of a C-terminal amino acid carboxyl group. Immunostimulating peptides having modifications at both the N- and C-termini are also contemplated, as are peptides with modified amino acid side chains, as described herein.

3. Medicaments and Vaccines

Peptides of the present invention preferably produce high avidity CTL. This property is particularly attractive in peptides considered for use as medicaments and therapeutic vaccines as high avidity CTL have been found to be critical in clearance of virus infection (Alexander-Miller et al., Proc Natl Acad Sci U.S.A. 1996, 93:410; and Gallimore et al., J Exp Med 1998, 187:1647). Peptides and nucleic acids of the present invention are applicable to all forms of vaccine, e.g., peptide, DNA, recombinant viral or bacterial vector, or live attenuated virus.

Peptides of the present invention and pharmaceutical and vaccine compositions thereof are useful for administration to mammals, particularly humans, to treat and/or prevent viral infection, particularly infection by HIV-1 or HBV. Examples of diseases treatable in an individual using the immunostimulating peptides of the present invention include, but are not limited to, for example asymptomatic seropositivity, AIDS-related complex (ARC) or acquired immunodeficiency syndrome (AIDS) for HIV-1, and jaundice or liver failure for HBV or HCV.

3.1. Medicaments Comprising an Antiviral Drug and a Synthetic Peptide with a Predetermined Antiviral Drug-Resistant Mutation It is an objective of the present invention to provide medicaments useful for lowering viral load in a host, preferably a patient, and methods for making the medicaments.

In a preferred embodiment of the present invention, a medicament comprises (i) a synthetic peptide comprising a predetermined antiviral drug-resistant mutation, wherein the synthetic peptide comprises an amino acid sequence of between 9 and 15 amino acid residues and (ii) an antiviral drug in an amount effective to restrict intracellular multiplication of a wild-type virus, but substantially less effective in restricting intracellular multiplication of an antiviral drug-resistant virus, wherein the antiviral drug-resistant virus differs from the wild-type virus by at least one substitution, insertion or deletion of one amino acid residue in a viral protein of the wild-type virus. All predetermined anti-viral drug-resistant mutations, viruses, viral proteins, and peptide epitope enhancement described and referred to herein are useful for making and using the medicaments of the present invention.

In a preferred embodiment of the present invention, a medicament comprises a synthetic peptide comprising the amino acid sequence VIYQYVDDL (SEQ ID NO:3) or VIYQYIDDL (SEQ ID NO:4).

In a more preferred embodiment of the present invention, a medicament is provided, wherein at least one amino acid residue of the synthetic peptide serves as an epitope enhancement. In a particularly preferred embodiment, the synthetic peptide comprises the amino acid sequence VLYQYVDDV (SEQ ID NO:6) or VLYQYIDDV (SEQ ID NO:5).

The medicaments of the present invention may comprise any of the immunostimulating peptides of the invention and a pharmaceutically acceptable carrier as described herein. Further contemplated herein are methods for using the compositions of the present invention in the preparation of a medicament.

3.2. Medicament Comprising a Dendritic Cell Displaying an Immunostimulating Peptide Peptides and proteins of the present invention may also be used to pulse autologous dendritic cells as a means of immunization against the peptide or protein, using techniques well-known to those of skill in the art.

Thus, another aspect of the invention is a medicament comprising an immunostimulating peptide pulsed or transduced into dendritic cells. Dendritic cells treated in this manner may display the peptide at their cell surface, thereby stimulating an immune response in a host receiving the modified dendritic cell. Alternatively, the dendritic cell may be incubated in a culture medium containing the peptide of the invention; here the peptide becomes incorporated into or on to the surface of the dendritic cell. Medicaments comprising the immunostimulating peptide noted above and a pharmaceutically acceptable carrier are also contemplated.

These latter medicaments my also contain an immunostimulating agent or adjuvant, to aid in eliciting an immune response.

3.3. Formulations and Pharmaceutically Acceptable Carriers

The formulation should suit the mode of administration. In some embodiments of the invention it may, for example, be desirable to include in the pharmaceutical compositions (i.e., medicaments or vaccines) of the invention at least one component, such as an immunostimulating agent, which assists in priming a CTL response. Thus, in one preferred embodiment of the present invention, a medicament comprises an immunostimulating agent. In a particularly preferred embodiment of the present invention, the immunostimulating agent comprises a protein to which a host or patient is immune and which stimulates a cytotoxic T lymphocyte response.

Lipids have been identified as agents capable of assisting the priming CTL in vivo against viral antigens. For example, palmitic acid residues can be attached to the alpha and epsilon amino groups of a Lys residue and then linked, e.g., via one or more linking residues such as Gly, Gly-Gly-, Ser, Ser-Ser, or the like, to an immunostimulating peptide. The lipidated peptide can then be injected directly in a micellar form, incorporated into a liposome or emulsified in an adjuvant, e.g., incomplete Freund's adjuvant. A particularly effective immunostimulating agent comprises palmitic acid attached to alpha and epsilon amino groups of Lys, which is attached via linkage, e.g., Ser-Ser, to the amino terminus of the immunostimulating peptide.

As another example of lipid priming of CTL responses, *E. coli* lipoproteins, such as tripalmitoyl-S-glycerylcysteinly-seryl-serine ($P_3$ CSS) can be used to prime virus specific CTL when covalently attached to an appropriate peptide. See, for example, Deres et al. (Nature 1989, 342:561-564; incorporated herein by reference). Immunostimulating peptides of the invention can be coupled to $P_3$ CSS, for example, and the lipopeptide administered to an individual to specifically prime a CTL response to the target antigen. Further, as the induction of neutralizing antibodies can also be primed with $P_3$ CSS conjugated to a peptide that displays an appropriate epitope, the two compositions can be combined to more effectively elicit both humoral and cell-mediated responses to infection.

Further, contemplated herein as immunostimulating agents are helper peptides, helper proteins, cytokines and other factors including, but not limited to, for example granulocyte-macrophage colony stimulating factor (GM-CSF), IL-15, and IL-12.

Pharmaceutical compositions of this invention, such as medicaments and vaccines, typically comprise a pharmaceutically acceptable carrier. Such a carrier can be a sterile liquid, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

A pharmaceutical composition of the present invention, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides.

An oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such pharmaceutical compositions will contain a therapeutically effective amount of the peptides of the present invention, preferably in purified form, together with a suitable amount of carrier so as to provide the form for proper administration to a host.

For generating a long term memory response, vaccination with a CTL epitope alone may not be sufficient. Thus, in a preferred embodiment of the present invention, to augment the response, a CTL peptide of the present invention is administered as an emulsion together with an oil-based adjuvant. Preferred oil-based adjuvants are Montanide® ISA 51 or Montanide® ISA 51 VG (Aucouturier et al., Expert Rev Vaccines 2002, 1 (1): 111-8). Montanide® ISA 51 or Montanide® ISA 51 VG, which are similar to incomplete Freund's adjuvant, are oil-based adjuvants composed of a highly refined mannide oleate (Montanide 80), a surfactant, in a mineral oil solution (Drakeol 6VR). Montanide® ISA 51 and Montanide® ISA 51 VG differ in that Montanide® ISA 51 VG uses a vegetable rather than an animal source for the oleic acid component. The mannide monooleate is synthesized from raw materials of vegetable origin. Montanide® ISA 51 or Montanide® ISA 51 VG, when mixed with an aqueous solution, form a stable water-in-oil emulsion. Montanide® ISA 51 or Montanide® ISA 51 VG have been used safely when vaccinating with peptides as well as in conjunction with cytokines (see, e.g., Carr et al., J Clin Oncol 2003, 21(6):1015-21; Slingluff et al., Clin Cancer Res 2001, 7(10):3012-24; Pinto et al., Aids 1999, 13(15):2003-12; Gonzalez et al., Ann Oncol 2003, 14(3): 461-6; Carr et al., Melanoma Res 2001, 11(3):219-27; Yamshchikov et al., Int J Cancer 2001, 92(5):703-11). Comparative analysis of the chemical compositions of the animal-grade formulation (Montanide® ISA 51) and the vegetable-grade formulation (Montanide® ISA 51 VG) oleic acid sources shows a final product with similar chemical and applicative properties (e.g., emulsion stability and viscosity). Montanide® ISA 51 VG is manufactured by, e.g., Seppic, Inc.

Optionally a stimulatory cytokine is administered with a CTL peptide of the present invention. Stimulatory cytokines have been utilized as an adjuvant for vaccines in numerous animal models. A preferred cytokine is GM-CSF/sargramostim. GM-CSF may either be coadministered with a CTL peptide of the present invention or alternatively administered shortly after vaccination with a CTL peptide. In another embodiment, GM-CSF is administered immediately after each vaccination with a CTL peptide of the present invention and for the following three days (days 1 to 4). The amount of GM-CSF administered may be in the range of about 5 µg to 1,000 µg, preferably in the range of about 50 µg to 500 µg, more preferably in the range of about 200 µg to 400 µg. A preferred amount of GM-CSF administered is about 250 µg.

The coadministration of a cytokine such as GM-CSF/sargramostim may enhance vaccination by changing the character and number of antigen presenting cells locally presenting the peptide. It may also alter the pathway, which the CTL peptide is being presented. GM-CSF has several immunoregulatory effects while producing an inflammatory response at the site of injection. It upregulates Class II MHC expression on macrophages, enhances dendritic cell maturation, simulates migration of dendritic cells. In vitro, GM-CSF has been utilized to improve immune response in mouse models. In vivo, it has been shown that GM-CSF/sargramostim increases CD4 and CD8 cells in a delayed type hypersensitivity response to peptide after vaccination (Jager et al., Int J Cancer 1996, 67(1):54-62). Also, injection of GM-CSF into vaccination sites was found to enhance a peptide-specific immune responses, including peptide-induced gamma interferon production, in melanoma patients immunized with a peptide melanoma vaccine in incomplete Freund's adjuvant (IFA) (Weber et al., Cancer 2003, 97(1): 186-200). In the Weber study study, GM-CSF was injected into the peptide vaccine site just after the peptide vaccination and then for an additional 4 days. An identical schedule of GM-CSF administration can be applied to a vaccination regimen comprising a CTL peptide of the present invention.

3.4. Administration of Pharmaceutical Compositions

Typically the pharmaceutical compositions of the invention are administered in an amount effective to induce an immune response capable of preventing a chronic viral infection or reducing viral load in a host, preferably a patient. In one aspect of the present invention, the medicaments are designed to treat or prevent infection by HIV-1, HBV or another virus, preferably for the treatment of viral strains resistant to drugs, such as lamivudine.

Peptides, medicaments and vaccines of the present invention are administered to a host. Most preferably, peptides, medicaments or vaccines of the present invention are administered to a human subject in need of such peptide, medicament or vaccine. In a preferred embodiment, the human subject is a patient. Most preferred, the peptides, medicaments or vaccines are administered to a patient who has been diagnosed of having a chronic viral infection.

Pharmaceutical compositions of the immunostimulating peptides of the invention can be administered to an individual already suffering from indications of the presence of the HIV-1, HBV or an other virus. Those individuals in the incubation phase or the acute phase of infection can be treated with the immunostimulating peptides or pharmaceutical compositions separately or in conjunction with other treatments, as appropriate.

In therapeutic applications, a pharmaceutical composition is administered to a host, preferably a patient, in an amount effective and sufficient to elicit an immune response, preferably a CTL response to the virus and cure, or at least partially arrest symptoms and/or complications associated with a chronic viral infection. An amount adequate to accomplish this is defined as "therapeutically effective dose." Amounts effective for this use will depend on, e.g., the peptide and/or protein composition, the manner of administration, the stage and severity of the disease being treated, the weight and general state of health of the individual, and the judgment of the prescribing physician, but generally range for the initial immunization (that is for therapeutic or prophylactic administration) from about 0.001 to about 10 mg/kg, more preferably about 0.01 to about 2 mg/kg, most preferably about 0.01 to 1 mg/kg peptide, followed by boosting dosages of from about 0.001 to about 2 mg/kg, more preferably about 0.01 to about 1 mg/kg peptide pursuant to a boosting regimen over weeks to months, depending upon the host's, preferably a patient's, response and condition determined by measuring specific CTL activity in the host's blood as described previously and in the examples that follow.

For therapeutic use, administration can begin as early as the first evidence or sign of viral infection is observed or even the time of first contact with the virus. This can be followed by boosting doses until at least symptoms are substantially abated and for a period thereafter. Loading doses followed by boosting doses may be required. Alternatively, immunization for a limited amount of time could be utilized. The immunization can be done before administration of antiviral drugs, such as lamivudine, after such therapy has been initiated, or during a break in the therapy.

Treatment of an infected individual with the compositions of the invention may hasten resolution of the infection in acutely infected individuals. For those individuals susceptible (or predisposed) to developing chronic viral infection the compositions are particularly useful in methods for preventing the infection. Where susceptible individuals are identified prior to or during infection the composition can be targeted to them, minimizing need for administration to a larger population.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration comprising a solution of the immunostimulating peptide dissolved or suspended in a pharmaceutically acceptable carrier, preferably an aqueous carrier. A variety of aqueous carriers may be used, e.g., water, buffered water, 0.9% saline, 0.3% glycine, hyaluronic acid and the like (see also above).

These compositions may be sterilized by conventional, well-known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of immunostimulating peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

Both peptides and the nucleic acids encoding them of the invention may also be administered via liposomes. Liposomes are useful in increasing the half-life of the peptides. Liposomes include emulsions, foams, micelles, insoluble monolayers, liquid crystals, phospholipid dispersions, lamellar layers and the like. In liposome preparations the peptide to be delivered may be incorporated as part of a liposome, alone or in conjunction with a molecule that binds to, e.g., a receptor prevalent among lymphoid cells, such as monoclonal antibodies that bind to the CD45 antigen, or with other therapeutic or immunogenic compositions. Thus, liposomes filled with a desired peptide of the invention can be directed to the site of lymphoid cells, where the liposomes then deliver the therapeutic/immunostimulating peptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, for example, Szoka et al., Ann Rev Biophys Bioeng 1980, 9:467, U.S. Pat. Nos. 4,235,871, 4,501,728, 4,837,028, and 5,019,369, incorporated herein by reference.

For targeting to immune cells, a ligand to be incorporated into the liposome can include, e.g., antibodies or fragments thereof specific for cell surface determinants of the desired immune system cells. A liposome suspension containing an immunostimulating peptide may be administered intravenously, locally, topically, etc. in a dose which varies according to, inter alia, the manner of administration, the peptide being delivered, and the stage of the disease being treated.

For solid compositions, conventional nontoxic solid carriers may be used including, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed carriers, such as those carriers previously listed, and generally about 10% to about 95% of active ingredient, that is, one or more peptides of the invention, and more preferably at a concentration of about 25% to about 75%.

For aerosol administration, the immunogenic peptides are preferably supplied in finely divided form along with a surfactant and propellant. Typical percentages of peptides are 0.01%-20% by weight, preferably 1%-10%. The surfactant must be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

Another aspect the present invention is directed to vaccines that contain as an active ingredient an immunogenically effective amount of an immunostimulating peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or CTLs that react with different antigenic determinants of, for example, the HIV-1 virus.

Useful carriers are well known in the art, and include, e.g., thyroglobulin, albumins such as bovine serum albumin, tetanus toxoid, polyamino acids such as poly (lysine: glutamic acid), HBV core protein, HBV recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. As mentioned above, CTL responses can be primed by conjugating peptides of the invention to lipids, such as $P_3$ CSS. Upon immunization with a peptide composition as described herein, via injection, aerosol, oral, transdermal or other route, the immune system of the host responds to the vaccine by producing large amounts of CTLs specific for the desired antigen, and the host becomes at least partially immune to later infection, or resistant to developing chronic infection.

In some instances it may be desirable to combine the peptide vaccines of the present invention with vaccines inducing neutralizing antibody responses to HIV-1 or HBV, particularly to viral envelope antigens of the respective peptides.

Immunostimulating peptides may also be used to elicit CTL ex vivo, as well. The resulting CTL can be used to treat hosts, preferably patients, that do not respond to other conventional forms of therapy, or will not respond to a peptide vaccine approach of therapy. See, for example, U.S. Pat. No. 6,037,135 for methods of performing ex vivo CTL therapy. Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated $CD8^+$ cells via intravenous infusion is appropriate.

Peptides, medicaments or vaccines of then present invention may also be administered in conjunction with chemotherapy (e.g., treatment with adriamycin, bleomycin, vincristine, vinblastine, doxorubicin, and/or paclitaxel (Taxol)) or other therapies known in the art.

3.5. Live Vaccines

For therapeutic or immunization purposes, the peptides of the present invention may also be expressed by attenuated viral hosts, such as vaccinia or fowl pox. This approach involves the use of the vaccinia or fowl pox virus as a vector to express nucleotide sequences that encode the peptide of the invention. Upon introduction into an infected or uninfected host, the recombinant virus expresses the immunogenic peptide, and thereby elicits a host CTL response. Vaccinia vectors and methods useful in immunization protocols are described in, for example, U.S. Pat. No. 4,722,848, incorporated herein by reference. Another vector is BCG (Bacille Calmette Guerin). BCG vectors are described in Stover et al. (Nature 1991, 351:456-460). A wide variety of other vectors useful for therapeutic administration or immunization of the peptides of the invention, e.g., *Salmonella typhi* vectors and the like, will be apparent to those skilled in the art from the description herein.

3.6. Gene Therapy

Another aspect of the invention is a nucleic acid-based medicament comprising a vector including a nucleic acid comprising a nucleotide sequence encoding an immunostimulating peptide.

In the context of reverse transcriptase of HIV-1, a nucleotide sequence preferable preferably encodes a peptide having the amino acid sequence VIYQYVDDL (SEQ ID NO:3), VIYQYIDDL (SEQ ID NO:4), VLYQYVDDV (SEQ ID NO:6), or VLYQYIDDV (SEQ ID NO:5). Introducing these nucleotide sequences into a subject results in expression of the nucleic acid, which induces an immune response in the subject directed against an epitope of the peptide encoded by the nucleic acid. In some embodiments the vector is from a virus.

Delivery into a host, preferably a patient, of nucleic acids encoding peptides and proteins of the present invention may be either direct, in which case the host is directly exposed to the nucleic acid or nucleic acid-carrying vectors, or indirect, in which case cells are first transformed with the nucleic acids in vitro, then transplanted into the host. These two approaches are known, respectively, as in vivo or ex vivo gene therapy.

For example, the nucleic acid sequences may be directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated viral or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J Biol Chem 1987, 262:4429-4432) (which can be used to target cell types specifically expressing the receptors), etc.

Nucleic acid-ligand complexes can be formed in which the ligand comprises a fusogenic viral peptide to disrupt endosomes, allowing the nucleic acid to avoid lysosomal degradation. Further, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc Natl Acad Sci USA 1989, 86:8932-8935; Zijlstra et al., Nature 1989, 342:435-438).

Nucleic acids of the present invention may also serve as effective vaccines, by introducing them into suitable cells where they will be expressed and either secreted, or displayed on the cell surface of the transformed cell. For example nucleic acids encoding peptides and proteins of the present invention may be used to transduce dendritic cells, which in turn can be used as vaccines for immunization.

Other modes of gene therapy are also contemplated by the present invention. For general reviews of the methods of gene therapy, see Goldspiel et al., Clinical Pharmacy 1993, 12:488-505; Wu and Wu, Biotherapy 1991, 3:87-95; Tolstoshev, Ann Rev Pharmacol Toxicol 1993, 32:573-596; Mulligan, Science 1993, 260:926-932; and Morgan and Anderson, Ann Rev Biochem 1993, 62:191-217; May, TIBTECH 1993, 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

4. Methods of Using the Compositions of the Invention

The compositions of the invention are effective at inhibiting viral replication and/or viral infection of cells in vitro or in vivo, lowering viral load and/or treating or preventing disorders associated with chronic viral infections. Further, the compositions of the present invention are useful for destroying cells infected with an antiviral drug-resistant virus, for providing an immune counter-selective pressure to prevent or suppress a viral escape mutation during antiviral therapy and for eradicating a viral escape mutant virus.

4.1. Method for Lowering Viral Load

Typically, replication of the HIV virus is measured by plasma RNA viral load. In untreated patients, it is estimated that 10 billion virions are produced daily. Thus, in a preferred embodiment of the present invention, a method for lowering viral load of a virus, wherein the virus causes a chronic viral infection and is resistant to an antiviral drug, is provided. The method comprises the step of administering to a host, preferably a patient, a medicament, the medicament comprising (i) the antiviral drug in an amount effective to restrict intracellular multiplication of the virus, wherein the antiviral drug is capable of selecting for a predetermined antiviral drug-resistant mutation in a viral protein, thereby creating an antiviral drug-resistant virus; and (ii) a synthetic peptide having a length of between 9 and 15 amino acid residues, the synthetic peptide comprising (1) the predetermined antiviral drug-resistant mutation in the viral protein; and (2) at least six amino acid residues flanking the predetermined antiviral drug-resistant mutation that are identical to the amino acid sequence of the viral protein of the antiviral drug-resistant virus; and wherein the synthetic peptide induces a cytotoxic T lymphocyte response specific for cells infected with the antiviral drug-resistant virus.

The viral load can be measured by methods known in the art and described herein. The method of lowering the viral load can be performed in HIV infected individuals having any measurable HIV viral load. In a preferred embodiment, the method of lowering the viral load is practiced in an HIV-infected individual having a viral load above 1,000,000 copies/ml, preferably above 500,000 copies/ml, more preferable above 100,000 copies/ml and most preferred above 10,000 copies/ml.

The goal of highly active antiretroviral therapy (HAART) is reducing HIV RNA to below detectable levels (<50 copies/ml of plasma).

4.1.1. Selecting an Antiviral Drug-Resistant Virus and a Predetermined Antiviral Drug-Resistant Mutation in a Viral Protein The antiviral drug-resistant virus can be any virus described or referred to herein. Typically, in addition to recognizing clinical symptoms of a chronic viral infection, immunoassays or PCR-based methods are employed to identify the virus in a host, preferably a patient, who is suspected of having a chronic viral infection. Usually, after identification of the virus, treatment of the host using an antiviral drug therapy is commenced. In cases where the host does not respond to this therapy, that is, for example, when no reduction of viral load is observed or initially responds but then loses the response, it is highly likely that the virus has accumulated one or more mutations in one or more of the viral protein encoding genes and as such in a viral protein. The viral genes or viral proteins may then be sequenced, using methods known in the art, to identify the respective mutation(s). Likewise, antibodies specifically recognizing one of the predetermined antiviral drug-resistant mutations described in Tables 1 through 5, may be used to identify a mutated viral protein.

The viral protein can be any viral protein of the antiviral drug-resistant virus for which an antiviral drug-resistant mutation (see Tables 1 through 5) or a newly identified mutation is identified.

4.1.2. Selecting a Peptide Comprising a Predetermined Antiviral Drug-Resistant Mutation In one embodiment of the present invention, a synthetic peptide comprises at least six amino acid residues flanking the predetermined antiviral drug-resistant mutation that are identical to the amino acid sequence of the viral protein of the antiviral drug-resistant virus.

Synthetic peptides of the present invention may be described by comprising an amino acid sequence of one of the following formulas: $A_1A_2A_3A_4A_5A_6P_M$, $A_1P_MA_2A_3A_4A_5A_6$, $A_1A_2P_MA_3A_4A_5A_6$, $A_1A_2A_3P_MA_4A_5A_6$, $A_1A_2A_3A_4P_MA_5A_6$, or $A_1A_2A_3A_4A_5A_6P_M$, wherein, $A_1$, $A_2$, $A_3$, $A_4$, $A_5$, and $A_6$ are the six amino acid residues flanking the predetermined antiviral drug resistant mutation ($P_M$) and wherein $A_1$, $A_2$, $A_3$, $A_4$, $A_5$, and $A_6$ are identical to the amino acid sequence of the viral protein of the antiviral drug-resistant virus.

Thus, by way of example, in the context of the M184V substitution in the reverse transcriptase of HIV-1, a peptide may be chosen in the following manner. The M184V substitution occurs within the wild-type sequence MVIYQY MDDLYVG (SEQ ID NO:32), wherein the underlined M is substituted to V to result in the sequence MVIYQY VDDLYVG (SEQ ID NO:33). According to the above formulas, a peptide can comprise one of the following sequences: MVIYQYV (SEQ ID NO:34; $A_1A_2A_3A_4A_5A_6P_M$), VIYQYVD (SEQ ID NO:35; $A_1A_2A_3A_4A_5P_MA_6$), IYQYVDD (SEQ ID NO:36; $A_1A_2A_3A_4P_MA_5A_6$), YQYVDDL (SEQ ID NO:37; $A_1A_2A_3P_MA_4A_5A_6$), QYVDDLY (SEQ ID NO:38; $A_1A_2P_MA_3A_4A_5A_6$), YVDDLYV (SEQ ID NO:39; $A_1P_MA_2A_3A_4A_5A_6$) or VDDLYVG (SEQ ID NO:40; $P_M$ $A_1A_2A_3A_4A_5A_6$). In these peptides, the six amino acid residues ($A_1$, $A_2$, $A_3$, $A_4$, $A_5$, and $A_6$) flanking the predetermined antiviral drug-resistant mutation ($P_M$, here V) are identical to the amino acid sequence of the reverse transcriptase of the antiviral drug-resistant virus. Also, in the above sequences, the six amino acids are not interrupted by any other amino acid residue. A preferred peptide of the present invention comprise the sequence VIYQYVDDL (SEQ ID NO:3), which according to the above comprises VIYQYVD (SEQ ID NO:34), IYQYVDD (SEQ ID NO:35), or YQYVDDL (SEQ ID NO:36), and wherein the underlined V is $P_M$.

In another embodiment of the present invention, the six amino acid residues ($A_1$, $A_2$, $A_3$, $A_4$, $A_5$, and $A_6$) flanking the predetermined antiviral drug-resistant mutation ($P_M$) are identical to the amino acid sequence of the reverse transcriptase of the antiviral drug-resistant virus and are interrupted by another amino acid residue. For example, a preferred peptide of the present invention comprises the sequence VLYQYVDDV (SEQ ID NO:6), wherein the underlined Vis $P_M$, 1V, 3Y, 4Q, 5Y, 7D, and 8D (shown in italics) are the six amino acid residues ($A_1$ through $A_6$) flanking the predetermined antiviral drug-resistant mutation ($P_M$, here V) and occur at the same position as in the RT sequence, 2L is an amino acid residue interspersed within the six amino acid residues, and 9V is added at the C-terminus of the 6th amino acid residue ($A_6$).

Sequences of viral proteins for HIV-1, HIV-2, HBV, HCV, and human herpesviruses can be retrieved from GenBank or from numerous publications. Thus, without undue experimentation and using the disclosure herein, a skilled artisan can identify and select a peptide comprising a predetermined antiviral drug-resistant mutation according to the invention.

4.1.3. Measuring Viral Load

Along with disease signs and symptoms, assays for viral load help to determine the health of a host, preferably a patient, and the need for an antiviral drug therapy. Measurements of, for example, HIV-1 RNA blood levels, provide an important prognostic marker of disease progression and a valuable tool for the management of individual patients. For example, viral loads are increasingly used by health care providers to determine when to start antiviral drug therapy or when to change a current therapy. Studies have shown that for a number of viral diseases, the level of virus in the blood is a good predictor of disease progression. Individuals with a high HIV-1 load in their blood are more likely to rapidly progress to AIDS than people with a lower load. An expert panel for the International AIDS Society-USA (Saag et al., Nature Medicine 1996, 2:625-629) has issued guidelines when viral load should usually be measured.

This invention contemplates various assays for measuring viral load in a sample. Synonyms of the term "measuring viral load" are contemplated within the scope of the present invention and include, but are not limited to, detecting, measuring, testing or determining, the presence, absence, amount or concentration of a virus, viral DNA, viral RNA or viral protein in a sample. Assays useful for measuring viral load include, but are not limited to, PCR, bDNA, ELISA, and other immunoassays, PAGE and Western blotting.

Using the methods of the invention, in a host infected with a virus causing a chronic infection, viral load can be measured at various times. Performing multiple measurements over time allows monitoring the regression or progression of a chronic viral infection in a host. Thus, the viral load in a sample from a host can be measured at a first time, for example, after diagnosing the chronic viral infection and before administrating to the host a peptide, medicament or vaccine of the present invention. A second measurement can be performed at a second time, for example after the peptide, medicament or vaccine of the present invention has been administered to the host. A lower viral load at the second measurement indicates that the chronic viral infection in the host is regressing. Likewise, a higher viral load or an unchanged viral load at a second time compared to the viral load at the first time, indicates that the chronic viral infection is progressing or remains unchanged.

The effectiveness of a peptide, medicament or vaccine of the present invention can also be measured by one or more of the methods described herein.

(a) Samples

In one embodiment of the present invention, the viral load is measured in a sample. "Sample" refers to any sample obtained from a living or dead host. Examples of samples include biological fluid and biological tissue specimens. For the purpose of the present invention, a biological fluid can be any physiological fluid sample, preferably a mammalian physiological fluid sample, most preferably a human physiological fluid sample. "Physiological fluid sample" refers to a fluid from a host and includes whole blood, serum, plasma, urine, tears, mucus ascites, oral fluid, saliva, semen seminal fluid, vaginal fluid, mucus, stool, sputum, cerebrospinal fluid, bone marrow, lymph node and fetal fluid. The biological fluid samples may include cells, protein or membrane extracts of cells. In a preferred embodiment of the present invention, the physiological fluid sample is whole blood, serum or plasma.

The sample may also be a tissue specimen. Thus, the viral load is measured in a tissue specimen from a host. Examples of tissue specimen useful to practice the methods of the present invention include samples taken from the central nervous system, skin, bone, breast tissue, renal tissue, endometrium, head/neck, gall bladder, parotid tissue, brain, pituitary gland, kidney tissue, muscle, esophagus, stomach, small intestine, colon, urethea, liver, spleen, pancreas, prostate, thyroid tissue, heart, lung, bladder, adipose tissue, vaginal tissue, lymph node tissue, adrenal tissue, testis tissue, tonsils, and thymus. Preferably, the sample is lymph node tissue, most preferably a human lymph node tissue sample.

In another embodiment, the sample is an in vitro sample and includes, for example, cells grown in vitro and supernatants of these cells.

(b) PCR

The concentration of viral DNA or RNA in a sample, such as plasma, of an infected individual is an important predictor of disease outcome and a marker of antiviral drug efficiency and efficacy. Viral load may be determined by detecting, measuring, testing or determining, the presence, absence, amount or concentration of viral DNA or viral RNA in a sample. A preferred method is the polymerase chain reaction (PCR). Sequences of viral DNA or RNA sequences for HIV-1, HIV-2, HBV, HCV and human herpesviruses can be retrieved from GenBank or from numerous publications. Thus, without undue experimentation a skilled artisan can identify and select a pair of oligonucleotide primers for performing PCR and detect a virus of interest. Various kits for performing PCR are commercially available (for example, from Hoffman-LaRoche). Several PCR tests for detection of HIV-1 RNA in plasma have been approved by the Food and Drug Administration (FDA; see Mulder et al., J Clin Microbiol 1994, 32:292-300; Sun et al., J Clin Microbiol 1998, 36:2964-2969). Further, Palmer et al. (J Clin Microbiol 2003, 41(10):4531-4536) described a new real-time reverse transcriptase-initiated PCR assay with single-copy sensitivity for HIV-1 RNA in plasma.

(c) bDNA

Another preferred method to measure viral load is branched DNA (bDNA) analysis. Quantitative hybridization assays based on branched DNA signal amplification are widely used to monitor hosts, preferably patients, on antiviral therapy for HIV-1, HBV or HCV. The most important characteristics of these hybridization assays are sensitivity, wide dynamic range, and precise and accurate quantification. There are many different versions of bDNA signal amplification assays. In all versions, however, the linearly amplified signal is directly related to the number of target sequences present in the original sample. This first generation bDNA assays quantified nucleic acids of between ~10 000 and 10 000 000 molecules; assays for HIV, HCV and HBV have been developed (Pachl et al., J Acquired Immune Def Synd 1995, 8:446-454; Alter et al., J Viral Hep 1995, 2:121-132; Detmer et al., J Clin Microbiol 1996, 34:901-907; Zaaijer et al., J Clin Microbiol 1994, 32:2088-2091; Hendricks et al., Am J Clin Pathol 1995, 104:537-546). The second generation HIV bDNA assay had a quantitative detection limit of 500 molecules (Kern et al., J Clin Microbiol 1996, 34:3196-3202). Collins et al. (Nucl. Acids Res 1997, 25(15):2979-2984) reported a branched DNA signal amplification assay for quantification of nucleic acid targets below 100 molecules/ml.

bDNA tests are also commercially available. For example, Chiron Diagnostics has developed a bDNA test for HIV-1, which is marketed under the name Quantiplex®HIV-RNA.

(d) Antibodies

Viral load may also be determined by detecting, measuring, testing or determining, the presence, absence, amount or concentration of a virus or viral protein in a sample.

This invention contemplates traditional immunoassays for measuring a viral load. Immunoassays, as further described herein, require a biospecific capture reagent, such as an antibody, to capture a virus or viral protein.

"Antibody" refers to a protein functionally defined as a binding protein (a molecule able to bind to a specific epitope on an antigen) and structurally defined as comprising an amino acid sequence that is recognized by one of skill as being derived from the framework region of an immunoglobulin encoding gene. Structurally, the simplest naturally occurring antibody (e.g., IgG) comprises four polypeptides chains, two copies of a heavy (H) chain and two copies of a light (L) chain, all covalently linked by disulfide bonds. Specificity of binding is found in the variable (V) determinant of the H and L chains. Regions of the antibodies that are primarily structural are constant (C). The term "antibody" includes whole antibody, functional fragments, modifications or derivatives of the antibody. It can also be a genetically manipulated product, or bispecific antibody or chimeric antibody, such as a humanized antibody. Antibodies can be a polyclonal mixture or monoclonal. Antibodies can be intact immunoglobulins derived from natural sources or from recombinant sources and can be immunoreactive portions of intact immunoglobulins. Antibodies may exist in a variety of forms including, for example, Fv (consisting of the $V_L$ and $V_H$ domains of a single arm of an antibody), Fd (consisting of the $V_H$ and $C_{H1}$ domains), a dAB fragment (consisting of a $V_H$ domain; Ward et al., Nature, 341:544-546, 1989), an isolated complementary determining region (CDR), Fab (consisting of the $V_L$, $V_H$, $C_L$, and $C_{H1}$ domains, and F(ab)$_2$ (a bivalent fragment comprising two Fab fragments linked by a disulfide bridge at the hinge region) as well as in single chains. Single-chain antibodies (SCA), in which genes for a heavy chain and a light chain are combined into a single coding sequence, may also be used. Some SCA are genetically engineered molecules containing the variable region of the light chain, the variable region of the heavy chain, linked by a suitable polypeptide linker.

An antibody of the present invention is reactive to a wild-type viral protein or a mutant viral protein. "Antibody reactive to a protein" means that the antibody has an area on its surface or in a cavity which specifically binds to a particular wild-type viral protein or a mutant viral protein, i.e., it has a binding affinity (usually expressed as Ka) for the wild-type viral protein or a mutant viral protein.

An antibody that is specifically immunoreactive with and binds to a mutant viral protein of the present invention is also provided. The term "specifically immunoreactive" as used herein indicates that an antibody preferentially recognizes and binds to a mutant viral protein over the corresponding wild-type viral protein. The term "preferentially recognize and bind" as used herein means that antibodies of the present invention bind more tightly to a mutant viral protein of the present invention (such as a peptide comprising a predetermined antiviral drug-resistant mutation at position 184 of HIV-1 reverse transcriptase (e.g., Met184Val or Met1984Ile) than to the wild-type viral protein (such as a peptide having a methionine at position 184 of HIV-1 reverse transcriptase). The cross reactivity of anti mutant viral protein antibodies to a wild-type viral protein is relatively low, preferably less than about 10%, and most preferably less than about 1%.

Polyclonal and monoclonal antibodies or active fragments thereof specifically immunoreactive with and binding to a mutant viral protein can be made from an antigen containing a peptide comprising a predetermined antiviral drug-resistant mutation by methods well known to the skilled artisan (Harlow et al., *Antibodies: A Laboratory Manual*, Cold Spring Harbor Laboratory, 1988; Coligan et al., *Current Protocols in Immunology*, Wiley Interscience, 1991; all incorporated by reference). Thus, peptides of the present invention can be used as an immunogen that is capable of elicitating a monoclonal antibody which preferentially recognizes and binds to a viral protein comprising a predetermined antiviral drug-resistant mutation. An immunogen of the present invention may include a peptide comprising a predetermined antiviral drug-resistant mutation as described herein or a fragment thereof.

(e) ELISA and Other Immunoassays

In another aspect, the viral load is measured by measuring the presence, absence, amount or concentration of a viral protein by enzyme-linked immunosorbent assay (ELISA) or other immunoassays, such as sandwich ELISA, competitive ELISA, immunoprecipitation, immunohistochemistry, immunofluorescence, radioimmune assay (RIA), and/or immunoradiometric assay (IMRA). These assays are well known in the art. For example, by employing a sandwich assay a first antibody captures more than one form of a viral protein (e.g., an antibody recognizing and binding to both, a wild-type viral protein and a mutant viral protein) and a second, distinctly labeled antibody specifically recognizes and binds, and provides distinct detection of the mutant viral protein (e.g., an antibody preferentially recognizing and binding to a mutant viral protein, such as one comprising an amino acid substitution at position 184 of HIV-1 reverse transcriptase).

Proteins or peptides of the present invention may be detected by using an antibody comprising a detectable label. A "labeled antibody" includes antibodies that are labeled by a detectable means and include enzymatically, radioactively, fluorescently, chemiluminescently, and/or bioluminescently labeled antibodies. Enzymes which can be used to detectably label antibodies include, but are not limited to, horseradish peroxidase, malate dehydrogenase, *staphylococcal* nuclease, delta-5-steroid isomerase, yeast alcohol dehydrogenase, alpha-glycerophosphate dehydrogenase, triose phosphate isomerase, alkaline phosphatase, beta-galactosidase and glucose-6-phosphate dehydrogenase.

Particularly useful isotopes for radioactively labeling of antibodies include, but are not limited to $^3$H, $^{131}$I, $^{123}$I, $^{32}$P, $^{35}$S, $^{14}$C, $^{51}$Cr, $^{36}$Cl, $^{57}$Co, $^{51}$Co, and preferably $^{125}$I.

Among the most commonly used fluorescent labeling compounds are fluorescin isothiocyanate, rhodamine, phycoerytherin, phycocyanin, allophycocyanin, o-phtaldehyde and fluorescamine. Fluorescence-emitting metal atoms such as Eu (europium), and other lanthanides, can also be used.

Examples of particularly useful chemiluminescent labeling compounds are luminol, luciferin, isoluminol, aromatic acridinium ester, imidazole, acridinium salt and oxalate ester. Important bioluminescent compounds for the purpose of labeling antibodies are luciferin, luciferase and aequorin.

In the diagnostic and prognostic assays of the invention, the amount of binding of the antibody to an antigen (e.g., a mutant viral protein) in a sample can be determined by the intensity of the signal emitted by the labeled antibody, and/or by the number of cells in the sample bound to the labeled antibody.

Furthermore, in vivo techniques for detection of a peptide of the present invention include introducing into a subject a labeled antibody directed against the peptide. For example, the antibody can be labeled with a radioactive marker whose presence and location in a subject can be detected by standard imaging techniques.

(f) PAGE and Western Blot

In another aspect of the present invention, the viral load is measured by measuring the presence, absence, amount or concentration of a viral protein by PAGE. "PAGE" means polyacrylamide gel electrophoresis and includes one-dimensional (1-D) PAGE and two-dimensional (2-D) PAGE (Srinivas et al., Clin Chem 2001, 47:1901-1911; Adam et al., Proteomics 2001, 1:1264-1270). Analysis by PAGE may optionally be followed by Western blotting and detection of the viral protein using an antibody specific for the viral protein of interest.

4.2. Method for Destroying Cells Infected with a Mutated Virus

The peptide compositions may also be used to stimulate the immune system to eliminate virus-infected cells in carriers, that is in a host, preferably a patient, infected with the virus. Alternatively, the peptide compositions may be used in vitro to destroy cells infected with an antiviral drug-resistant virus.

Thus, in a preferred embodiment of the present invention, a method for destroying cells infected with an antiviral drug-resistant virus is provided. The method comprises the steps of (a) inducing cytotoxic T lymphocytes to recognize a mutated epitope of the antiviral drug-resistant virus and (b) contacting the cells with the cytotoxic T lymphocytes; thereby destroying the cells. The mutated epitope of the peptide comprises one of the predetermined antiviral drug-resistant mutations described or referred to herein, for example, those identified in the HIV-1 reverse transcriptase or HIV-1 protease.

In a preferred embodiment of the present invention, the cytotoxic T lymphocytes are induced by immunization of a host with a synthetic peptide having a length of between 9 and 15 amino acid residues, wherein the synthetic peptide comprises a predetermined antiviral drug-resistant mutation in a viral protein. A preferred predetermined antiviral drug-resistant mutation is the substitution of 184M in the HIV-reverse transcriptase or 204M in the HBV polymerse. Thus, in the context of HIV-1 reverse transcriptase, a preferred peptide comprises the amino acid sequence VIYQYIDDL (SEQ ID NO:4) or VIYQYVDDL (SEQ ID NO:3). In one aspect, at least one amino acid residue of the synthetic peptide is substituted to serve as an epitope enhancement. Thus, in the context of HIV-1reverse transcriptase, a preferred peptide comprises the amino acid sequence VLYQYIDDV (SEQ ID NO:5) or VLYQYVDDV (SEQ ID NO:6), wherein 2L and 9V serve as an epitope enhancement.

In another preferred embodiment, these peptides have an additional amino acid substitution, where 1V is substituted by 1Y. Thus, in the context of HIV-1 reverse transcriptase, a preferred peptide comprises the amino acid sequence YLYQYIDDV (SEQ ID NO:18) or YLYQYVDDV (SEQ ID NO:17) (see Examples).

It is important to provide an amount of an immunostimulating peptide in a formulation and mode of administration sufficient to effectively stimulate a cytotoxic T cell response. Thus, in these cases, a representative dose is in the range of about 0.001 to about 10 mg/kg, more preferably about 0.01 to about 2 mg/kg, most preferably about 0.01 to 1 mg/kg peptide per dose. Immunizing doses followed by boosting doses at established intervals, e.g., from one to four weeks, may be required, possibly for a prolonged period of time to effectively immunize an individual. Administration may continue until clinical symptoms or laboratory tests indicate that the viral infection has been eliminated or substantially abated and for a period thereafter.

4.3. Method for Providing an Immune Counter-Selective Pressure to Prevent or Suppress a Viral Escape Mutation During Viral Therapy As described herein, the development of drug-resistance is the most important barrier to persistently effective antiretroviral therapy. The present invention provides for therapeutic vaccination to target resistant mutations of HIV and focuses on the specificity of the immune system on resistant HIV strains to prevent their outgrowth. Thus, in another preferred embodiment of the present invention, a method for providing an immune counter-selective pressure to prevent or suppress a viral escape mutation during antiviral therapy, is provided. This method comprises the steps of (a) enhancing an epitope of a viral amino acid sequence comprising a predetermined antiviral drug-resistant mutation, wherein the enhancing is performed by altering the amino acid sequence of the epitope and (b) inducing cytotoxic T lymphocytes to specifically recognize the predetermined antiviral drug-resistant mutation in a viral protein using the enhanced epitope of step (a). Enhancing an epitope leads to an increase in immune response.

The viral escape mutation can be any antiviral drug-resistant mutation as described herein (see Tables 1 through 5) or a newly identified mutation. Preferably the escape mutation is a predetermined antiviral drug-resistant mutation in HIV-1 reverse transcriptase or in HIV-1 protease.

Preferably, this method is used as soon as a host, preferably a patient, has been diagnosed with a chronic viral infection and the virus causing the chronic infection has been identified, ideally even before the onset of an antiviral drug therapy, that is, at a time when no antiviral drug-resistant virus is present. It can also be utilized soon after the start of antiviral therapy. Tables 1 through 5 show which predetermined antiviral drug-resistant mutations have been identified upon administering a certain antiviral drug. Thus, for example, numerous studies have shown that after starting lamivudine treatment, HIV-1 mutations M184I or M184V accumulate. Thus, selecting an appropriate epitope comprising this mutation, as has been described herein and using the method of the present invention, it is possible to prime the individual's immune system. As soon as the RT of HIV-1 mutates into the M184I or M184V version, CTLs will recognize those versions and destroy the cells. Thereby the appearance of a viral escape mutation during antiviral therapy is prevented, delayed, or suppressed.

4.4. Method for Eradicating a Viral Escape Mutant Virus

In another preferred embodiment of the present invention, a method for eradicating a viral escape mutant virus, is provided. This method comprises the steps of (a) enhancing an epitope of a viral amino acid sequence comprising a predetermined antiviral drug-resistant mutation, wherein the enhancing is performed by altering the amino acid sequence of the epitope and (b) inducing cytotoxic T lymphocytes to specifically recognize the predetermined antiviral drug-resistant mutation in a viral protein using the enhanced epitope of step (a). Enhancing an epitope leads to an increase in immune response.

The viral escape mutant virus can be any antiviral drug-resistant virus as described herein and may comprise any of the predetermined antiviral drug-resistant mutations as described in Tables 1 through 5. Alternatively, an antiviral drug resistant mutation may be identified by sequencing the nucleotide sequence of the antiviral drug-resistant virus isolated from a host. Preferably the escape mutant virus is a mutant HIV-1 and comprises a predetermined antiviral drug-resistant mutation in reverse transcriptase or protease.

Preferably, this method is used after antiviral drug therapy has been initiated, that is, at a time when an antiviral drug-resistant virus is present. The mutation of the antiviral drug-resistant virus can be identified by any method known in the art or as described herein. As soon as the CTLs are induced to specifically recognize, for example, a mutated epitope of RT (M184I or M184V), CTLs will recognize those HIV-1 RT versions and destroy the cells. Thereby any viral escape mutant virus will be suppressed or eradicated.

4.5. Method for Assessing an Immune Response against a Virus

Methods for assessing immune function or diagnosing exposure of a subject to a virus are also contemplated as being part of the invention. In one aspect the method comprises at a minimum, contacting a blood sample, including T cells, obtained from the host cells with a peptide or protein of the present invention, and then determining an immune response of the host's T cells to the peptide or protein of the present invention. In some aspects, the determining step is performed by assaying for RANTES or IFN-γ production, or lysis of cells displaying a peptide of the present invention by cytotoxic T lymphocytes, or any combination of the three parameters, induced with the peptide.

Other methods of diagnosing exposure of a host to a virus include contacting a blood sample from the host, having antibodies, with a peptide of the present invention and determining the presence of antibodies that bind to the peptide.

The peptide also finds use as diagnostic reagents. For example, a peptide of the invention may be used to determine the susceptibility of a particular individual to a treatment regimen that employs the peptide or related peptides, and thus may be helpful in modifying an existing treatment protocol or in determining a prognosis for an affected individual. In addition, the peptides may also be used to predict which individuals will be at substantial risk for developing a chronic viral infection.

An important aspect to the diagnosis and treatment of any chronic viral infection is determining the presence of infection, and monitoring the viral load of the infected individual. The present invention addresses these issues by providing methods of assessing immune function or diagnosing exposure to HIV-1 or hepatitis B for a subject, particularly to antiviral drug-resistant strains of HIV-1 or hepatitis B. Performing the methods involves contacting, for example, a blood sample from a host that contains T cells with an immunostimulating peptide of the present invention; and, determining if peptide contact induces an immune response, preferably a CTL response. The blood sample will need to contain any viral antigen-presenting cells. These cells may be endogenous to the sample, or added from an external source. Antigen-presenting cells can be normal cells such as peripheral blood mononuclear cells or dendritic cells (Inaba, et al., J Exp Med 1987, 166:182; and Boog, Eur J Immunol 1988, 18:219).

Next, peptides that test positive in the MHC class I binding assay are assayed for the ability of the peptides to induce specific CTL responses in vitro. For instance, antigen-presenting cells that have been incubated with a peptide can be assayed for the ability to induce CTL responses in responder cell populations.

Alternatively, mutant mammalian cell lines that are deficient in their ability to load class I molecules with internally processed peptides, such as the mouse cell lines RMA-S (Karre, et al. Nature, 319:675 (1986); Ljunggren, et al., Eur. J. Immunol. 21:2963-2970 (1991)), and the human somatic T cell hybridoma, T-2 (Cerundolo, et al., Nature 345:449-452 (1990)) and that have been transfected with the appropriate human class I genes may be conveniently used. To test for the capacity of an immunostimulating peptide of the invention to induce in vitro primary CTL response, the peptide is added to the cells. Other eukaryotic cell lines which could be used include various insect cell lines such as mosquito larvae (ATCC cell lines CCL 125, 126, 1660, 1591, 6585, and 6586), silkworm (ATTC CRL 8851), armyworm (ATCC CRL 1711); moth (ATCC CCL 80) and *Drosophila* cell lines such as a Schneider cell line (see Schneider J., Embryol Exp Morphol 1927, 27:353-365), that have been transfected with the appropriate human class I MHC allele encoding genes and the human $B_2$ microglobulin genes.

Alternatively, IFN-γ and/or RANTES production by stimulated T cells can be measured in the T cell culture supernatant. Methods for measuring CTL response, RANTES and IFN-γ production of stimulated T cells are well known in the art, some of which are discussed in the general methods of the examples section, below and elsewhere in this specification.

Another assay suitable for determining exposure to HIV-1 or HBV involves contacting the peptide VLYQYVDDV (SEQ ID NO:6), or a molecule comprising VLYQYVDDV (SEQ ID NO:6), with a blood sample from a host, preferably a patient, containing antibodies. If the host has been exposed to HIV-1 or HBV, then the blood sample will contain antibodies specifically recognizing the VLYQYVDDV (SEQ ID NO:6) peptide. Determining the presence of antibody binding to the peptide is a positive indication that the host has been exposed to the virus. Preferably the peptide is immobilized, but other embodiments are contemplated as the invention. Alternative embodiments for ELISA-type assays are well known to those of skill in the art.

The immunogenic peptides of this invention may also be used to make monoclonal antibodies. Such antibodies may be useful as potential diagnostic or therapeutic agents.

4.6. Method for Increasing the CD4 Count

If untreated, HIV infection damages the immune system, resulting in a decline in the CD4 count and subsequent development of opportunistic infections with AIDS related malignancies. Further, clinical trials demonstrate that even if patients have no detectable viral load for 3 years, those who discontinue antiretrovirals experience a rapid rebound of viremia and a drop in their CD4 count (Davey et al., Proc Natl Acad Sci USA 1999, 96(26):15109-14; Ortiz et al., Proc Natl Acad Sci USA 2001, 98(23):13288-93).

Thus, in another preferred embodiment of the present invention, a method for increasing the CD4 count, is provided. The method comprises the step of administering to a host, preferably a patient, a medicament, the medicament comprising (i) the antiviral drug in an amount effective to increase the CD4 count, wherein the antiviral drug is capable of selecting for a predetermined antiviral drug-resistant mutation in a viral protein, thereby creating an antiviral drug-resistant virus; and (ii) a synthetic peptide having a length of between 9 and 15 amino acid residues, the synthetic peptide comprising (1) the predetermined antiviral drug-resistant mutation in the viral protein; and (2) at least six amino acid residues flanking the predetermined antiviral drug-resistant mutation that are identical to the amino acid sequence of the viral protein of the antiviral drug-resistant virus; and wherein the synthetic peptide induces a cytotoxic T lymphocyte response specific for cells infected with the antiviral drug-resistant virus.

The CD4 count can be measured by methods known in the art, e.g., FACS. In a preferred embodiment, the method of increasing the CD4 count is practiced in an HIV-infected individual having a CD4 count of below 2,000, preferably below 1,500, more preferably below 1,000 and most preferred below 350.

4.7. Method for Extending the Utility of HIV Drugs

This invention provides evidence that it may be possible to target drug resistant strains of HIV with specific CTLs before viremia from drug resistant strains is clinically apparent. Optimal utility of such a vaccine may result in the prevention of clinical resistance by suppressing the development of resistant mutants. In that case, the extended use of HIV drugs known to lead to resistant strains should be possible to further lower viral load. Thus, in another preferred embodiment of the present invention the induction of a CTL response in patients specific for a drug resistant mutant is applied to extend the utility of other HIV drugs, such as lamivudine and others described herein.

From the foregoing it is believed that those familiar with the art will readily recognize and appreciate the novel concepts and features of the present invention. Although the foregoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit, scope and principles of this invention. As a result, the embodiments described herein are subject to various modifications, changes and the like, with the scope of this invention being determined solely by reference to the claims appended hereto.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The invention is further illustrated by the following examples, which are only illustrative and are not intended to limit the definition and scope of the invention in any way.

5. EXAMPLES

5.1. Example 1

Material and Methods

5.1.1. Synthetic Peptides

Peptides were prepared on an automated multiple peptide synthesizer (Symphony; Protein Technologies, Inc.) using Fmoc chemistry. Peptides were purified by reverse-phase HPLC. Subsequently peptide composition and concentration were confirmed by amino acid analysis and where necessary, sequences were confirmed on an automated sequencer (477A; Applied Biosystems, Foster City, Calif.). Some peptides were also purchased from Multiple Peptide Systems (San Diego, Calif.).

5.1.2. Cells

The C1R.AAD cell line (HMYC1R transfected with the HLA chimeric molecule containing α1 and α2 domains from human HLA-A2.1 and α3 from mouse H-2D$^d$) has been previously described (Newberg et al., J Immunol 1996, 156:2473-2480; Sarobe et al., J Clin Invest 1998, 102(6):1239-1248). Cell lines were maintained in RPMI containing 10% FCS, 1 mM sodium pyruvate, nonessential amino acids (Biofluid, Rockville, Md.), 4 mM glutamine, 100 U/ml penicillin, 100 µg/ml streptomycin and 50 µM 2-mercaptoethanol (henceforth designated complete T cell medium, CTM).

5.1.3. Mice

Transgenic HHD-2 mice (a gift of Dr. François Lemonnier, Institut Pasteur, Paris, France) were bred in our colony at BioCon Inc. (Rockville, Md.). HHD-2 mice are characterized by a double knock-out of the murine $\beta_2$-microglobulin gene, as well as murine H-2D$^b$ gene, transgenic expression of human HLA-A2.1 with a covalently-linked human $\beta_2$-microglobulin to compensate for lack of any free $\beta_2$-microglobulin and a murine D$^b$-derived $\alpha$3 domain to allow interaction with mouse CD8$^+$ T cells. As a result of this lack of any free $\beta_2$-microglobulin, even though the H-2K$^b$ gene is not knocked out, the only class I MHC molecule this strain expresses is the chimeric human HLA-A2.1 with the covalent human $\beta_2$-microglobulin, not any murine class I molecule. Therefore, in this strain, all CTL are restricted only to the human class I HLA molecule, and any protection cannot be mediated by CTL restricted to murine class I MHC molecules (Pascolo et al., J Exp Med 1997, 185(12):2043-51; Firat et al., Eur. J. Immunol 2001, 31(10):3064-74).

5.1.4. Binding Assays

Peptide binding to HLA molecules was measured using the T2 mutant cell line as described (Nijman et al., Eur J Immunol 1993, 23:1215-1219; Sarobe et al., J Clin Invest 1998, 102(6):1239-1248). T2 cells (3×10$^5$/well) were incubated overnight in 96-well plates with culture medium (a 1:1 mixture of RPMI 1640/EHAA containing 2.5% FBS, 100 U/ml penicillin, 100 µg/ml streptomycin) with 10 µg/ml human β2-microglobulin (Sigma Chemical Co., St. Louis, Mo.) and different peptide concentrations as shown in the figures. On the following day, cells were washed twice with cold PBS containing 2% FCS and incubated for 30 min at 4° C. with anti-HLA-A2.1 mAb BB7.2 (1/100 dilution of hybridoma supernatant) and 5 µg/ml FITC-labelled goat anti-mouse Ig (Pharmingen, San Diego, Calif.). Cells were washed twice after each incubation. Subsequently, HLA-A2.1 expression was measured by flow cytometry (FACScan; Becton Dickinson, Mountain View, Calif.). HLA-A2.1 expression was quantified as fluorescence index (FI) according to the formula: FI=(mean fluorescence with peptide–mean fluorescence without peptide)/mean fluorescence without peptide. FI$_{0.5}$ is the concentration (µM) required to give an FI of 0.5, meaning 50% increase in HLA-A2 on the cell surface. Background fluorescence without mAb BB7.2 was subtracted for each individual value. The peptides used herein are chemically stable at 37° C. and are short enough that they have no native conformation to denature, so peptide stability should not be an issue in this assay.

5.1.5. CTL Generation in HHD-2 Transgenic Mice

Mice more than eight weeks of age were immunized subcutaneously in the base of the tail with 100 µl of an emulsion containing 1:1 incomplete Freund's adjuvant (IFA) and PBS solution with antigens and cytokines (50 nmol CTL epitope, 50 nmol HBV core 128-140 helper epitope, 5 µg of IL-12 and 5 µg of granulocyte-macrophage colony stimulating factor). Mice were boosted two weeks later. Spleens were removed 10-14 days after the boost. Immune spleen cells (2.5×10$^6$/well) were stimulated in 24-well plates with autologous spleen cells (5×10$^6$/well) pulsed for 2 h with 10 µM CTL epitope peptide in CTM supplemented with 10% T-Stim (Collaborative Biochemical Products, Bedford, Mass.). Following more than 4 in vitro stimulations with peptide-pulsed syngeneic spleen cells, CTL lines were maintained by weekly restimulation of 1×10$^6$ CTL/well with 4×10$^6$ peptide pulsed irradiated (3,300 rads) gynogeneic spleen cells as feeders, or by weekly stimulation of 1×10$^6$ CTL/well with 3.8×10$^6$ peptide pulsed irradiated C57BL/6 spleen cells and 1-3×10$^5$ peptide pulsed and irradiated (15,000 rad) Jurkat-A2K$^b$ transfectant cells.

5.1.6. Cytotoxicity Assay

CTL activity was measured using a 4-hr assay with $^{51}$Cr-labeled target cells (Okazaki et al., J Immunol 2003, 171(5):2548-2555). Target cells (10$^6$) were pulsed in 100 µl of CTM and 150 µCi $^{51}$Cr for 1.5 hr, washed three times, and added at 3,000 cells/well to the 96-well round-bottom plates with different peptide concentrations. Effector cells were introduced 2 h later. Then, the supernatants were harvested and counted following an additional 4-hr incubation. The percentage of specific $^{51}$Cr release was calculated as 100× (experimental release–spontaneous release)/(Maximum release–spontaneous release). Spontaneous release was determined from target cells incubated in the absence of effector cells. Maximum release was determined in the presence of 0.1 M HCl. C1R.AAD cell lines served as target cells.

5.1.7. Protection Assay from Viral Challenge

Protection assays from viral challenge may be performed essentially as described by Okazaki et al. (J Immunol 2003, 171(5):2548-2555). Female mice may be immunized using the same protocol as in the CTL generation protocol described above (5.1.5.), boosted i.p. 2 weeks after primary immunization, and challenged i.p. 30 days later with recombinant vaccinia virus (2×10$^7$ PFU/mouse) expressing HIV RT (vCF21) or β-galactosidase (vSC8). Five days later, virus loads in the ovaries of individual mice may be determined on BSC-1 indicator cells as described (Ahlers et al., Int Immunol 2001, 13:897-908).

5.2. Example 2

RT (179-187)-Substituted Peptides Binding to HLA-A2.1 Molecules

Figure 1B:
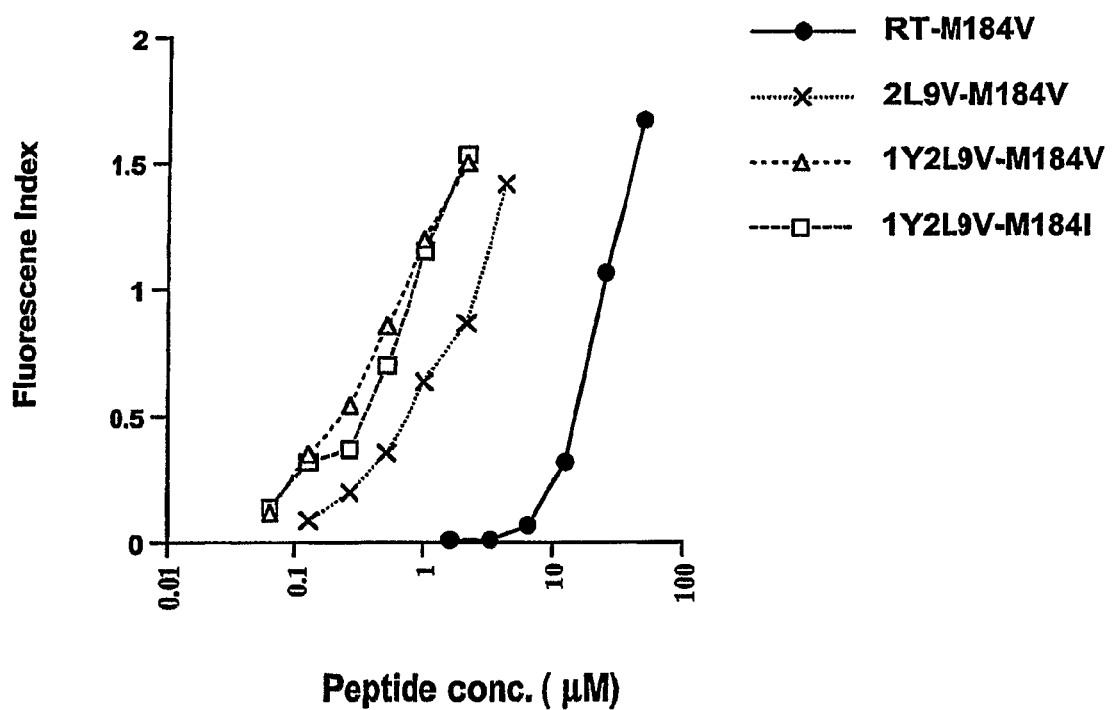
Figure 1b shows a comparison of the HLA-A2 binding curves among RT-M184V, 2L9V -M184V (VLYQYVDDV; SEQ ID NO:6), 1Y2L9V-M184V (YLYQYVDDV; SEQ ID NO:17) and 1Y2L9V-M184I (YLYQYIDDV; SEQ ID NO:18) in the T2-binding assay.
Figure 1C:
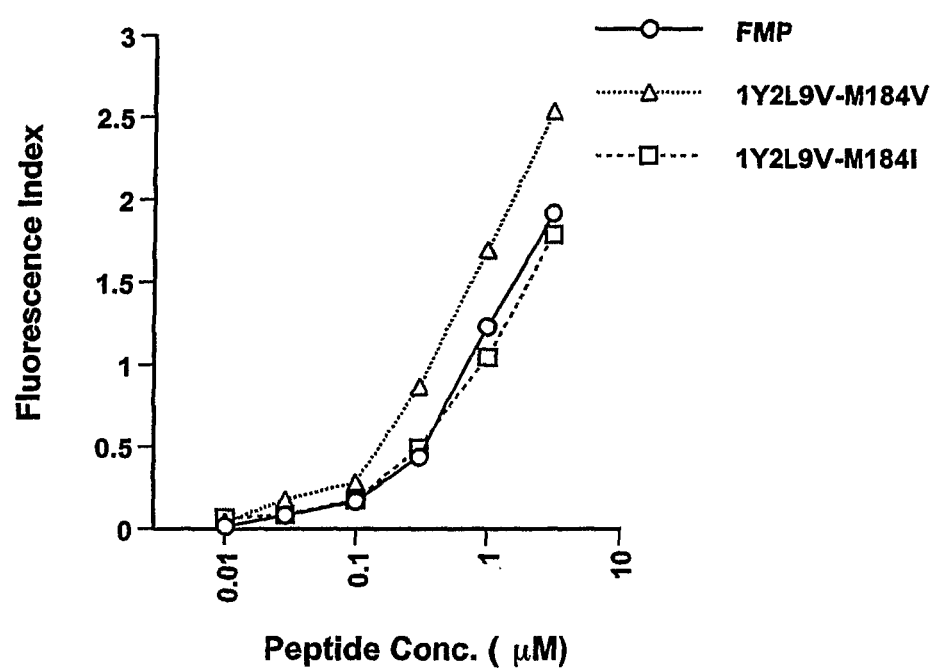
FIG. 1c shows a comparison of the HLA-A2 binding curves for 1Y2L9V-M184V and 1Y2L9V-M184I with that of the positive control peptide flu matrix peptide (FMP). Comparable results for each panel shown in FIGS. 1a, 1b, and 1c were obtained in two similar experiments.

To develop CTL to an epitope spanning the drug resistance mutation site that bound to HLA-A2, the binding of wild type and mutated peptides to HLA-A2 was measured. The T2-binding assay (Nijman et al., Eur J Immunol 1993, 23:1215-1219; Sarobe et al., J Clin Invest 1998, 102(6): 1239-1248) was utilized to assess whether the M184V mutation of RT (179-187), RT-M184V, possessed the ability to bind the HLA-A2 molecule. This protocol involved measurement of the cell surface stabilization of HLA-A2.1 molecules on Transporter of Antigenic Peptides (TAP)-deficient T2 cells following incubation with each peptide (FIG. 1). Several candidate peptides using epitope enhancement strategies were studied. Based on our previous results regarding epitope-enhancement of RT-WT (See PCT/US2004/009617; Okazaki et al., J Immunol 2003, 171(5): 2548-2555), and the results of Harrer et al. on peptides with the wild-type sequence (Harrer et al., J Infect Dis 1996, 173:476-9), the following peptides were selected: VIYQYMDDL (RT-WT; SEQ ID NO:1), VLYQYMDDV (RT-2L9V; SEQ ID NO:23), IVIYQYMDDL (I-RT-WT; SEQ ID NO:21), IVIYQYVDDL (I-RT-M184V; SEQ ID NO:22), VIYQYVDDL (RT-M184V; SEQ ID NO:3), VLYQYVDDV (2L9V-M184V; SEQ ID NO:6), YLYQYVDDV (1Y2L9V-M184V; SEQ ID NO:17), and YLYQYIDDV (1Y2L9V -M184I; SEQ ID NO:18).

As previously described (Firat et al., Eur J Immunol 2001, 31(10):3064-3074; Okazaki et al., J Immunol 2003, 171(5): 2548-2555), RT-WT was observed to bind weakly to the HLA -A2 molecule. We now find that peptide RT-M184V binds with somewhat stronger affinity than does RT-WT (FIG. 1a) (FI$_{0.5}$=32µM for RT-WT and 17.2 µM for RT -M184V). This result indicates that RT-M184V could be an antigenic epitope restricted to HLA-A2. However, both 10-mer peptides, I-RT-WT and I-RT-M184V, demonstrated weaker binding ability ($FI_{0.5}$=79 µM and 55 µM, respectively) to HLA-A2 as compared to the 9-mer peptide RT-WT, consistent with earlier results on recognition of the wild-type sequence 9- and 10-mer peptides by human CTL (Harrer et al., J Infect Dis 1996, 173:476-9), suggesting that the HLA-A2-restricted peptide derived from this RT region should be the 9-mer VIYQYMDDL (SEQ ID NO:1) of HIV-1 or VIYQYVDDL (SEQ ID NO:3) for the lamivudine-resistance mutation. The concordance with the human CTL results also strengthens the relevance to the human immune response.

Recent studies reported that a tyrosine substitution at the first position (P1Y) can improve peptide/MHC binding stability (Tourdot et al., Eur J Immunol 2000, 30(12):3411-3421; Okazaki et al., J Immunol 2003, 171(5):2548-2555). Building on these studies, the binding stability of 2L9V-M184V, 1Y2L9V-M184V and 1Y2L9V-M184I was examined. All three peptides exhibited much higher affinity for the HLA-A2 molecule in comparison to RT-M184V ($FI_{0.5}$=0.856 µM, 0.245 µM and 0.332 µM, respectively, compared to 15.1 µM for RT-M184V; FIG. L$b$). In particular, the P1Y mutation of 1Y2L9V-M184V and 1Y2L9V-M184I displayed binding capacity for the HLA-A2 molecule nearly equal to that of the positive control highly antigenic Flu matrix peptide (FMP) with the amino acid sequence GILGFVFTL (SEQ ID NO:41; influenza matrix amino acid residues 58-66; Gotch et al. Nature 1987, 326:881-882) $FI_{0.5}$ for 1Y2L9V-M184V was 0.176-0.245 µM, for 1Y2L9V-M184I was 0.332-0367, and for FMP was 0.338 µM (FIG. 1$c$). These results suggested that the peptide expressing the M184V mutation in the RT-WT epitope could function as at least as potent an antigenic epitope as the RT-WT epitope. We conclude that the best fitted anchor- or P1Y-substituted peptide might be able to induce a RT-M184V-specific CTL repertoire that could provide an immune counter-selective pressure to prevent the M184V viral escape mutation during HIV therapy involving RT-inhibitors, such as lamivudine.

5.3. Example 3

Figure 2:
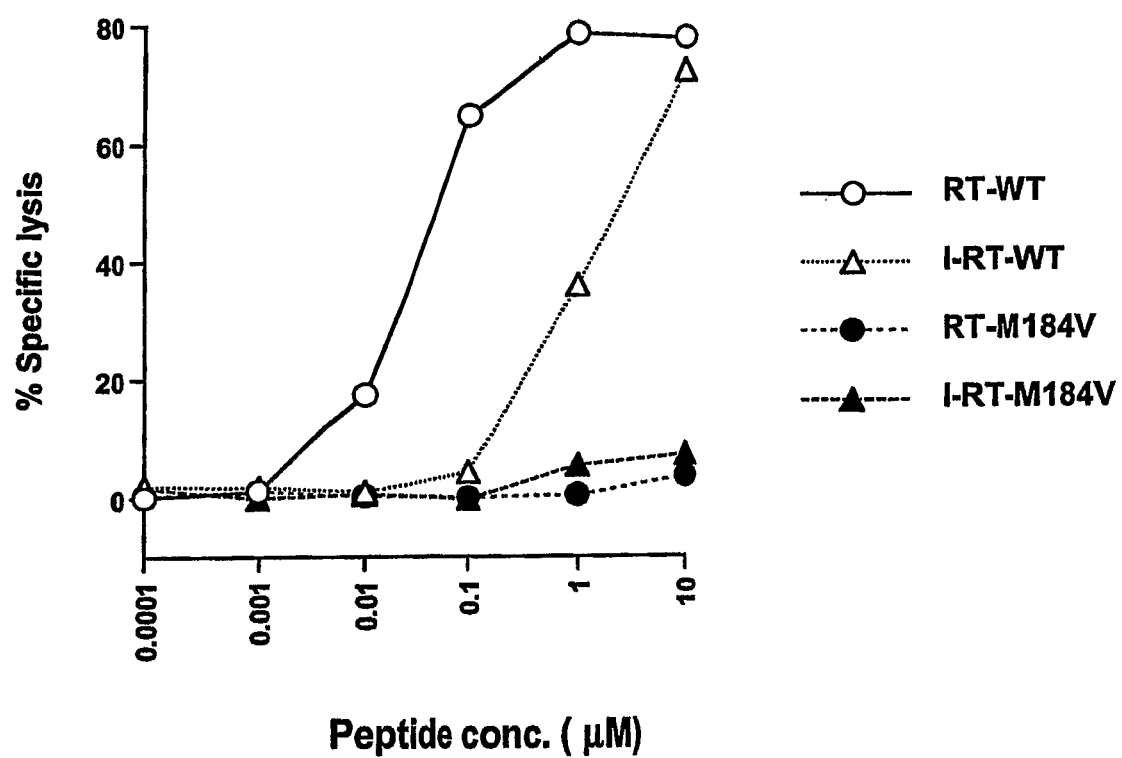
FIG. 2 shows a recognition pattern of RT-WT, RT-M184V, I-RT-WT and I-RT-M184V by RT-WT specific CTL lines. Recognition of RT-WT, I-RT-WT, RT-M184V and I-RT-M184V by RT-WT specific CTL lines from HHD-transgenic mice as a function of peptide concentration reveals differences in peptide affinity for HLA-A2 and CTL avidity for the same peptide-MHC complexes (E/T ratio, 10:1).

Recognition of RT-Variant Peptides by RT-WT-Specific CTL Lines from HHD-2 Transgenic Mice To explore the hypothesis that a best fitted anchor- or P1Y-substituted peptide might be able to induce a RT-M184-specific CTL repertoire, we first tested the recognition pattern of RT-WT-specific CTL developed from HLA-A2 transgenic mice. As shown in FIG. 2, the RT-WT-specific CTL recognized RT-WT or I-RT-WT but neither RT-M184V nor I-RT-M184V. This result in transgenic mice mirrored the previous finding of Harrer et al. involving human RT-WT-specific CTL (Harrer et al., J Infect Dis 1996, 173(2):476-479). Together, these results suggest that the lamivudine-resistance mutation abolishes recognition by an established CTL response. Furthermore, this result means that the experiment employing HLA-A2 restricted antigen specific CTL from HHD-transgenic mice is a good model of a human CTL response.

5.4. Example 4

Figure 3:
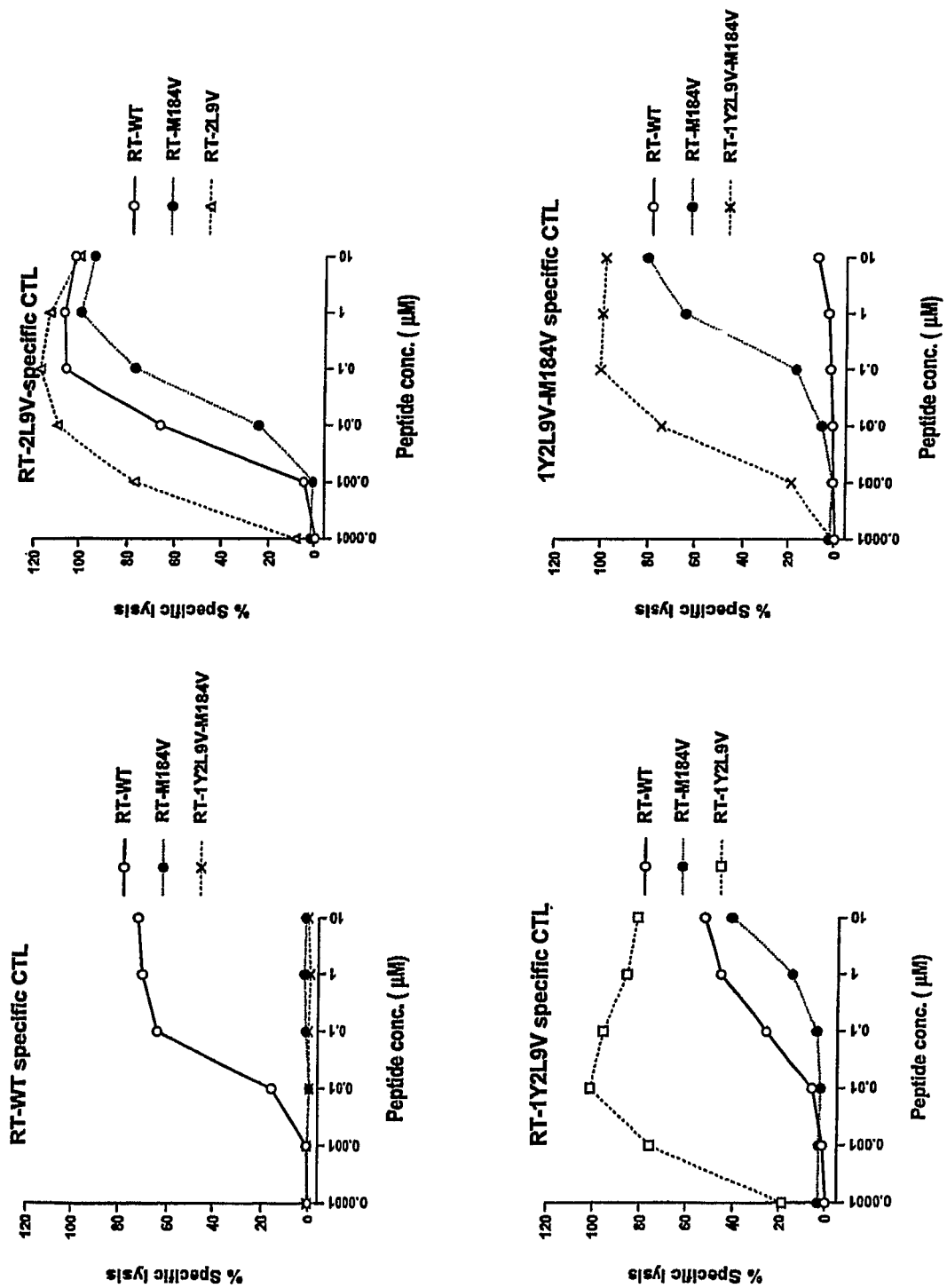
FIG. 3 shows a comparison of antigenic potency by RT-WT-, RT-2L9V -(VLYQYMDDV; SEQ ID NO:23), RT-1Y2L9V- (YLYQYMDDV; SEQ ID NO:24) and 1Y2L9V-M184V-specific CTL lines. Recognition of RT-WT, RT-M184V and each cognate peptide by RT-WT-, RT-2L9V-, RT-1Y2L9V- and 1Y2L9V-M184V-specific CTL lines from HHD-transgenic mice as a function of peptide concentration reveals differences in peptide affinity for HLA-A2 and CTL avidity for the same peptide-MHC complexes (E/T ratio, 10:1).

Recognition of RT-WT Peptide by Epitope-Enhanced Peptide Specific CTL Lines What is important in an improved vaccine is not only the binding affinity to the MHC molecules. Also the CTL induced by the improved peptide must have equal or better cross-reactivity to the wild-type epitope of a pathogen. To test this cross-reactivity to the wild-type epitope by CTL induced by the epitope-enhanced M184V peptide and based on the results of the T2-binding assay (FIG. 1), CTL lines specific for 1Y2L9V-M184V, which possessed the best binding ability of all peptides tested, were developed from HHD-transgenic mice. In concert with the RT-WT-, RT-2L9V- and RT-1Y2L9V-specific CTLs previously developed (Okazaki et al., J Immunol 2003, 171(5):2548-2555), recognition ability was compared among these four CTL types for RT-WT and RT-M184V and each cognate peptide (FIG. 3).

RT-WT specific CTL failed to recognize either RT-M184V or RT-RT-M184V as seen in FIG. 2 and previously described (Okazaki et al., J Immunol 2003, 171(5): 2548-2555). However, surprisingly and in contrast to the RT-WT-specific CTL, the anchor-enhanced RT -2L9V specific CTL line recognized both RT-WT and RT-M184V most strongly among all four CTL types. The 1Y2L9V-M184V-specific CTL recognized the RT-M184V peptide and its cognate peptide. Based on the titration curve, RT-2L9V specific CTL recognized the RT -M184V mutant epitope more efficiently than did the 1Y2L9V-M184V specific CTL. Nevertheless, the latter CTL did recognize the RT-M184V peptide. Modifications of the two anchor residues in VLY-QYVDDV (SEQ ID NO:6) produced a >2 log improvement in the binding affinity for MHC Class I over wild-type and mutant peptides. Furthermore, RT-2L9V specific CTL were able to recognize RT-WT efficiently, whereas 1Y2L9V-M184V specific CTL were not. However, the CTL repertoire elicited by the epitope-enhanced RT-2L9V-M184V appeared more selective for the RT inhibitor-induced M184V mutation. In addition, we found that RT-1Y2L9V recognized the RT-M184V mutant epitope to a lesser extent than the 1Y2L9V -M184V specific CTL. As expected, RT-1Y2L9V specific CTL recognize RT-WR better than the RT-1Y2L9V-M184V specific CTL.

These findings suggested that the P1Y mutation diminishes the RT-WT orientated specificity of the induced specific CTL, while at the same time leading to much stronger affinity for the HLA-A2 molecule. This observation is consistent with our previous data (Okazaki et al., J Immunol 2003, 171(5):2548-2555). The principle that epitope-enhanced peptide specific CTL should exhibit crossreactivity to the wild-type peptide suggests that the anchor-enhanced RT-2L9V pair of substitutions may also be a superior choice when applying the epitope-enhancement strategy to immunization against the antiviral drug-resistant M184V mutation.

5.5. Example 5

Recognition of RT-WT by 2L9V-M184V Specific CTL

Figure 4:
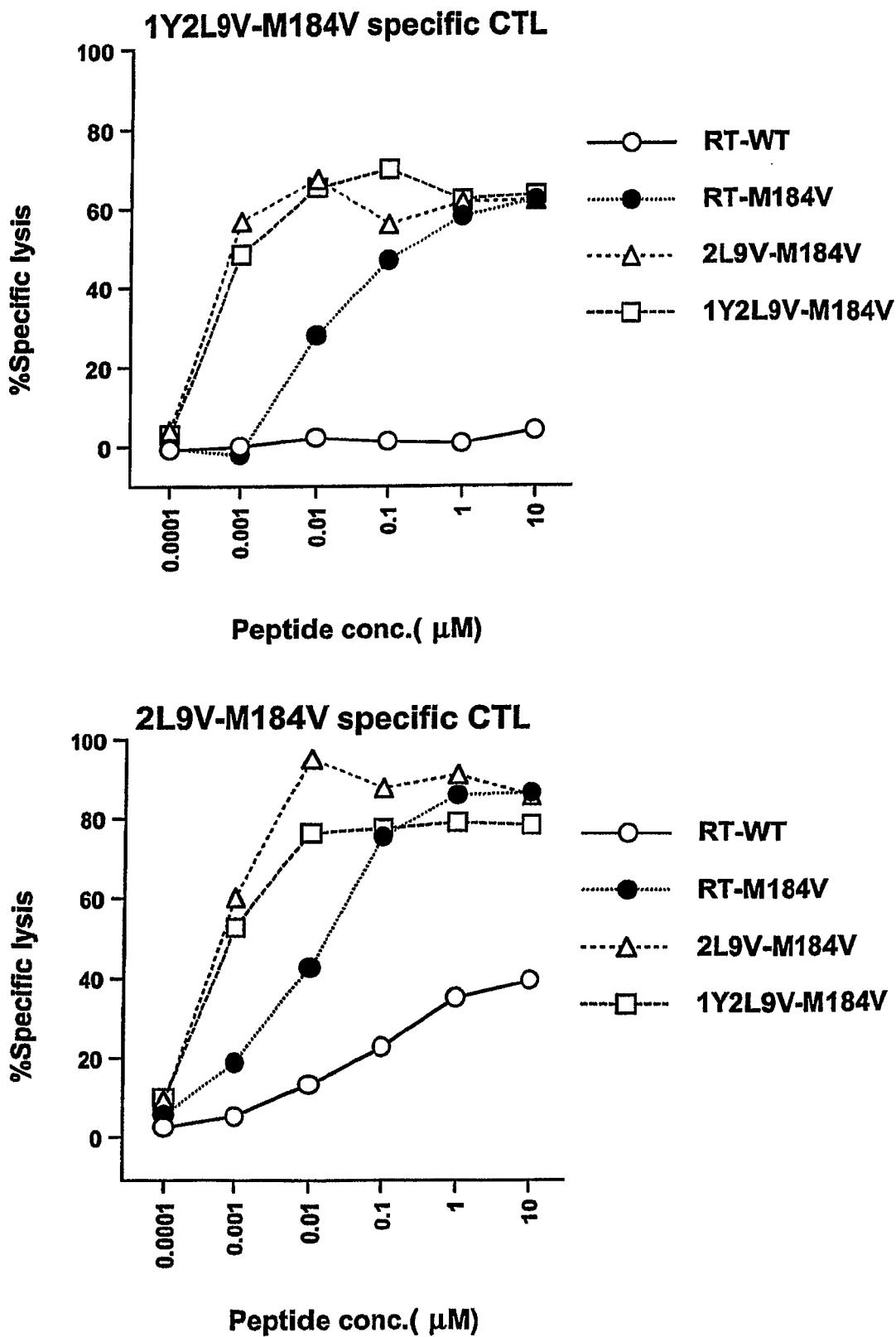
FIG. 4 shows a comparison of antigenic potency by 1Y2L9V-M184V and 2L9V-M184V specific CTL lines. Recognition of RT-WT, RT-M184V, 2L9V-M184V and 1Y2L9V-M184V by 2L9V-M184V and 1Y2L9V-M184V specific CTL lines from HHD-transgenic mice as a function of peptide concentration reveals differences in peptide affinity for HLA-A2 and CTL avidity for the same peptide-MHC complexes (E/T ratio, 10:1).
Figure 5:
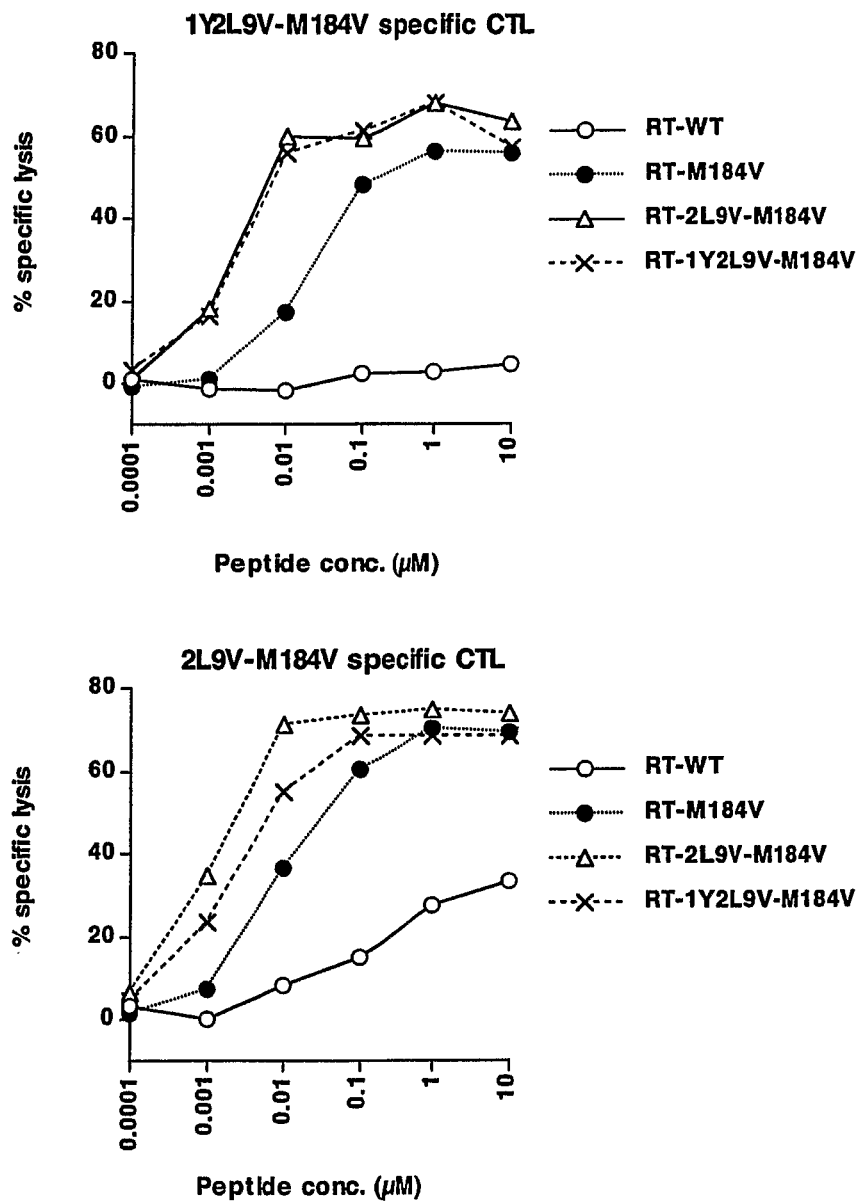
FIG. 5 shows a duplicate experiment similar to the one described in FIG. 4.

Based on findings that 2L9V-enhancement is able to induce CTL repertoires able to recognize both wild-type and M184V substituted epitopes (FIG. 3), a 2L9V-M184V specific CTL line was developed from HHD-transgenic mice to test whether the 2L9V-M184V-induced CTL line could recognize both the RT-WT and the RT-M184V mutation (FIGS. 4 and 5). In this study, 1Y2L9V-M184V specific CTL lines recognized three kinds of M184V-substituted RT peptides (RT-M184V, 2L9V-M184V, and 1Y2L9V-M184V), but RT-WT was not recognized. This result was consistent with the data of FIG. 3. On the other hand, the 2L9V-M184V specific CTL line recognized both the RT-WT epitope to some extent and the RT-M184V epitope even better. Indeed, the activity against RT-M184V was at least as potent as and possibly more potent than that by the 1Y2L9V-M184V-specific CTL line. The 2L9V-M184V specific CTL line lysed >30% of targets loaded with the M184V peptide at concentrations greater than 0.001 μM. No toxicities were observed in immunized mice. Thus, the 2L9V-M184V peptide is improved as an antigen over RT-M184V and appears to be the best candidate for inducing CTL to suppress the drug-resistant mutant virus.

5.6. Example 6

Comparison of Recognition Patterns by CTLs

The following table summarizes recognition patterns of epitopes derived from a conserved region of the HIV RT, designated RT-WT, VIYQYMDDL (SEO ID NO:1), corresponding to amino acid residues 179-187.

TABLE 6

Comparison of Recognition Patterns by CTLs

| CTL | Species | Specific Antigen | SEQ ID NO: | Recognition of RT-WT | Recognition of RT-M184V | Ref. |
|---|---|---|---|---|---|---|
| 14279-EB3 | human | VIYQYMDDL (RT-WT) | 1 | + | − | (1) |
| TE-1 | human | VIYQYVDDL (RT-M184V) | 3 | − | + | (2) |
| RT-WT | HHD mice | VIYQYMDDL (RT-WT) | 1 | ++ | − | (3), (4) |
| RT-2L9V | HHD mice | VLYQYMDDV (RT-2L9V) | 23 | ++ | ++ | (3), (4) |
| 2L9V-M184V | HHD mice | VLYQYVDDV (RT-2L9V-M184V) | 6 | +/− | ++ | (4) |
| 1Y2L9V-M184V | HHD mice | YLYQYVDDV (RT-IY2L9V-M184V) | 17 | − | + | (4) |

(1) Harrer et al., J Infect Dis 1996, 173(2): 476-479;
(2) Schmitt et al., AIDS 2000, 14(6): 653-658;
(3) Okazaki et al., J Immunol 2003, 171: 2548-2555;
(4) Catanzaro et al., this application.

5.7. Example 7

Study to Determine Safety and Activity of Epitope-Enhanced Peptides

As described herein, HIV mutants with the M184V substitution in RT have high-level resistance to the antiretroviral lamivudine (3TC). A peptide disclosed herein with the sequence VLYQYVDDV (SEQ ID NO:6; RT-2L9V-M184V) is a nonamer engineered by epitope enhancement from an HLA-A2 cytotoxic T lymphocyte (CTL) epitope of HIV RT that includes the M184V mutation. The epitope enhancement increases binding to the Class I molecule HLA-A2 and the resulting peptide induces a CTL response to the drug-resistant RT. A study will explore the safety and feasibility of administering the peptide RT-2L9V-M184V to HIV positive patients to prevent the development of resistance to lamivudine. Healthy HW positive individuals will be administered up to five vaccinations with 300 μg of RT-2L9V-M184V. The RT-2L9V-M184V may be administered with the adjuvant Montanide® ISA-51 and the cytokine sargramostim (GM-CSF). Each dose will be given at 0, 4, 8, 12 and 16 weeks. Other doses may be in the range of 100 μg to 1 mg of RT-2L9V-M184V peptide. The vaccination schedule may be varied as well, however, the proposed schedule is a minor modification of the schedule used in the Weber study that showed enhanced activity with GM-CSF (Weber et al., Cancer 2003, 97(1):186-200).

The CTL peptide VLYQYVDDV (SEQ ID NO:6; RT-2L9V-M184V) for vaccination has been produced under GMP practices and is >97% pure, with no impurity >1%, as determined by reverse phase HPLC (data not shown). Mass spectroscopy and amino acid sequencing were performed to demonstrate proper formulation (data not shown).

To guide further studies with this peptide vaccine, data will be collected and analyzed in a preliminary fashion on the CTL response to RT-2L9V-M184V. The primary endpoint will be an increase in the immune response to M184V as measured by ELISPOT assay.

Secondary data will be collected using tetramer assays specific for RT-2L9V-M184V as well as intracellular interferon gamma production after stimulation with the immunizing peptide. This can be accomplished, by, e.g., using flow cytometry. In addition, the effect of RT-2L9V-M184V vaccination on HIV viral load, CD4 count, and CD8 count will be determined. Further, the development of lamividune or emtracitabine (FTC) resistance in patients who subsequently receive lamividune or emtracitabine (FTC) will be explored.

5.8. Example 8

Stability of Epitope-Enhanced Peptides

CTL peptides of the present invention, including the CTL peptide VLYQYVDDV (SEQ ID NO:6; RT-2L9V-M184V), are provided in, e.g., phosphate buffered saline (PBS), pH 7.2 at a vialing concentration of 1.6 mg/ml. The CTL peptide VLYQYVDDV (SEQ ID NO:6; RT-2L9V-M184V) has been found to be stable for 3 months when stored at controlled room temperature (15° C.-30° C.), for at least 9 months when stored in the refrigerator (2° C.-8° C.) and for at least 18 months when stored in the freezer (−10° C. to −25° C. and −70° C.) (data not shown). The recommended storage of intact vials of the CTL peptide VLYQYVDDV (SEQ ID NO:6; RT-2L9V-M184V) is at or below −70° C. The peptide is stable through at least two freeze-thaw-freeze cycles.

Further, the CTL peptide VLYQYVDDV (SEQ ID NO:6; RT-2L9V-M184V) (at concentrations to be used for vialing:

1.6 mg/ml) was tested for stability at 4° C. and 22° C. by HPLC. No degradation was observed by 7 days. The peptide is stable to freezing and thawing and is not significantly lost by adsorption onto the borosilicate glass vial at the concentrations to be used for vialing (data not shown).

When the the CTL peptide VLYQYVDDV (SEQ ID NO:6; RT-2L9V-M184V) is mixed with Montanide® ISA-51 (in order to administer e.g., a 300 µg dose), the emulsion formed has been shown by microscopic observation to be physically stable for a 3 hour time period (data not shown).

5.9. Example 9

Preparation and Administration Procedure

To prepare a 300 µg dose of the CTL peptide VLYQYVDDV (SEQ ID NO:6; RT -2L9V-M184V), 0.25 mL of Montanide® ISA-51 is added to a vial of the CTL peptide (1.6 mg/mL, 0.25 mL per vial). The vial is then vortexed for about 12 minutes at a minimum of 3,000 rpm. 0.375 mL are withdrawn for administration. The dose will be given as a single subcutaneous injection, using a 20 or 21 gauge needle. The site of injection will include the upper arm, the thigh or lower abdomen. Sites will be rotated with each injection. A Montanide -CTL peptide emulsion should be administered as soon as possible, and always within 3 hours of preparation.

5.10. Example 10

GM-CSF/Sagramostim for Coadministration with a CTL Peptide

Sargramostim has been used safely in patients infected with HIV. Evidence from a several studies suggest that sargramostim is safe, and results in a slight decrease in viral load with little impact on the CD4 count.

A preferred sargramostim for use in the methods of this invention is a glycosylated, recombinant human sargramostim. This sargramostim is an altered form of the native molecule. The position 23 arginine has been replaced with a leucine to facilitate the expression in yeast (*Saccharomyces cerevisiae*). The product consists of a white lyophilized cake and is provided in vials containing 250 µg of sargramostim. It is also available in 500 µg vials as a liquid.

To prepare a vial of sargramostim for use, 1.0 ml of bacteriostatic water for injection is aseptically inject into the 250 µg vial to dissolve the lyophilized cake. The solution in the vial is swirled to dissolve the powder. Vigorous agitation of the vial is avoided. This yields a solution containing 250 µg/ml. The 500 µg vial contains an injectable solution.

Intact 250 µg/ml powder or 500 µg/ml liquid vials should be stored at 2-8° C. in the refrigerator.

When the 250 µg vial is reconstituted with bacteriostatic water for injection, the drug maintains stability for 20 days when stored in the refrigerator. Freezing should be avoided. When reconstituted with Sterile Water for Injection (SWI), the injection should be administered as soon as possible and within 6 hours following reconstitution. The vial should not be reentered or reused. The 500 µg/ml liquid GM-CSF is stable for up to 20 days after initial entry into the vial. Both the reconstituted liquid and the 500 µg vials should be stored in the refrigerator (2-8° C.) after initial entry into the vial.

Sargramostim can be administered subcutaneously at a dose of 250 µg in a 1 ml syringe. Preferably, it should be administered on the distal side of the vaccination site of the CTL peptide immediately after the vaccination (day 1), and then in the same site for the next 3 days (days 2 to 4).

5.11. Example 11

Discussion

Combination drug therapies for the treatment of AIDS dramatically decreased the number of AIDS-related deaths. RT inhibitors, such as the nucleoside analog (–)-2',3'-deoxy-3'-thiacytidine (3TC), are important components of these multi-drug treatment regimens (Pluda et al., Cancer Chemother Biol Response Modif 1992, 13:404-439; Reijers et al., Lancet 1998, 352:185-190; Carpenter et al., JAMA 1998, 280:78-86; Yeni et al., JAMA 2002, 288(2):222-235). However, the selective pressure for escape from RT-inhibitors often leads to escape mutations in RT. In the case of lamivudine (3TC), such pressure usually leads to the selection of highly resistant HIV with the substitution of valine for methionine at position 184 of HIV-1 RT. Similar mutations at the equivalent position in HBV polymerase and in simian immunodeficiency virus and feline immunodeficiency virus RTs confer resistance to 3TC (Sarafianos et al., Proc Natl Acad Sci USA 1999, 96(18):10027-10032).

Compounding this problem, this M184V mutation enables HIV to escape immune pressure of CTLs specific for the wild-type RT sequence in hosts, preferably patients, with HLA-A2, which is the most common HLA class I molecule worldwide. This mechanism implies that a single mutation can lead to the escape of HIV not only from the drug-induced pressure of RT-inhibitors but also from CTL-induced immune selective pressure in hosts (patients) displaying the HLA-A2 haplotype, resulting in the appearance of drug-resistant and CTL-resistant HIV strains. As shown herein, a potential approach to prevent the appearance of drug-resistant strains is the induction of CTL specific for drug-resistant mutant epitopes through the use of a vaccine designed using an epitope enhancement strategy.

To address this issue in the context of HIV, we first examined whether the RT-M184V drug-resistant mutant possessed the ability to bind the HLA-A2 molecule. As shown in FIG. 1, the RT-M184V peptide displayed binding to HLA-A2 at least as good as or even better than RT -WT, indicating that RT-M184V could be a CTL epitope restricted to HLA-A2. In addition, we assessed whether the RT-WT specific CTL line developed from HHD-transgenic mice could recognize RT-M184V. The RT-WT specific CTL failed to recognize RT-M184V. Thus, the RT-M184V mutation allows escape not only from the drug 3TC, but also from immune selective pressure by CTL specific for the wild-type epitope VIYQYMDDL (SEQ ID NO:1). This result, which is consistent with data derived from a human CTL line (Harrer et al., J Infect Dis 1996, 173(2):476-479), suggests that such a CTL study in mice expressing this HLA molecule, as the sole class I MHC molecule, should be directly translatable to human vaccines.

The binding data confirmed the prediction that peptides with position 1 substituted with tyrosine (P1Y), such as 1Y2L9V-M184V, exhibited higher binding ability to HLA-A2. However, to develop an improved vaccine, not only must the binding affinity to the MHC molecule be improved, but also the CTL induced by the improved peptide must display crossreactivity to the wild type epitope of a pathogen. For this reason, the 1Y2L9V-M184V specific CTL line was developed from HHD mice to assess crossreactivity of the 1Y2L9V-M184V specific CTL to the M184V mutation and RT-WT (FIG. 3). 1Y2L9V-M184V specific CTL recognized RT-M184V, but not RT-WT. This finding indicates that the P1Y mutation induced a CTL repertoire skewed away from clones recognizing the wild-type sequence. This result is consistent with our previous data with RT-1Y2L9V (Okazaki et al., J Immunol 2003, 171:2548-2555).

In contrast, the RT-2L9V specific CTL line recognized both RT-M184V and RT-WT more efficiently than did 1Y2L9V-M184V specific CTL. RT-2L9V is an enhanced epitope of RT-WT containing the optimum anchor residues for peptide binding to HLA-A2, which are leucine and valine at the 2nd and 9th positions of the peptide, respectively (Rammensee et al., Immunogenetics 1995, 41(4):178-228). Its binding ability to HLA-A2 is approximately 8-fold greater than that of RT-WT (Okazaki et al., J Immunol 2003, 171:2548-2555).

Generally, amino acids in the anchor positions of a CTL epitope are thought not to participate in alteration of T cell receptor (TCR)-recognition. Nevertheless, the fact that 2L9V substitution produces reactivity to the M184V epitope by the specific CTL might suggest that any adverse interaction at peptide position 6 (RT184) between antigenic peptide and TCR might be sufficiently weak that it is more than compensated by the increased affinity for the MHC molecule afforded by the 2L9V substitutions. Alternatively, the optimized anchor residues may stabilize the appropriate conformation. Based on these findings, the 2L9V-M184V substitution may be the best candidate for a protective vaccine epitope against the RT-M184V mutant.

To test this idea further, we developed the 2L9V-M184V-specific CTL line from HHD mice in order to compare the recognition pattern between 1Y2L9V- and 2L9V-specific CTL (FIGS. 4 and 5). The 2L9V-specific CTL line also recognized RT-WT and RT-M184V, whereas RT-M184V specific human CTL recognized only RT-M184V but not RT-WT (Schmitt et al., AIDS 2000, 14(6):653-658). However, the recognition ability of RT-WT peptide by 2L9V-M184V-specific CTL was slightly weaker than that of RT-2L9V specific CTL. Thus, the 2L9V-M184V-specific CTL more selectively recognize the drug-resistant escape mutants and therefore may more effectively exert immunologic counter pressure to balance the selective pressure of the drug (e.g., lamivudine) for resistant mutants.

An epitope-enhanced peptide should have a high binding affinity for an MHC molecule and induce the epitope-reactive CTL repertoires more efficiently. Thus, 2L9V-M184V represents a good therapeutic vaccine candidate to prevent or delay appearance of the M184V mutation induced by the nucleoside RT-inhibitor 3TC used in antiviral therapy in individuals expressing HLA-A2 (Table 6). This strategy may work most effectively if used early in drug therapy (e.g., lamivudine therapy) when the resistant variants a very minor component of the viral swarm. RT-2L9V can function as a prophylactic vaccine to induce more broadly crossreactive CTL against HIV, whereas 2L9V-M184V may be more effective as a therapeutic vaccine that may work synergistically with HAART (Highly Active Antiviral Therapy) that includes lamivudine as one of its components.

Although this epitope contains the major resistance mutation for lamivudine, one could also include epitopes containing resistance mutations at other sites in HIV reverse transcriptase to completely prevent the outgrowth of resistant strains. Nevertheless, CTL immunity to this epitope can slow the appearance of resistant mutations at amino acid residue 184 relative to other resistance mutations in the protein. This would possibly prolong the duration of efficacy of lamivudine in the immunized subjects (e.g., patients).

The invention described herein provides for therapeutic vaccines involving an epitope-enhanced peptide strategy to prevent or delay the appearance of HIV-1 drug-resistant mutants during anti-retroviral therapy. Additionally, the invention provides for the production of enhanced epitopes that can be applied to the construction of next-generation vaccines, applicable to all forms of vaccine, peptide, DNA, recombinant viral or bacterial vector, or live attenuated virus. Finally, the invention described herein provides for and demonstrates the efficacy of a prototype conserved enhanced epitope that can be incorporated into many candidate vaccines currently under investigation.

What is claimed is:

1. A method for lowering HIV-1 viral load and reducing the emergence of antiviral-drug-resistant HIV-1 strains, the method comprising administering to a host a synthetic peptide before the administration of the antiviral drug, wherein:

i) the antiviral drug is in an amount effective to restrict intracellular multiplication of the virus, wherein the antiviral drug is capable of selecting for a predetermined antiviral drug-resistant mutation in the highly conserved catalytic site sequence VIYQYMDDL (SEQ ID NO: 1) of HIV-1 reverse transcriptase thereby creating an antiviral drug-resistant virus, wherein the predetermined mutation is a substitution of the M residue of SEQ ID NO: 1 by an A, V or I residue, and (ii) the synthetic peptide has a length of between 9 and 15 amino acid residues, comprising the amino acid sequence of LYQYVDDV (SEQ ID NO:19), VLYQYVDDV (SEQ ID NO:6), or YLYQYVDDV (SEQ ID NO:17), and the synthetic peptide induces a cytotoxic T lymphocyte response specific for cells infected with the antiviral drug-resistant virus and provides an immune counter-selective pressure to suppress a viral escape during antiviral therapy thereby lowering the viral load.

2. The method of claim 1, wherein the synthetic peptide comprises the amino acid sequence VLYQYVDDV (SEQ ID NO:6).

3. The method of claim 1, wherein the antiviral drug is lamuvidine.

4. The method of claim 2, wherein the antiviral drug comprises zidovudine, didanosine, zalcitabine, or didanosine, emtracitabine, (−)FTC, or the (−) enantiomer of 2′,3′-dideoxy-3′-thiacytidine [(−)-BCH-189].

* * * * *

SEQUENCE LISTING

```
<160> NUMBER OF SEQ ID NOS: 41

<210> SEQ ID NO 1
<211> LENGTH: 9
<212> TYPE: PRT
<213> ORGANISM: Artificial Sequence
<220> FEATURE:
<223> OTHER INFORMATION: conserved HLA-A2-restricted cytotoxic T
      lymphocyte (CTL) epitope in human immunodeficiency virus 1
      (HIV-1) drug-sensitive wild-type reverse
      transcriptase (RT-WT), residues 179-187

<400> SEQUENCE: 1

Val Ile Tyr Gln Tyr Met Asp Asp Leu
1               5

<210> SEQ ID NO 2
<211> LENGTH: 4
<212> TYPE: PRT
<213> ORGANISM: Artificial Sequence
<220> FEATURE:
<223> OTHER INFORMATION: conserved YMDD motif in human immunodeficiency
      virus 1 (HIV-1), simian immunodeficiency virus (SIV) and feline
      immunodeficiency virus (FIV) reverse transcriptases (RT) and
      hepatitis B virus (HBV) polymerase
```

```
<400> SEQUENCE: 2

Tyr Met Asp Asp
 1

<210> SEQ ID NO 3
<211> LENGTH: 9
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT) with epitope enhancement,
      synthetic peptide RT-M184V

<400> SEQUENCE: 3

Val Ile Tyr Gln Tyr Val Asp Asp Leu
 1               5

<210> SEQ ID NO 4
<211> LENGTH: 9
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT) with epitope enhancement,
      synthetic peptide

<400> SEQUENCE: 4

Val Ile Tyr Gln Tyr Ile Asp Asp Leu
 1               5

<210> SEQ ID NO 5
<211> LENGTH: 9
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT) with epitope enhancement,
      synthetic peptide

<400> SEQUENCE: 5

Val Leu Tyr Gln Tyr Ile Asp Asp Val
 1               5

<210> SEQ ID NO 6
<211> LENGTH: 9
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT) with epitope enhancement,
      synthetic peptide RT-2L9V-M184V

<400> SEQUENCE: 6

Val Leu Tyr Gln Tyr Val Asp Asp Val
 1               5

<210> SEQ ID NO 7
<211> LENGTH: 15
<212> TYPE: PRT
<213> ORGANISM: Artificial Sequence
<220> FEATURE:
<223> OTHER INFORMATION: predetermined antiviral drug-resistant mutation
      D67N substitution in human immunodeficiency virus
      1 (HIV-1) reverse transcriptase (RT), synthetic
      peptide
```

<400> SEQUENCE: 7

Val Phe Ala Ile Lys Lys Lys Asn Ser Thr Lys Trp Arg Lys Leu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: predetermined antiviral drug-resistant mutation
      D67N substitution in human immunodeficiency virus
      1 (HIV-1) reverse transcriptase (RT), synthetic
      peptide

<400> SEQUENCE: 8

Pro Val Phe Ala Ile Lys Lys Lys Asn Ser Thr Lys Trp Arg Lys
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: predetermined antiviral drug-resistant mutation
      D67N substitution in human immunodeficiency virus
      1 (HIV-1) reverse transcriptase (RT), synthetic
      peptide

<400> SEQUENCE: 9

Phe Ala Ile Lys Lys Lys Asn Ser Thr Lys Trp Arg Lys Leu Val
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: predetermined antiviral drug-resistant mutation
      K70R substitution in human immunodeficiency virus
      1 (HIV-1) reverse transcriptase (RT), synthetic
      peptide

<400> SEQUENCE: 10

Ala Ile Lys Lys Lys Asp Ser Thr Arg Trp Arg Lys Leu Val Asp
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: predetermined antiviral drug-resistant mutation
      K70R substitution in human immunodeficiency virus
      1 (HIV-1) reverse transcriptase (RT), synthetic
      peptide

<400> SEQUENCE: 11

Ile Lys Lys Lys Asp Ser Thr Arg Trp Arg Lys Leu Val Asp Phe
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: predetermined antiviral drug-resistant mutation
      K70R substitution in human immunodeficiency virus
      1 (HIV-1) reverse transcriptase (RT), synthetic

```
            peptide

<400> SEQUENCE: 12

Lys Lys Lys Asp Ser Thr Arg Trp Arg Lys Leu Val Asp Phe Arg
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: predetermined antiviral drug-resistant
      mutations D67N and K70R substitutions in human
      immunodeficiency virus 1 (HIV-1) reverse
      transcriptase (RT), synthetic peptide

<400> SEQUENCE: 13

Val Phe Ala Ile Lys Lys Lys Asn Ser Thr Arg Trp Arg Lys Leu
1               5                   10 transcriptase (RT) with epitope enhancement,
synthetic peptide 1Y2L9V-M184V

<400> SEQUENCE: 17

Tyr Leu Tyr Gln Tyr Val Asp Asp Val
1               5

<210> SEQ ID NO 18
<211> LENGTH: 9
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT) with epitope enhancement,
      synthetic peptide

<400> SEQUENCE: 18

Tyr Leu Tyr Gln Tyr Ile Asp Asp Val
1               5

<210> SEQ ID NO 19
<211> LENGTH: 8
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT) with epitope enhancement,
      immunostimulating peptide

<400> SEQUENCE: 19

Leu Tyr Gln Tyr Val Asp Asp Val
1               5

<210> SEQ ID NO 20
<211> LENGTH: 8
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT) with epitope enhancement,
      immunostimulating peptide

<400> SEQUENCE: 20

Leu Tyr Gln Tyr Ile Asp Asp Val
1               5

<210> SEQ ID NO 21
<211> LENGTH: 10
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT), synthetic peptide I-RT-WT

<400> SEQUENCE: 21

Ile Val Ile Tyr Gln Tyr Met Asp Asp Leu
1               5                   10

<210> SEQ ID NO 22
<211> LENGTH: 10
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse transcriptase (RT), synthetic peptide I-RT-M184V

<400> SEQUENCE: 22

Ile Val Ile Tyr Gln Tyr Val Asp Asp Leu
1               5                   10

<210> SEQ ID NO 23
<211> LENGTH: 9
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT) with epitope enhancement,
      immunostimulating peptide RT-2L9V

<400> SEQUENCE: 23

Val Leu Tyr Gln Tyr Met Asp Asp Val
1               5

<210> SEQ ID NO 24
<211> LENGTH: 9
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT) with epitope enhancement,
      immunostimulating peptide RT-1Y2L9V

<400> SEQUENCE: 24

Tyr Leu Tyr Gln Tyr Met Asp Asp Val
1               5

<210> SEQ ID NO 25
<211> LENGTH: 15
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse
      transcriptase (RT), immunostimulating peptide

<400> SEQUENCE: 25

Ala Ala Ala Val Ile Tyr Gln Tyr Val Asp Asp Leu Gly Gly Gly
1               5                   10                  15

<210> SEQ ID NO 26
<211> LENGTH: 5
<212> TYPE: PRT
<213> ORGANISM: Artificial Sequence
<220> FEATURE:
<223> OTHER INFORMATION: Y-1 residues identical to human
      immunodeficiency virus 1 (HIV-1) reverse transcriptase (RT) in
      antiviral drug-resistant virus amino terminal to predetermined
      antiviral drug-resistant mutation (P-M) in formula for
      immunostimulating peptide

<400> SEQUENCE: 26

Val Ile Tyr Gln Tyr
1               5

<210> SEQ ID NO 27
<211> LENGTH: 15
<212> TYPE: PRT
<213> ORGANISM: Artificial Sequence
<220> FEATURE:
<223> OTHER INFORMATION: predetermined antiviral drug-resistant mutation
      in human immunodeficiency virus 1 (HIV-1) reverse transcriptase (RT), immunostimulating peptide

<400> SEQUENCE: 27

Ala Ala Ala Val Leu Tyr Gln Tyr Val Asp Asp Val Gly Gly Gly
1               5                   10                  15

<210> SEQ ID NO 28
<211> LENGTH: 5
<212> TYPE: PRT
<213> ORGANISM: Artificial Sequence
<220> FEATURE:
<223> OTHER INFORMATION: Y-1 residues with epitope enhancement in HIV-1
      reverse transcriptase (RT) in antiviral drug-resistant virus amino
      terminal to predetermined antiviral drug-resistant mutation
      (P-M) in formula for immunostimulating peptide

<400> SEQUENCE: 28

Val Leu Tyr Gln Tyr
1               5

<210> SEQ ID NO 29
<211> LENGTH: 21
<212> TYPE: PRT
<213> ORGANISM: Artificial Sequence
<220> FEATURE:
<223> OTHER INFORMATION: predetermined antiviral drug-resistant
      mutations in human immunodeficiency virus 1 (HIV-1) reverse
      transcriptase (RT), immunostimulating peptide

<400> SEQUENCE: 29

Ala Ala Ala Val Phe Ala Ile Lys Lys Lys Asn Ser Thr Arg Trp Arg
1               5                   10                  15

Lys Leu Gly Gly Gly
            20

<210> SEQ ID NO 30
<211> LENGTH: 7
<212> TYPE: PRT
<213> ORGANISM: Artificial Sequence
<220> FEATURE:
<223> OTHER INFORMATION: Y-1 residues identical to human
      immunodeficiency virus 1 (HIV-1) reverse transcriptase (RT) in
      antiviral drug-resistant virus amino terminal to predetermined
      antiviral drug-resistant mutation (P-M1) in formula for
      immunostimulating peptide

<400> SEQUENCE: 30

Val Phe Ala Ile Lys Lys Lys
1               5

<210> SEQ ID NO 31
<211> LENGTH: 4
<212> TYPE: PRT
<213> ORGANISM: Artificial Sequence
<220> FEATURE:
<223> OTHER INFORMATION: Y-2 residues identical to human
      immunodeficiency virus 1 (HIV-1) reverse transcriptase (RT) in
      antiviral drug-resistant virus carboxy terminal to predetermined
      antiviral drug-resistant mutation (P-M2) in formula for
      immunostimulating peptide

<400> SEQUENCE: 31

Trp Arg Lys Leu
1

<210> SEQ ID NO 32
<211> LENGTH: 13
<212> TYPE: PRT

```
<213> ORGANISM: Artificial Sequence
<220> FEATURE:
<223> OTHER INFORMATION: human immunodeficiency virus 1 (HIV-1) reverse
      transcriptase (RT) wild-type sequence

<400> SEQUENCE: 32

Met Val Ile Tyr Gln Tyr Met Asp Asp Leu Tyr Val Gly
1               5                   10

<210> SEQ ID NO 33
<211> LENGTH: 13
<212> TYPE: PRT
<213> ORGANISM: Artificial Sequence
<220> FEATURE:
<223> OTHER INFORMATION: human immunodeficiency virus 1 (HIV-1) reverse
      transcriptase (RT) with M184V substitution
      predetermined antiviral drug-resistant mutation

<400> SEQUENCE: 33

Met Val Ile Tyr Gln Tyr Val Asp Asp Leu Tyr Val Gly
1               5                   10

<210> SEQ ID NO 34
<211> LENGTH: 7
<212> TYPE: PRT
<213> ORGANISM: Artificial Sequence
<220> FEATURE:
<223> OTHER INFORMATION: peptide with amino acid residues of antiviral
      drug-resistant virus flanking predetermined antiviral
      drug-resistant mutation in human immunodeficiency virus 1 (HIV-1)
      reverse transcriptase (RT)

<400> SEQUENCE: 34

Met Val Ile Tyr Gln Tyr Val
1               5

<210> SEQ ID NO 35
<211> LENGTH: 7
<212> TYPE: PRT
<213> ORGANISM: Artificial Sequence
<220> FEATURE:
<223> OTHER INFORMATION: peptide with amino acid residues of antiviral
      drug-resistant virus flanking predetermined antiviral
      drug-resistant mutation in human immunodeficiency virus 1 (HIV-1)
      reverse transcriptase (RT)

<400> SEQUENCE: 35

Val Ile Tyr Gln Tyr Val Asp
1               5

<210> SEQ ID NO 36
<211> LENGTH: 7
<212> TYPE: PRT
<213> ORGANISM: Artificial Sequence
<220> FEATURE:
<223> OTHER INFORMATION: peptide with amino acid residues of antiviral
      drug-resistant virus flanking predetermined antiviral
      drug-resistant mutation in human immunodeficiency virus 1 (HIV-1)
      reverse transcriptase (RT)

<400> SEQUENCE: 36

Ile Tyr Gln Tyr Val Asp Asp
1               5

<210> SEQ ID NO 37
<211> LENGTH: 7
<212> TYPE: PRT
<213> ORGANISM: Artificial Sequence
<220> FEATURE:
```

```
<223> OTHER INFORMATION: peptide with amino acid residues of antiviral
      drug-resistant virus flanking predetermined antiviral
      drug-resistant mutation in human immunodeficiency virus 1 (HIV-1)
      reverse transcriptase (RT)

<400> SEQUENCE: 37

Tyr Gln Tyr Val Asp Asp Leu
1               5

<210> SEQ ID NO 38
<211> LENGTH: 7
<212> TYPE: PRT
<213> ORGANISM: Artificial Sequence
<220> FEATURE:
<223> OTHER INFORMATION: peptide with amino acid residues of antiviral
      drug-resistant virus flanking predetermined antiviral
      drug-resistant mutation in human immunodeficiency virus 1 (HIV-1)
      reverse transcriptase (RT)

<400> SEQUENCE: 38

Gln Tyr Val Asp Asp Leu Tyr
1               5

<210> SEQ ID NO 39
<211> LENGTH: 7
<212> TYPE: PRT
<213> ORGANISM: Artificial Sequence
<220> FEATURE:
<223> OTHER INFORMATION: peptide with amino acid residues of antiviral
      drug-resistant virus flanking predetermined antiviral
      drug-resistant mutation in human immunodeficiency virus 1 (HIV-1)
      reverse transcriptase (RT)

<400> SEQUENCE: 39

Tyr Val Asp Asp Leu Tyr Val
1               5

<210> SEQ ID NO 40
<211> LENGTH: 7
<212> TYPE: PRT
<213> ORGANISM: Artificial Sequence
<220> FEATURE:
<223> OTHER INFORMATION: peptide with amino acid residues of antiviral
      drug-resistant virus flanking predetermined antiviral
      drug-resistant mutation in human immunodeficiency virus 1 (HIV-1)
      reverse transcriptase (RT)

<400> SEQUENCE: 40

Val Asp Asp Leu Tyr Val Gly
1               5

<210> SEQ ID NO 41
<211> LENGTH: 9
<212> TYPE: PRT
<213> ORGANISM: Artificial Sequence
<220> FEATURE:
<223> OTHER INFORMATION: positive control highly antigenic influenza
      matrix peptide (FMP) amino acid residues 58-66

<400> SEQUENCE: 41

Gly Ile Leu Gly Phe Val Phe Thr Leu
1               5
```